(12) United States Patent
Bouquin et al.

(10) Patent No.: US 10,450,376 B2
(45) Date of Patent: Oct. 22, 2019

(54) ANTI-MET ANTIBODIES AND COMPOSITIONS

(71) Applicant: SYMPHOGEN A/S, Ballerup (DK)

(72) Inventors: Thomas Bouquin, Allerød (DK); Mikkel Wandahl Pedersen, Allerød (DK); Helle Jane Jacobsen, Virum (DK); Thomas Tuxen Poulsen, Dyssegaard (DK); Michael Monrad Grandal, Ballerup (DK); Klaus Koefoed, Copenhagen W (DK); Michael Kragh, Copenhagen N (DK); Karsten Wessel Eriksen, Espergaerde (DK); Paolo Conrotto, Brøndby Strand (DK)

(73) Assignee: Symphogen A/S, Ballerup (DK)

( * ) Notice: Subject to any disclaimer, the term of this patent is extended or adjusted under 35 U.S.C. 154(b) by 44 days.

(21) Appl. No.: 15/510,545

(22) PCT Filed: Sep. 15, 2015

(86) PCT No.: PCT/IB2015/002110
§ 371 (c)(1),
(2) Date: Mar. 10, 2017

(87) PCT Pub. No.: WO2016/042412
PCT Pub. Date: Mar. 24, 2016

(65) Prior Publication Data
US 2018/0327500 A1    Nov. 15, 2018

Related U.S. Application Data

(60) Provisional application No. 62/051,190, filed on Sep. 16, 2014.

(51) Int. Cl.
| | | |
|---|---|---|
| *C07K 16/28* | (2006.01) | |
| *A61K 39/395* | (2006.01) | |
| *C07K 16/30* | (2006.01) | |
| *A61K 45/06* | (2006.01) | |
| *A61K 47/68* | (2017.01) | |
| *A61K 39/00* | (2006.01) | |

(52) U.S. Cl.
CPC ...... *C07K 16/2863* (2013.01); *A61K 39/3955* (2013.01); *A61K 45/06* (2013.01); *A61K 47/6879* (2017.08); *A61K 2039/507* (2013.01); *C07K 2317/24* (2013.01); *C07K 2317/30* (2013.01); *C07K 2317/31* (2013.01); *C07K 2317/34* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
CPC .................................................. C07K 16/28
See application file for complete search history.

(56) References Cited

U.S. PATENT DOCUMENTS

| | | |
|---|---|---|
| 5,686,292 A | 11/1997 | Schwall et al. |
| 5,707,624 A | 1/1998 | Nickoloff et al. |
| 6,099,841 A | 8/2000 | Hillan et al. |
| 6,207,152 B1 | 3/2001 | Schwall et al. |
| 6,214,344 B1 | 4/2001 | Schwall et al. |
| 7,476,724 B2 | 1/2009 | Dennis et al. |
| 7,498,420 B2 | 3/2009 | Michaud et al. |
| 7,556,804 B2 | 7/2009 | Prat et al. |
| 7,615,529 B2 | 11/2009 | Kong-Beltran et al. |
| 7,892,770 B2 | 2/2011 | Cao et al. |
| 8,039,598 B2 | 10/2011 | Cao et al. |
| 8,101,727 B2 | 1/2012 | Stover et al. |
| 8,124,085 B2 | 2/2012 | Nielsen et al. |
| 8,133,867 B2 | 3/2012 | Otsuka et al. |
| 8,217,148 B2 | 7/2012 | Davies et al. |
| 8,309,315 B2 | 11/2012 | Cao et al. |
| 8,329,173 B2 | 12/2012 | Goetsch et al. |
| 8,455,623 B2 | 6/2013 | Van Der Horst et al. |

FOREIGN PATENT DOCUMENTS

| | | | |
|---|---|---|---|
| EP | 0805203 B1 | 8/2007 | |
| EP | 0922102 B1 | 4/2010 | |
| EP | 1981981 B1 | 6/2011 | |
| EP | 1957102 B1 | 1/2012 | |
| EP | 2635603 B1 | 3/2016 | |
| WO | WO 92/01047 | 1/1992 | |
| WO | WO 93/06213 | 4/1993 | |
| WO | WO 2005/042774 | 5/2005 | |
| WO | WO 2009/007427 | 1/2009 | |
| WO | WO 2009/142738 | 11/2009 | |
| WO | WO 2010/059654 | 5/2010 | |
| WO | WO-2010059654 A1 * | 5/2010 | ......... C07K 16/2863 |
| WO | WO 2011/110642 | 9/2011 | |
| WO | WO 2012/059562 | 5/2012 | |
| WO | WO 2012/059857 | 5/2012 | |
| WO | WO 2012/059858 | 5/2012 | |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Tzartos et al., Methods in Molecular Biology, 1996, 66:55-66.*

(Continued)

*Primary Examiner* — Hong Sang
(74) *Attorney, Agent, or Firm* — Steptoe & Johnson LLP; Ying Li; Wyan-Ching M. Lee

(57) ABSTRACT

The present invention relates to novel recombinant antibodies directed against human MET (c-MET), as well as compositions comprising mixtures of at least two of said antibodies and use of the antibodies and antibody compositions for treatment of MET-mediated disorders such as cancer.

23 Claims, 30 Drawing Sheets

Specification includes a Sequence Listing.

(56) References Cited

OTHER PUBLICATIONS

Abidoye et al., "Review of clinic trials: agents targeting c-Met," Rev Recent Clin Trials 2(2):143-7 (2007).

Basilico et al., "A high affinity hepatocyte growth factor-binding site in the immunoglobulin-like region of Met," J Biol Chem 283(30):21267-77 (2008).

Basilico et al., "Four individually druggable MET hotspots mediate HGF-driven tumor progression," J. Clin Invest. 124(7):3172-86 (2014).

Cao et al., "Neutralizing monoclonal antibodies to hepatocyte growth factor/scatter factor (HGF/SF) display antitumor activity in animal models," Proc Natl Acad Sci USA 98(13): 7443-7448 (2001).

Gherardi et al., "Functional map and domain structure of MET, the product of the c-met protooncogene and receptor for hepatocyte growth factor/scatter factor," Proc Natl Acad Sci USA 100(21):12039-44 (2003).

Gonzalez et al., "A full antagonist anti-c-Met Mab with in vivo activity," Int. J. Cancer 139:1851-1863 (2016).

Hultberg et al., "Depleting MET-Expressing Tumor Cells by ADCC Provides a Therapeutic Advantage over Inhibiting HGF/MET Signaling," Cancer Res 75(16): 3373-3383 (2015).

Karamouzis et al., "Targeting MET as a strategy to overcome crosstalk-related resistance to EGFR inhibitors," Lancet Oncol 10:709-717 (2009).

Kong-Beltran et al., "The Sema domain of Met is necessary for receptor dimerization," Cancer Cell 6(1):75-84 (2004).

Liu et al., "LY2875358, a neutralizing and internalizing anti-MET bivalent antibody, inhibits HGF-dependent and HGF-independent MET activation and tumor growth," Clin. Cancer. Res. 20(23):6059-70 (2014).

Merchant et al., "Monovalent antibody design and mechanism of action of onartuzumab, a MET antagonist with anti-tumor activity as a therapeutic agent," Proc Natl Acad Sci USA 110(32):E2987-96 (2013).

Sattler et al., "The role of the c-Met pathway in lung cancer and the potential for targeted therapy," Ther Adv Med Oncol. 3(4):171-84 (2011).

Stamos J. et al., "Crystal structure of the HGF beta-chain in complex with the Sema domain of the Met receptor," EMBO J. 23:2325-2335 (2004).

Van Der Horst et al., "Discovery of fully human anti-MET monoclonal antibodies with antitumor activity against colon cancer tumor models in vivo," Neoplasia 11(4): 355-364 (2009).

* cited by examiner

Chimeric 9338 VH + VL

9338 VH: QVQLQQPGAELAKPGASVRMSCKASGYTFTSYWMHWVKQRPGQGLEWIGYINPSSGHIENNQKFKDKATLTADKSSSTAYMQLSSLTFEDSAVYYCARGRFAYWGQGTLVTVSS

9338 VL: DIVMTQSPAIMSASPGEKVTLTCSASSSVSSGYLYWYQQKPGSSPKLWIYSTSNLASGVPARFSGSGSGTSYSLTVNSMEAEDAASYFCHQWSSYPFTFGSGTKLELK

ANTI-MET ANTIBODIES AND COMPOSITIONS

RELATED APPLICATIONS

This application is a national stage application under 37 U.S.C. § 371 of International Patent Application No. PCT/M2015/002110, filed on Sep. 15, 2015, which claims the benefit of U.S. provisional application 62/051,190, filed on Sep. 16, 2014. The disclosures of those applications are incorporated by reference herein in their entirety.

SEQUENCE LISTING

The instant application contains a Sequence Listing that has been submitted electronically in ASCII format and is hereby incorporated by reference in its entirety. The ASCII copy, created on Sep. 15, 2015, is named 110285-0051-WO1_SL.txt and is 78,490 bytes in size.

FIELD OF THE INVENTION

This invention relates to anti-MET antibodies and antibody compositions and methods of using them in treating diseases and conditions related to MET.

BACKGROUND OF THE INVENTION

MET (also known as c-MET) is a receptor tyrosine kinase comprising a 50 kDa α-subunit and a 145 kDa β-subunit. The only known ligand for MET is hepatocyte growth factor (HGF), which is also known as scatter factor. Binding of HGF to MET leads to receptor dimerization and autophosphorylation of β-subunit residues Y1349 and Y1356, activating downstream signaling pathways that include the phosphoinositol 3-kinase (PI3K)-protein kinase B (Akt) pathway, the signal transducer and activator of transcription factor (STAT) pathway, the mitogen-activated protein kinase (MAPK) pathway, and the nuclear factor kappa-light-chain-enhancer of activated B cells (NFκB) pathway. This ultimately leads to increased mitogenesis, cell proliferation, cell survival, and cell motility. Dysregulation of MET or HGF activity may occur, e.g., through overexpression, gene amplification, mutation, or alternative splicing of MET, or through HGF ligand-induced autocrine/paracrine loop signaling. Such dysregulation plays a role in many cancers by facilitating cancer invasiveness, angiogenesis, metastasis, and tumor growth, thus leading to a more aggressive cancer phenotype and a poorer prognosis.

MET is also known to interact with signaling pathways involving other receptors, such as EGFR, TGF-β, and HER3, and may play a role in resistance to treatments targeting those receptors. MET inhibitors, such as anti-MET antibodies, thus may be effective in combination with other receptor inhibitors in overcoming resistant phenotypes.

Current MET inhibitors include both monoclonal antibodies, which may target either MET or its ligand, HGF, and small molecule kinase inhibitors. Known antibodies targeting the MET pathway include the humanized anti-MET antibody onartuzumab (OA-5D5, OAM4558g, MetMAb); the humanized anti-HGF antibody ficlatuzumab (AV-299); the human anti-HGF antibody rilotumumab (AMG102); the humanized anti-HGF antibody TAK701; the humanized IgG4 anti-c-MET antibody LY2875358/LA480; the humanized anti-c-MET antibody ABT-700 (H224G11); and the ARGX-111 anti-c-MET antibody (36C4). Known anti-MET small molecule receptor tyrosine kinase inhibitors include tivantinib, cabozantinib, foretinib, golvatinib, and crizotinib. However, no anti-MET antibodies have been approved for therapeutic use.

In view of the critical role of MET in cancer progression, there is a need for new and improved therapies that target MET.

SUMMARY OF THE INVENTION

The present invention is directed to novel recombinant antibodies targeting MET, as well as compositions comprising two or more of these antibodies, and use of the antibodies and compositions for treatment of cancers including non-small cell lung cancer, gastric cancer, hepatocellular carcinoma, esophageal cancer, colorectal cancer, kidney papillary cell cancer, glioblastoma, adrenocortical carcinoma, renal cell carcinoma, prostate cancer, and other cancers that express or overexpress MET or rely on MET pathway activation. Compared to currently available treatments for such cancers, including antibody treatments, it is contemplated that the antibodies of the invention provide a superior clinical response either alone or in a composition comprising two or more such antibodies.

In one embodiment, the present invention provides an antibody composition comprising a first anti-MET antibody or an antigen-binding portion thereof and a second anti-MET antibody or an antigen-binding portion thereof.

In some embodiments, the first anti-MET antibody competes for binding to human MET with an antibody having an H-CDR1, H-CDR2, H-CDR3, L-CDR1, L-CDR2, and L-CDR3 comprising the amino acid sequences of SEQ ID NOs: 21, 22, 23, 24, 25, and 26, respectively, and the second anti-MET antibody competes for binding to human MET with an antibody having an H-CDR1, H-CDR2, H-CDR3, L-CDR1, L-CDR2, and L-CDR3 comprising the amino acid sequences of SEQ ID NOs: 27, 28, 29, 30, 31, and 32, respectively.

In some embodiments, the first anti-MET antibody binds to the same epitope of human MET as an antibody having an H-CDR1, H-CDR2, H-CDR3, L-CDR1, L-CDR2, and L-CDR3 comprising the amino acid sequences of SEQ ID NOs: 21, 22, 23, 24, 25, and 26, respectively, and the second anti-MET antibody binds to the same epitope of human MET as an antibody having an H-CDR1, H-CDR2, H-CDR3, L-CDR1, L-CDR2, and L-CDR3 comprising the amino acid sequences of SEQ ID NOs: 27, 28, 29, 30, 31, and 32, respectively. In some embodiments, the first MET antibody may bind SEMA-α blade 3, and the second MET antibody may bind SEMA-α blade 2. A combination of these antibodies target both epitopes and produce surprising synergistic inhibitory effects on MET signaling pathway. We have discovered that combined targeting of these epitopes produces surprisingly high inhibitory activity on the MET signaling pathway.

In some embodiments, the first anti-MET antibody comprises an H-CDR3 that comprises the amino acid sequence of SEQ ID NO: 23. In some embodiments, the first anti-MET antibody comprises an H-CDR1, H-DR2, and H-CDR3 that comprise the amino acid sequences of SEQ ID NOs: 21, 22, and 23, respectively. In some embodiments, the first anti-MET antibody comprises a heavy chain variable domain (VH) that is at least 90% identical in sequence to the amino acid sequence of SEQ ID NO: 6 or 14. In some embodiments, the first anti-MET antibody comprises a VH comprises the amino acid sequence of SEQ ID NO: 6 or 14. In some embodiments, the first anti-MET antibody comprises a heavy chain (HC) that comprises the amino acid sequence of SEQ ID NO: 34.

In some embodiments, the first anti-MET antibody comprises an L-CDR3 that comprises the amino acid sequence of SEQ ID NO: 26. In some embodiments, the first anti-MET antibody comprises an L-CDR1, L-CDR2, and L-CDR3 that comprise the amino acid sequences of SEQ ID NOs: 24, 25, and 26, respectively. In some embodiments, the first anti-MET antibody comprises a light chain variable domain (VL) that is at least 90% identical in sequence to the amino acid sequence of SEQ ID NO: 8 or 16. In some embodiments, the first anti-MET antibody comprises a VL that comprises the amino acid sequence of SEQ ID NO: 8 or 16. In some embodiments, the first anti-MET antibody comprises a light chain (LC) that comprises the amino acid sequence of SEQ ID NO: 33.

In some embodiments, the first anti-MET antibody comprises an H-CDR3 that comprises the amino acid sequence of SEQ ID NO: 23 and an L-CDR3 that comprises the amino acid sequence of SEQ ID NO: 26. In some embodiments, the first-anti-MET antibody comprises an H-CDR1, H-CDR2, H-CDR3, L-CDR1, L-CDR2, and L-CDR3 that comprise the amino acid sequences of SEQ ID NOs: 21, 22, 23, 24, 25, and 26, respectively. In some embodiments, the first anti-MET antibody comprises a VH that is at least 90% identical in sequence to the amino acid sequence of SEQ ID NO: 6 or 14 and a VL that is at least 90% identical in sequence to the amino acid sequence of SEQ ID NO: 8 or 16. In some embodiments, the first anti-MET antibody comprises a VH that comprises the amino acid sequence of SEQ ID NO: 6 or 14 and a VL that comprises the amino acid sequence of SEQ ID NO: 8 or 16. In some embodiments, the first anti-MET antibody comprises a VH that comprises the amino acid sequence of SEQ ID NO: 6 and a VL that comprises the amino acid sequence of SEQ ID NO: 8. In some embodiments, the first anti-MET antibody comprises a VH that comprises the amino acid sequence of SEQ ID NO: 14 and a VL that comprises the amino acid sequence of SEQ ID NO: 16. In some embodiments, the first anti-MET antibody comprises an HC that comprises the amino acid sequence of SEQ ID NO: 34 and an LC that comprises the amino acid sequence of SEQ ID NO: 33.

In some embodiments, the second anti-MET antibody comprises an H-CDR3 that comprises the amino acid sequence of SEQ ID NO: 29. In some embodiments, the second anti-MET antibody comprises an H-CDR1, H-CDR2, and H-CDR3 that comprise the amino acid sequences of SEQ ID NOs: 27, 28, and 29, respectively. In some embodiments, the second anti-MET antibody comprises a VH that is at least 90% identical in sequence to the amino acid sequence of SEQ ID NO: 10 or 18. In some embodiments, the second anti-MET antibody comprises a VH that comprises the amino acid sequence of SEQ ID NO: 10 or 18. In some embodiments, the second-anti-MET antibody comprises an HC that comprises the amino acid sequence of SEQ ID NO: 36.

In some embodiments, the second anti-MET antibody comprises an L-CDR3 that comprises the amino acid sequence of SEQ ID NO: 32. In some embodiments, the second anti-MET antibody comprises an L-CDR1, L-CDR2, and L-CDR3 that comprise the amino acid sequences of SEQ ID NOs: 30, 31, and 32, respectively. In some embodiments, the second anti-MET antibody comprises a VL that is at least 90% identical in sequence to the amino acid sequence of SEQ ID NO: 12 or 20. In some embodiments, the second anti-MET antibody comprises the amino acid sequence of SEQ ID NO: 12 or 20. In some embodiments, the second-anti-MET antibody comprises an LC that comprises the amino acid sequence of SEQ ID NO: 35.

In some embodiments, the second anti-MET antibody comprises an H-CDR3 that comprises the amino acid sequence of SEQ ID NO: 29 and an L-CDR3 that comprises the amino acid sequence of SEQ ID NO: 32. In some embodiments, the second anti-MET antibody comprises an H-CDR1, H-CDR2, H-CDR3, L-CDR1, L-CDR2, and L-CDR3 that comprise the amino acid sequences of SEQ ID NOs: 27, 28, 29, 30, 31, and 32, respectively. In some embodiments, the second anti-MET antibody comprises a VH that is at least 90% identical in sequence to the amino acid sequence of SEQ ID NO: 10 or 18 and a VL that is at least 90% identical in sequence to the amino acid sequence of SEQ ID NO: 12 or 20. In some embodiments, the second anti-MET antibody comprises a VH that comprises the amino acid sequence of SEQ ID NO: 10 or 18 and a VL that comprises the amino acid sequence of SEQ ID NO: 12 or 20. In some embodiments, the second anti-MET antibody comprises a VH that comprises the amino acid sequence of SEQ ID NO: 10 and a VL that comprises the amino acid sequence of SEQ ID NO: 12. In some embodiments, the second anti-MET antibody comprises a VH that comprises the amino acid sequence of SEQ ID NO: 18 and a VL that comprises the amino acid sequence of SEQ ID NO: 20. In some embodiments, the second anti-MET antibody comprises an HC that comprises the amino acid sequence of SEQ ID NO: 36 and an LC that comprises the amino acid sequence of SEQ ID NO: 35.

The present invention also provides antibody compositions comprising any combination of the first and second anti-MET antibodies described herein.

For example, in some embodiments, the first anti-MET antibody has an H-CDR3 and L-CDR3 comprising the amino acid sequences of SEQ ID NOs: 23 and 26, respectively, and the second anti-MET antibody has an H-CDR3 and L-CDR3 comprising the amino acid sequences of SEQ ID NOs: 29 and 32, respectively. In some embodiments, the first anti-MET antibody has an H-CDR1, H-CDR2, H-CDR3 and L-CDR1, L-CDR2, and L-CDR3 comprising the amino acid sequences of SEQ ID NOs: 21, 22, 23, 24, 25, and 26, respectively, and the second anti-MET antibody has an H-CDR1, H-CDR2, H-CDR3 and L-CDR1, L-CDR2, and L-CDR3 comprising the amino acid sequences of SEQ ID NOs: 27, 28, 29, 30, 31, and 32, respectively.

In some embodiments, the VH and VL of the first anti-MET antibody are at least 90% identical in sequence to the amino acid sequences of SEQ ID NOs: 6 and 8, respectively, and the VH and VL of the second anti-MET antibody are at least 90% identical in sequence to the amino acid sequences of SEQ ID NOs: 10 and 12, respectively. In some embodiments, the VH and VL of the first anti-MET antibody are at least 90% identical in sequence to the amino acid sequences of SEQ ID NOs: 14 and 16, respectively, and the VH and VL of the second anti-MET antibody are at least 90% identical in sequence to the amino acid sequences of SEQ ID NOs: 18 and 20, respectively. In some embodiments, the VH and VL of the first anti-MET antibody comprise the amino acid sequences of SEQ ID NOs: 6 and 8, respectively, and the VH and VL of the second anti-MET antibody comprise the amino acid sequences of SEQ ID NOs: 10 and 12, respectively. In some embodiments, the VH and VL of the first anti-MET antibody comprise the amino acid sequences of SEQ ID NOs: 14 and 16, respectively, and the VH and VL of the second anti-MET antibody comprise the amino acid sequences of SEQ ID NOs: 18 and 20, respectively. In some embodiments, the HC and LC of the first anti-MET antibody comprise the amino acid sequences of SEQ ID NOs: 34 and 33, respectively, and the HC and LC of the second anti-MET antibody comprise the amino acid sequences of SEQ ID NOs: 36 and 35, respectively.

In some embodiments of the anti-MET antibody compositions described herein, the first anti-MET antibody, the second anti-MET antibody, or both, are of isotype IgG. In certain embodiments, the first anti-MET antibody, the second anti-MET antibody, or both, are of isotype subclass IgG1.

In some embodiments, at least one, at least two, or all of the anti-MET antibodies in a composition described herein have at least one property, or any combination of properties, selected from the group consisting of:
 does not bind to mouse or chicken MET;
 binds to an epitope of human MET comprising residues that are present on the SEMA domain;
 induces degradation of MET;
 binds to human MET with a $K_D$ of $1 \times 10^{-9}$ M or less;
 inhibits growth in vitro of at least one cell line selected from SNU5, EBC1, MKN45, KatoII, OE33, and Okajima;
 inhibits MET phosphorylation;
 inhibits MET downstream signaling;
 inhibits primary endothelial cell proliferation in the presence or absence of HGF; and
 inhibits tumor growth in vivo.

In some embodiments, any of the anti-MET antibody compositions described herein has at least one property, or any combination of properties, selected from the group consisting of:
 induces degradation of MET;
 inhibits growth in vitro of at least one cell line selected from SNU5, EBC1, MKN45, KatoII, OE33, and Okajima;
 inhibits MET phosphorylation;
 inhibits MET downstream signaling;
 inhibits primary endothelial cell proliferation in the presence or absence of HGF; and
 inhibits tumor growth in vivo.

The present invention also provides a pharmaceutical composition comprising any of the anti-MET antibody compositions described herein and a pharmaceutically acceptable excipient.

The present invention also provides an anti-MET antibody or an antigen-binding portion thereof. In some embodiments, the antibody or portion competes for binding to human MET with an antibody whose H-CDR1, H-CDR2, H-CDR3, L-CDR1, L-CDR2, and L-CDR3 comprise the amino acid sequences of SEQ ID NOs: 21, 22, 23, 24, 25, and 26, respectively. In some embodiments, the antibody or portion competes for binding to human MET with an antibody whose H-CDR1, H-CDR2, H-CDR3, L-CDR1, L-CDR2, and L-CDR3 comprise the amino acid sequences of SEQ ID NOs: 27, 28, 29, 30, 31, and 32, respectively.

In some embodiments, the antibody or portion binds to the same epitope of human MET as an antibody whose H-CDR1, H-CDR2, H-CDR3, L-CDR1, L-CDR2, and L-CDR3 comprise the amino acid sequences of SEQ ID NOs: 21, 22, 23, 24, 25, and 26, respectively. In some embodiments, the antibody or portion binds to the same epitope of human MET as an antibody whose H-CDR1, H-CDR2, H-CDR3, L-CDR1, L-CDR2, and L-CDR3 comprise the amino acid sequences of SEQ ID NOs: 27, 28, 29, 30, 31, and 32, respectively.

In some embodiments, the antibody comprises an H-CDR3 comprising the amino acid sequence of SEQ ID NO: 23 and/or an L-CDR3 comprising the amino acid sequence of SEQ ID NO: 26, an H-CDR1, H-CDR2, and H-CDR3 comprising the amino acid sequences of SEQ ID NOs: 21, 22, and 23, respectively and/or an L-CDR1, L-CDR2, and L-CDR3 comprising the amino acid sequences of SEQ ID NOs: 24, 25, and 26, respectively, a VH with at least 90% sequence identity to the amino acid sequence of SEQ ID NO: 6 or 14 and/or a VL with at least 90% sequence identity to the amino acid sequence of SEQ ID NO: 8 or 16; or a VH comprising the amino acid sequence of SEQ ID NO: 6 or 14 and/or a VL comprising the amino acid sequence of SEQ ID NO: 8 or 16. In certain embodiments, the antibody comprises a VH comprising the amino acid sequence of SEQ ID NO: 6 and a VL comprising the amino acid sequence of SEQ ID NO: 8. In certain embodiments, the antibody comprises a VH comprising the amino acid sequence of SEQ ID NO: 14 and a VL comprising the amino acid sequence of SEQ ID NO: 16. In certain embodiments, the antibody comprises an HC comprising the amino acid sequence of SEQ ID NO: 34 and an LC comprising the amino acid sequence of SEQ ID NO: 33.

In some embodiments, the antibody comprises a heavy chain that comprises an H-CDR3 comprising the amino acid sequence of SEQ ID NO: 23; an H-CDR1, H-CDR2, and H-CDR3 comprising the amino acid sequences of SEQ ID NOs: 21, 22, and 23, respectively; a VH with at least 90% sequence identity to the amino acid sequence of SEQ ID NO: 6 or 14; a VH comprising the amino acid sequence of SEQ ID NO: 6 or 14; or an HC comprising the amino acid sequence of SEQ ID NO: 34; and further comprises a light chain that comprises an L-CDR3 comprising the amino acid sequence of SEQ ID NO: 26; an L-CDR1, L-CDR2, and L-CDR3 comprising the amino acid sequences of SEQ ID NOs: 24, 25, and 26, respectively; a VL with at least 90% sequence identity to the amino acid sequence of SEQ ID NO: 8 or 16; a VL comprising the amino acid sequence of SEQ ID NO: 8 or 16; or an LC comprising the amino acid sequence of SEQ ID NO: 33.

In some embodiments, the antibody comprises an H-CDR3 comprising the amino acid sequence of SEQ ID NO: 29 and/or an L-CDR3 comprising the amino acid sequence of SEQ ID NO: 32; an H-CDR1, H-CDR2, and H-CDR3 comprising the amino acid sequences of SEQ ID NOs: 27, 28, and 29, respectively and/or an L-CDR1, L-CDR2, and L-CDR3 comprising the amino acid sequences of SEQ ID NOs: 30, 31, and 32, respectively; a VH with at least 90% sequence identity to the amino acid sequence of SEQ ID NO: 10 or 18; and/or a VL with at least 90% sequence identity to the amino acid sequence of SEQ ID NO: 12 or 20; or a VH comprising the amino acid sequence of SEQ ID NO: 10 or 18 and/or a VL comprising the amino acid sequence of SEQ ID NO: 12 or 20. In certain embodiments, the antibody comprises a VH comprising the amino acid sequence of SEQ ID NO: 10 and a VL comprising the amino acid sequence of SEQ ID NO: 12. In certain embodiments, the antibody comprises a VH comprising the amino acid sequence of SEQ ID NO: 18 and a VL comprising the amino acid sequence of SEQ ID NO: 20. In certain embodiments, the antibody comprises an HC comprising the amino acid sequence of SEQ ID NO: 36 and an LC comprising the amino acid sequence of SEQ ID NO: 35.

In some embodiments, the antibody comprises a heavy chain that comprises an H-CDR3 comprising the amino acid sequence of SEQ ID NO: 29; an H-CDR1, H-CDR2, and H-CDR3 comprising the amino acid sequences of SEQ ID NOs: 27, 28, and 29, respectively; a VH with at least 90% sequence identity to the amino acid sequence of SEQ ID NO: 10 or 18; a VH comprising the amino acid sequence of SEQ ID NO: 10 or 18; or an HC comprising the amino acid sequence of SEQ ID NO: 36; and further comprises a light chain that comprises an L-CDR3 comprising the amino acid sequence of SEQ ID NO: 32; an L-CDR1, L-CDR2, and L-CDR3 comprising the amino acid sequences of SEQ ID NOs: 30, 31, and 32, respectively; a VL with at least 90% sequence identity to the amino acid sequence of SEQ ID NO: 12 or 20; a VL comprising the amino acid sequence of SEQ ID NO: 12 or 20; or an LC comprising the amino acid sequence of SEQ ID NO: 35.

In some embodiments, the antibody has an H-CDR1, H-CDR2, H-CDR3, L-CDR1, L-CDR2, and L-CDR3 comprising the amino acid sequences of SEQ ID NOs: 21, 22, 23, 24, 25, and 26, respectively.

In some embodiments, the antibody has an H-CDR1, H-CDR2, H-CDR3, L-CDR1, L-CDR2, and L-CDR3 comprising the amino acid sequences of SEQ ID NOs: 27, 28, 29, 30, 31, and 32, respectively.

In some embodiments, the antibody has a heavy chain variable domain (VH) with at least 90% sequence identity to the amino acid sequence of SEQ ID NO: 6 or 14 and a light chain variable domain (VL) with at least 90% sequence identity to the amino acid sequence of SEQ ID NO: 8 or 16.

In some embodiments, the antibody has a heavy chain variable domain (VH) with at least 90% sequence identity to the amino acid sequence of SEQ ID NO: 10 or 18 and a light chain variable domain (VL) with at least 90% sequence identity to the amino acid sequence of SEQ ID NO: 12 or 20.

In some embodiments, the antibody has a heavy chain variable domain (VH) comprising the amino acid sequence of SEQ ID NO: 6 and a light chain variable domain (VL) comprising the amino acid sequence of SEQ ID NO: 8.

In some embodiments, the antibody has a heavy chain variable domain (VH) comprising the amino acid sequence of SEQ ID NO: 10 and a light chain variable domain (VL) comprising the amino acid sequence of SEQ ID NO: 12.

In some embodiments, the antibody has a heavy chain variable domain (VH) comprising the amino acid sequence of SEQ ID NO: 14 and a light chain variable domain (VL) comprising the amino acid sequence of SEQ ID NO: 16.

In some embodiments, the antibody has a heavy chain variable domain (VH) comprising the amino acid sequence of SEQ ID NO: 18 and a light chain variable domain (VL) comprising the amino acid sequence of SEQ ID NO: 20.

In some embodiments, the antibody has a heavy chain (HC) comprising the amino acid sequence of SEQ ID NO: 34 and a light chain (LC) comprising the amino acid sequence of SEQ ID NO: 33.

In some embodiments, the antibody has a heavy chain (HC) comprising the amino acid sequence of SEQ ID NO: 36 and a light chain (LC) comprising the amino acid sequence of SEQ ID NO: 35.

The invention also provides humanized versions of chimeric antibodies and antigen-binding portions described herein, particularly antibodies and antigen-binding portions with heavy and light chain amino acid sequences relating to SEQ ID NOs: 6 and 8, respectively, or SEQ ID NOs: 10 and 12, respectively.

In some embodiments of the antibodies and antigen-binding portions described herein, the antibody may be of isotype IgG. In certain embodiments, the antibody is of isotype subclass IgG1.

In some embodiments, the antibody has at least one property, or any combination of properties, selected from the group consisting of:

does not bind to mouse or chicken MET;
binds to an epitope of human MET comprising residues that are present on the SEMA domain;
induces degradation of MET;
binds to human MET with a $K_D$ of $1\times10^{-9}$ M or less;
inhibits growth in vitro of at least one cell line selected from SNU5, EBC1, MKN45, KatoII, OE33, and Okajima;
inhibits MET phosphorylation;
inhibits MET downstream signaling;
inhibits primary endothelial cell proliferation in the presence or absence of HGF; and
inhibits tumor growth in vivo.

The present invention also provides a pharmaceutical composition comprising any of the anti-MET antibodies or antigen-binding portions thereof described herein and a pharmaceutically acceptable excipient.

The present invention provides an isolated nucleic acid molecule comprising a nucleotide sequence that encodes the heavy chain or an antigen-binding portion thereof, a nucleotide sequence that encodes the light chain or an antigen-binding portion thereof, or both, of an anti-MET antibody described herein. In some embodiments, the isolated nucleic acid molecule comprises a nucleotide sequence selected from the group consisting of SEQ ID NOs: 5, 7, 9, 11, 13, 15, 17, or 19.

The present invention also provides a vector comprising the isolated nucleic acid molecule, wherein said vector further comprises an expression control sequence.

The present invention also provides a host cell comprising a nucleotide sequence that encodes the heavy chain or an antigen-binding portion thereof, a nucleotide sequence that encodes the light chain or an antigen-binding portion thereof, or both, of an anti-MET antibody described herein. In some embodiments, the host cell comprises a nucleotide sequence selected from the group consisting of SEQ ID NOs: 5, 7, 9, 11, 13, 15, 17, or 19.

The present invention also provides a non-human transgenic animal or plant comprising a nucleotide sequence that encodes the heavy chain or an antigen-binding portion thereof, a nucleotide sequence that encodes the light chain or an antigen-binding portion thereof, or both, of an anti-MET antibody described herein, wherein said animal or plant expresses the nucleotide sequence(s). In some embodiments, the animal or plant comprises a nucleotide sequence selected from the group consisting of SEQ ID NOs: 5, 7, 9, 11, 13, 15, 17, or 19.

The present invention also provides a method for producing an anti-MET antibody or antigen-binding portion thereof described herein, comprising providing the above-described host cell, cultivating said host cell under conditions suitable for expression of the antibody or portion, and isolating the resulting antibody or portion.

The present invention also provides a method for producing an anti-MET antibody composition described herein, comprising providing a first host cell capable of expressing a first anti-MET antibody or antigen-binding portion as described herein and a second host cell capable of expressing a second anti-MET antibody or antigen-binding portion as described herein, cultivating said first and second host cells under conditions suitable for expression of the antibodies or portions, and isolating the resulting antibodies or portions. In certain embodiments, the first and second host cells are cultured in a single bioreactor. In other embodiments, the first and second host cells are cultured in separate bioreactors.

The present invention also provides a polyclonal cell line capable of expressing an anti-MET antibody composition, wherein said polyclonal cell line comprises a first host cell capable of expressing a first anti-MET antibody or antigen-binding portion thereof as described herein and a second host cell capable of expressing a second anti-MET antibody or antigen-binding portion thereof as described herein.

The present invention also provides a bispecific binding molecule having the binding specificities of the first and second anti-MET antibodies or antigen-binding portions thereof of an anti-MET antibody composition described herein. In certain embodiments, the bispecific binding molecule comprises an antigen-binding portion of an antibody whose H-CDR1, H-CDR2, H-CDR3, L-CDR1, L-CDR2, and L-CDR3 comprise the amino acid sequences of SEQ ID NOs: 21, 22, 23, 24, 25, and 26, respectively; and an antigen-binding portion of an antibody whose H-CDR1, H-CDR2, H-CDR3, L-CDR1, L-CDR2, and L-CDR3 comprise the amino acid sequences of SEQ ID NOs: 27, 28, 29, 30, 31, and 32, respectively.

The present invention also provides a method for treating a patient with a MET-mediated disorder, comprising administering to said patient an anti-MET antibody composition as described herein or a pharmaceutical composition comprising the anti-MET antibody composition.

The present invention also provides a method for treating a patient with a MET-mediated disorder, comprising administering to said patient an anti-MET antibody or antigen-binding portion as described herein or a pharmaceutical composition comprising the anti-MET antibody or antigen-binding portion.

The present invention also provides a method for treating a patient with cancer, comprising administering to said patient an anti-MET antibody composition as described herein or a pharmaceutical composition comprising the anti-MET antibody composition. In some embodiments, the cancer is dependent on MET activation. In certain embodiments, the cancer is non-small cell lung cancer, gastric cancer, hepatocellular carcinoma, esophageal cancer, colorectal cancer, kidney papillary cell cancer, glioblastoma, renal cell carcinoma, prostate cancer, or adrenocortical carcinoma.

The present invention also provides a method for treating a patient with cancer, comprising administering to said patient an anti-MET antibody or antigen-binding portion as described herein or a pharmaceutical composition comprising the anti-MET antibody or antigen-binding portion. Further, the present invention provides uses of an anti-MET antibody or antigen-binding portion as described herein or a pharmaceutical composition comprising the anti-MET antibody or antigen-binding portion in the manufacture of a medicament for treating cancer. Still further, the present invention provides an anti-MET antibody or antigen-binding portion as described herein or a pharmaceutical composition comprising the anti-MET antibody or antigen-binding portion for use in treating cancer. In some embodiments, the cancer is dependent on MET activation. In certain embodiments, the cancer is non-small cell lung cancer, gastric cancer, hepatocellular carcinoma, esophageal cancer, colorectal cancer, kidney papillary cell cancer, glioblastoma, renal cell carcinoma, prostate cancer, or adrenocortical carcinoma. In certain embodiments, the treatment also comprises administration of a chemotherapeutic agent, anti-neoplastic agent, anti-angiogenic agent, tyrosine kinase inhibitor, or another MET pathway inhibitor.

In some of embodiments of the methods of treatment described herein, the patient is a mammal. In certain embodiments, the patient is a primate. In particular embodiments, the patient is a human.

BRIEF DESCRIPTION OF THE DRAWINGS

FIG. 2 shows a summary of the binding of MET antibodies to different human, mouse, chicken and chimeric MET constructs expressed on HEK293 cells. The amino acid sequence numbers (AA) refer to the human MET sequence that was exchanged to either chicken or mouse. Schematic illustrations of the different constructs are shown. The individual domains or subdomains are indicated. SP: Signal Peptide. SV5-GPI: SV5 peptide sequence followed by Glycine-Serine linker and GPI anchor. Note the illustration of the location of mutations is approximate. White squares: Human MET sequence. Grey squares: Chicken sequence. Hatched squares: Mouse sequence. Positive binding to transfected cells is indicated as +. Weak binding as (+). No binding as −.

Figure 26:
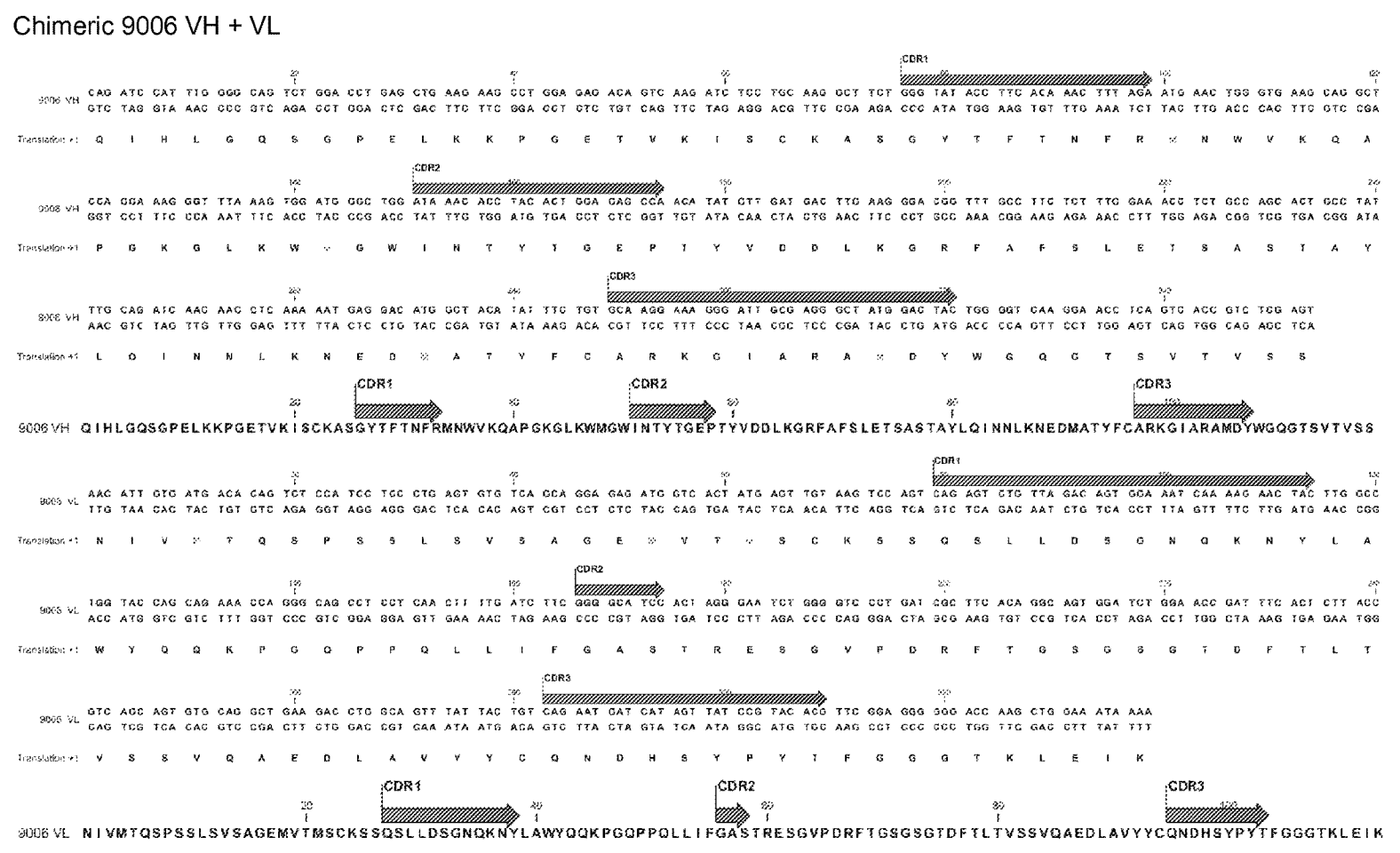

FIG. 26 shows the heavy and light chain variable domain nucleotide and amino acid sequences of the chimeric 9006 antibody (SEQ ID NOs: 5-8). The CDRs (SEQ ID NOs: 21-26) are marked by arrows.

FIG. 27 shows the heavy and light chain variable domain nucleotide and amino acid sequences of the chimeric 9338 antibody (SEQ ID NOs: 9-12). The CDRs (SEQ ID NOs: 27-32) are marked by arrows.

FIG. 28 shows the heavy and light chain variable domain nucleotide and amino acid sequences of the humanized 9006 antibody (SEQ ID NOs: 13-16). The CDRs are marked by arrows (SEQ ID NOs: 21-26).

FIG. 29 shows the heavy and light chain variable domain nucleotide and amino acid sequences of the humanized 9338 antibody (SEQ ID NOs: 17-20). The CDRs (SEQ ID NOs: 27-32) are marked by arrows.

DETAILED DESCRIPTION OF THE INVENTION

Definitions and General Techniques

Figure 1:
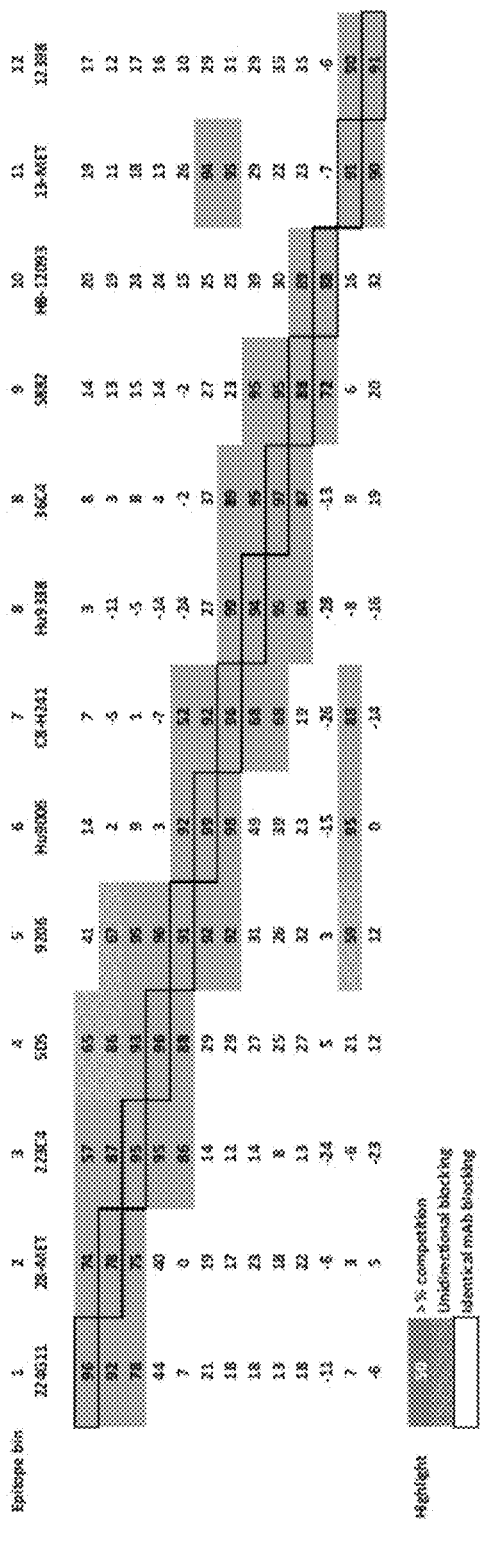
FIG. 1 shows a competition matrix for thirteen MET antibodies tested against each other. An inhibition of at least 50% was used for differentiating epitope bins (gray squares). Dotted squares: Unidirectional competition. Black framed squares: Competition with identical antibody.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art.

Further, unless otherwise required by context, singular terms shall include pluralities and plural terms shall include the singular. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well known and commonly used in the art. Enzymatic reactions and purification techniques are performed according to manufacturer's specifications, as commonly accomplished in the art or as described herein.

Throughout this specification and embodiments, the words "have" and "comprise," or variations such as "has," "having," "comprises," or "comprising," will be understood to imply the inclusion of a stated integer or group of integers but not the exclusion of any other integer or group of integers.

Antibody-Related Definitions

Unless otherwise stated, as used herein, "MET" refers to human MET (otherwise known as human c-MET). A human MET polypeptide sequence is available under NCBI Accession No. NM_000245.2, shown here as SEQ ID NO: 1. Unless otherwise specified, "human MET" refers to the amino acid sequence of SEQ ID NO: 1. Human MET also exists in a different isoform (isoform 2; SEQ ID NO: 2) in which 19 amino acids are inserted in IPT domain 3 (755-755: S→STWWKEPLNIVSFLFCFAS (SEQ ID NO: 2)).

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acids to each region may be in accordance with IMGT® definitions (Lefranc et al., *Dev Comp Immunol* 27(1):55-77 (2003); or the definitions of Kabat, *Sequences of Proteins of Immunological Interest* (National Institutes of Health, Bethesda, Md. (1987 and 1991)); Chothia & Lesk, *J. Mol. Biol.* 196:901-917 (1987); or Chothia et al., *Nature* 342:878-883 (1989).

The term "recombinant antibody" refers to an antibody that is expressed from a cell or cell line comprising the nucleotide sequence(s) that encode the antibody, wherein said nucleotide sequence(s) are not naturally associated with the cell.

The term "antibody composition" refers to a combination of two or more antibodies or antigen-binding portions thereof. An antibody composition may be monoclonal (i.e., consisting of identical antibody or antigen-binding portion molecules) or polyclonal (i.e., consisting of two or more different antibodies or antigen-binding portions reacting with the same or different epitopes on the same antigen or even on distinct, different antigens).

The term "isolated protein", "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

As used herein, the term "germline" refers to the nucleotide and amino acid sequences of antibody genes and gene segments as they are passed from parents to offspring via germ cells. Germline sequences are distinguished from the nucleotide sequences encoding antibodies in mature B cells, which have been altered by recombination and hypermutation events during the course of B cell maturation. An antibody that "utilizes" a particular germline sequence has a nucleotide or amino acid sequence that aligns with that germline nucleotide sequence or with the amino acid sequence that it specifies more closely than with any other germline nucleotide or amino acid sequence.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ is ≤1 mM, preferably ≤100 nM. A $K_D$ binding affinity constant can be measured, e.g., by surface plasmon resonance (BIAcore™) or Bio-Layer Interferometry, for example using the Octet™ system.

The term "$k_{off}$" refers to the dissociation rate constant of a particular antibody-antigen interaction. A $k_{off}$ dissociation rate constant can be measured by Bio-Layer Interferometry, for example using the Octet™ system or by surface plasmon resonance (BIAcore™).

The term "epitope" as used herein refers to a portion (determinant) of an antigen that specifically binds to an antibody or a related molecule such as a bispecific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. Further, the generation and characterization of antibodies may elucidate information about desirable epitopes. From this information, it is then possible to competitively screen antibodies for binding to the same or similar epitopes, e.g., by conducting competition studies to find antibodies compete for binding to the antigen.

One can determine whether an antibody binds to the same epitope or cross competes for binding with an anti-MET antibody by using methods known in the art. In one embodiment, one allows the anti-MET antibody of the invention to bind to MET under saturating conditions and then measures the ability of the test antibody to bind to MET. If the test antibody is able to bind to MET at the same time as the reference anti-MET antibody, then the test antibody binds to a different epitope than the reference anti-MET antibody. However, if the test antibody is not able to bind to MET at the same time, then the test antibody binds to the same epitope, an overlapping epitope, or an epitope that is in close proximity to the epitope bound by the anti-MET antibody of the invention. This experiment can be performed using ELISA, RIA, BIACORE™, Bio-Layer Interferometry or flow cytometry. To test whether an anti-MET antibody cross-competes with another anti-MET antibody, one may use the competition method described above in two directions, i.e., determining if the known antibody blocks the test antibody and vice versa. In a preferred embodiment, the experiment is performed using Octet™.

The term "chimeric antibody" refers in its broadest sense to an antibody that contains one or more regions from one antibody and one or more regions from one or more other antibodies, typically an antibody that is partially of human origin and partially of non-human origin, i.e., derived in part from a non-human animal, for example a mouse, rat or other rodent, or an avian such as a chicken. Chimeric antibodies are preferred over non-human antibodies in order to reduce the risk of a human anti-antibody response, e.g., a human anti-mouse antibody response in the case of a murine antibody. An example of a typical chimeric antibody is one in which the variable region sequences are murine while the constant region sequences are human. In the case of a chimeric antibody, the non-human parts may be subjected to further alteration in order to humanize the antibody. The chimeric antibodies described herein have murine variable domain sequences and human constant domain sequences.

The term "humanize" refers to the fact that where an antibody is wholly or partially of non-human origin, for example a murine antibody obtained from immunization of mice with an antigen of interest or a chimeric antibody based on such a murine antibody, it is possible to replace certain amino acids, in particular in the framework regions and constant domains of the heavy and light chains, in order to avoid or minimize an immune response in humans. The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, e.g., by constructing expression vectors that express CDR sequences from the specific antibody grafted into framework sequences from a different antibody. As a result, it is possible to "humanize" a non-human antibody and still substantially maintain the binding specificity and affinity of the original antibody. Although it is not possible to precisely predict the immunogenicity and thereby the human anti-antibody response of a particular antibody, non-human antibodies tend to be more immunogenic than human antibodies. Chimeric antibodies, where the foreign (usually rodent) constant regions have been replaced with sequences of human origin, have been shown to be generally less immunogenic than antibodies of fully foreign origin, and the trend in therapeutic antibodies is towards humanized or fully human antibodies. Chimeric antibodies or other antibodies of non-human origin thus can be humanized to reduce the risk of a human anti-antibody response.

For chimeric antibodies, humanization typically involves modification of the framework regions of the variable region sequences. Amino acid residues that are part of complementarity determining regions (CDRs) most often will not be altered in connection with humanization, although in certain cases it may be desirable to alter individual CDR amino acid residues, for example to remove a glycosylation site, a deamidation site, an aspartate isomerization site or an undesired cysteine or methionine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues.

Numerous methods for humanization of an antibody sequence are known in the art; see e.g., the review by Almagro & Fransson, *Front Biosci.* 13:1619-1633 (2008). One commonly used method is CDR grafting, which for e.g., a murine-derived chimeric antibody involves identification of human germline gene counterparts to the murine variable region genes and grafting of the murine CDR sequences into this framework. CDR grafting may be based on the Kabat CDR definitions, although a more recent publication (Magdelaine-Beuzelin et al., *Crit Rev. Oncol Hematol.* 64:210-225 (2007)) has suggested that the IMGT® definition (the international ImMunoGeneTics information System®) may improve the result of the humanization (see Lefranc et al., *Dev. Comp Immunol.* 27:55-77 (2003)). In some cases, CDR grafting may reduce the binding specificity and affinity, and thus the biological activity, of a CDR-grafted non-human antibody as compared to the parenet antibody from which the CDRs are obtained. Back mutations (sometimes referred to as "framework repair") may be introduced at selected positions of the CDR-grafted antibody, typically in the framework regions, in order to reestablish the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., *Proc Natl Acad Sci USA*, 94:412-417 (1997), and the stepwise in vitro affinity maturation method of Wu et al. *Proc Natl Acad Sci USA* 95:6037-6042 (1998).

The term "antigen-binding portion" of an antibody (or simply "antibody portion"), as used herein, refers to one or more portions or fragments of an antibody that retain the ability to specifically bind to an antigen (e.g., human MET, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the $V_L$, $V_H$, $C_L$ and $C_H1$ domains; (ii) a F(ab')$_2$ fragment: a bivalent fragment comprising two Fab fragments linked by a disulfide bridge at the hinge region; (iii) an Fd fragment consisting of the $V_H$ and $C_H1$ domains; (iv) a Fv fragment consisting of the $V_L$ and $V_H$ domains of a single arm of an antibody, (v) a dAb fragment, which consists of a $V_H$ domain; and (vi) an isolated complementarity determining region (CDR) capable of specifically binding to an antigen. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv (scFv)). Also within the invention are antigen-binding molecules comprising a $V_H$ and/or a $V_L$, In the case of a $V_H$, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')$_2$ fragments, can be prepared from whole antibodies using conventional techniques, such as papain or pepsin digestion of whole antibodies. Moreover, antibodies, antibody portions and immunoadhesion molecules can be obtained using standard recombinant DNA techniques, e.g., as described herein.

In one embodiment, the antibody of the invention is a monoclonal antibody. As used herein, the acronym "mAb" refers to a monoclonal antibody, i.e., an antibody synthesized and secreted by an individual clonal population of cells. The clonal population can be a clonal population of immortalized cells. In some embodiments, the immortalized cells in the clonal population are hybrid cells—hybridomas—typically produced by the fusion of individual B lymphocytes from an immunized animal with individual cells from a lymphocytic tumour.

The class (isotype) and subclass of anti-MET antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various classes and subclasses of immunoglobulins, and determining the class and subclass of the antibodies.

Anti-MET Antibodies

The present invention relates to an antibody directed against human MET, or an antigen-binding portion of said antibody. The invention provides novel anti-MET antibodies 9006 and 9338 in both chimeric and humanized forms. FIGS. 26-30 depict the full-length (HC and LC) and variable domain (VH and VL) heavy and light chain nucleotide and amino acid sequences of these antibodies. Table 1 below provides the SEQ ID NOs of these sequences. Table 2 below provides the SEQ ID NOs for the heavy and light chain CDR amino acid sequences of antibodies 9006 and 9338 (which are the same between the chimeric and humanized forms). The CDR sequences were assigned in accordance with IMGT® definitions.

TABLE 2

SEQ ID NOs for the amino acid sequences of the CDRs of antibodies 9006 and 9338

|      | H-CDR1 | H-CDR2 | H-CDR3 | L-CDR1 | L-CDR2 | L-CDR3 |
|------|--------|--------|--------|--------|--------|--------|
| 9006 | 21     | 22     | 23     | 24     | 25     | 26     |
| 9338 | 27     | 28     | 29     | 30     | 31     | 32     |

In certain embodiments, the invention provides:

an anti-MET antibody or an antigen-binding portion thereof that competes for binding to human MET with an antibody having an H-CDR1, H-CDR2, H-CDR3, L-CDR1, L-CDR2, and L-CDR3 that comprise the amino acid sequences of SEQ ID NOs: 21, 22, 23, 24, 25, and 26, respectively;

an anti-MET antibody or an antigen-binding portion thereof that binds to the same epitope of human MET as an antibody having an H-CDR1, H-CDR2, H-CDR3, L-CDR1, L-CDR2, and L-CDR3 that comprise the amino acid sequences of SEQ ID NOs: 21, 22, 23, 24, 25, and 26, respectively;

an anti-MET antibody or an antigen-binding portion thereof that competes for binding to human MET with an antibody having a heavy chain variable domain comprising the amino acid sequence of SEQ ID NO: 6 and a light chain variable domain comprising the amino acid sequence of SEQ ID NO: 8;

an anti-MET antibody or an antigen-binding portion thereof that competes for binding to human MET with an antibody having a heavy chain variable domain comprising the amino acid sequence of SEQ ID NO: 14 and a light chain variable domain comprising the amino acid sequence of SEQ ID NO: 16;

an anti-MET antibody or an antigen-binding portion thereof that binds to the same epitope of human MET as an antibody having a heavy chain variable domain comprising the amino acid sequence of SEQ ID NO: 6 and a light chain variable domain comprising the amino acid sequence of SEQ ID NO: 8;

an anti-MET antibody or an antigen-binding portion thereof that binds to the same epitope of human MET as an antibody having a heavy chain variable domain comprising the amino acid sequence of SEQ ID NO: 14 and a light chain variable domain comprising the amino acid sequence of SEQ ID NO: 16;

an anti-MET antibody or an antigen-binding portion thereof that competes for binding to human MET with an antibody having an H-CDR1, H-CDR2, H-CDR3, L-CDR1, L-CDR2, and L-CDR3 that comprise the amino acid sequences of SEQ ID NOs: 27, 28, 29, 30, 31, and 32, respectively;

TABLE 1

SEQ ID NOs for the nucleotide and amino acid sequences of the heavy and light chain variable domains of antibodies 9006 and 9338

|      | chimeric | | | | humanized | | | | | |
|------|----|----|----|----|----|----|----|----|----|----|
|      | VH | | VL | | VH | | VL | | HC | LC |
|      | DNA | protein | DNA | protein | DNA | protein | DNA | protein | protein | protein |
| 9006 | 5 | 6 | 7 | 8 | 13 | 14 | 15 | 16 | 34 | 33 |
| 9338 | 9 | 10 | 11 | 12 | 17 | 18 | 19 | 20 | 36 | 35 | an anti-MET antibody or an antigen-binding portion thereof that binds to the same epitope of human MET as an antibody having an H-CDR1, H-CDR2, H-CDR3, L-CDR1, L-CDR2, and L-CDR3 that comprise the amino acid sequences of SEQ ID NOs: 27, 28, 29, 30, 31, and 32, respectively;

an anti-MET antibody or an antigen-binding portion thereof that competes for binding to human MET with an antibody having a heavy chain variable domain comprising the amino acid sequence of SEQ ID NO: 10 and a light chain variable domain comprising the amino acid sequence of SEQ ID NO: 12;

an anti-MET antibody or an antigen-binding portion thereof that competes for binding to human MET with an antibody having a heavy chain variable domain comprising the amino acid sequence of SEQ ID NO: 18 and a light chain variable domain comprising the amino acid sequence of SEQ ID NO: 20;

an anti-MET antibody or an antigen-binding portion thereof that binds to the same epitope of human MET as an antibody having a heavy chain variable domain comprising the amino acid sequence of SEQ ID NO: 10 and a light chain variable domain comprising the amino acid sequence of SEQ ID NO: 12;

an anti-MET antibody or an antigen-binding portion thereof that binds to the same epitope of human MET as an antibody having a heavy chain variable domain comprising the amino acid sequence of SEQ ID NO: 18 and a light chain variable domain comprising the amino acid sequence of SEQ ID NO: 20;

an anti-MET antibody or an antigen-binding portion thereof that competes for binding to human MET with an antibody having a heavy chain comprising the amino acid sequence of SEQ ID NO: 34 and a light chain comprising the amino acid sequence of SEQ ID NO: 33;

an anti-MET antibody or an antigen-binding portion thereof that competes for binding to human MET with an antibody having a heavy chain comprising the amino acid sequence of SEQ ID NO: 36 and a light chain comprising the amino acid sequence of SEQ ID NO: 35;

an anti-MET antibody or an antigen-binding portion thereof that binds to the same epitope of human MET as an antibody having a heavy chain comprising the amino acid sequence of SEQ ID NO: 34 and a light chain comprising the amino acid sequence of SEQ ID NO: 33; and an anti-MET antibody or an antigen-binding portion thereof that binds to the same epitope of human MET as an antibody having a heavy chain comprising the amino acid sequence of SEQ ID NO: 36 and a light chain comprising the amino acid sequence of SEQ ID NO: 35.

In one embodiment, the invention provides an anti-MET antibody or antigen-binding portion thereof having an H-CDR3 comprising the amino acid sequence of SEQ ID NO: 23 or 29. In one embodiment, the invention provides an anti-MET antibody or antigen-binding portion thereof having an L-CDR3 comprising the amino acid sequence of SEQ ID NO: 26 or 32. In one embodiment, the anti-MET antibody or antigen-binding portion thereof has an H-CDR3 comprising the amino acid sequence of SEQ ID NO: 23 or 29 and an L-CDR3 comprising the amino acid sequence of SEQ ID NO: 26 or 32. In certain embodiments, the anti-MET antibody or antigen-binding portion thereof comprises:

the H-CDR3 sequence of SEQ ID NO: 23 and the L-CDR3 sequence of SEQ ID NO: 26; or the H-CDR3 sequence of SEQ ID NO: 29 and the L-CDR3 sequence of SEQ ID NO: 32.

In one embodiment, the anti-MET antibody or antigen-binding portion thereof comprises:

an H-CDR1, H-CDR2, and H-CDR3 comprising the amino acid sequences of SEQ ID NOS: 21, 22, and 23, respectively; or an H-CDR1, H-CDR2, and H-CDR3 comprising the amino acid sequences of SEQ ID NOS: 27, 28, and 29, respectively.

In one embodiment, the anti-MET antibody or antigen-binding portion thereof comprises:

an L-CDR1, L-CDR2, and L-CDR3 comprising the amino acid sequences of SEQ ID NOS: 24, 25, and 26, respectively; or an L-CDR1, L-CDR2, and L-CDR3 comprising the amino acid sequences of SEQ ID NOS: 30, 31, and 32, respectively.

In one embodiment, the anti-MET antibody or antigen-binding portion thereof comprises:

an H-CDR1, H-CDR2, and H-CDR3 comprising the amino acid sequences of SEQ ID NOs: 21, 22, and 23, respectively, and an L-CDR1, L-CDR2, and L-CDR3 comprising the amino acid sequences of SEQ ID NOS: 24, 25, and 26, respectively; or an H-CDR1, H-CDR2, and H-CDR3 comprising the amino acid sequences of SEQ ID NOs: 27, 28, and 29, respectively, and an L-CDR1, L-CDR2, and L-CDR3 comprising the amino acid sequences of SEQ ID NOS: 30, 31, and 32, respectively.

In one embodiment, the anti-MET antibody or antigen-binding portion thereof has a heavy chain variable domain comprising the amino acid sequence of SEQ ID NO: 6, 10, 14, or 18. In one embodiment, the anti-MET antibody or antigen-binding portion thereof has a light chain variable domain comprising the amino acid sequence of SEQ ID NO: 8, 12, 16, or 20. In one embodiment, the anti-MET antibody or antigen-binding portion thereof has a heavy chain variable domain comprising the amino acid sequence of SEQ ID NO: 6, 10, 14, or 18 and a light chain variable domain comprising the amino acid sequence of SEQ ID NO: 8, 12, 16, or 20. In certain embodiments, the anti-MET antibody or antigen-binding portion thereof comprises:

a heavy chain variable domain comprising the amino acid sequence of SEQ ID NO: 6 and a light chain variable domain comprising the amino acid sequence of SEQ ID NO: 8;

a heavy chain variable domain comprising the amino acid sequence of SEQ ID NO: 10 and a light chain variable domain comprising the amino acid sequence of SEQ ID NO: 12;

a heavy chain variable domain comprising the amino acid sequence of SEQ ID NO: 14 and a light chain variable domain comprising the amino acid sequence of SEQ ID NO: 16; or a heavy chain variable domain comprising the amino acid sequence of SEQ ID NO: 18 and a light chain variable domain comprising the amino acid sequence of SEQ ID NO: 20.

In certain embodiments, the anti-MET antibody or antigen-binding portion thereof comprises a heavy chain that comprises the amino acid sequence of SEQ ID NO: 34 and a light chain that comprises the amino acid sequence of SEQ ID NO: 33.

In certain embodiments, the anti-MET antibody or antigen-binding portion thereof comprises a heavy chain that comprises the amino acid sequence of SEQ ID NO: 36 and a light chain that comprises the amino acid sequence of SEQ ID NO: 35.

In another aspect, the present invention provides a variant of an antibody or portion thereof as described above, wherein said variant differs from the antibody or portion thereof by 1, 2, 3, 4, 5, 6, 7, 8, 9 or 10 amino acid substitutions.

In one embodiment, the invention provides an anti-MET antibody that comprises a heavy chain variable domain that is at least 90% identical in amino acid sequence to SEQ ID NO: 6, 10, 14, or 18, or an antigen-binding portion of said antibody. In certain embodiments, the heavy chain variable domain is at least 91%, 92%, 93%, 94%, 95%, 96%, 97%, 98%, or 99% identical in amino acid sequence to SEQ ID NO: 6, 10, 14, or 18. In one embodiment, the invention provides an anti-MET antibody that comprises a light chain variable domain that is at least 90% identical in amino acid sequence to SEQ ID NO: 8, 12, 16, or 20, or an antigen-binding portion of said antibody. In certain embodiments, the light chain variable domain is at least 91%, 92%, 93%, 94%, 95%, 96%, 97%, 98%, or 99% identical in amino acid sequence to SEQ ID NO: 8, 12, 16, or 20. The anti-MET antibody may also comprise any combination of the above-referenced heavy and light chain variable domains.

In one embodiment, the invention provides an anti-MET antibody that comprises a heavy chain that is at least 90% identical in amino acid sequence to SEQ ID NO: 34 or 36, or an antigen-binding portion of said antibody. In certain embodiments, the heavy chain is at least 91%, 92%, 93%, 94%, 95%, 96%, 97%, 98%, or 99% identical in amino acid sequence to SEQ ID NO: 34 or 36. In one embodiment, the invention provides an anti-MET antibody that comprises a light chain that is at least 90% identical in amino acid sequence to SEQ ID NO: 33 or 35, or an antigen-binding portion of said antibody. In certain embodiments, the light chain is at least 91%, 92%, 93%, 94%, 95%, 96%, 97%, 98%, or 99% identical in amino acid sequence to SEQ ID NO: 33 or 35. The anti-MET antibody may also comprise any combination of the above-referenced heavy and light chain variable domains.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA employing default or recommended parameters; a program in GCG Version 6.1. FASTA (e.g., FASTA2 and FASTA3) provides alignments and percent sequence identity of the regions of best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters. See, e.g., Altschul et al., *J. Mol. Biol.* 215:403-410 (1990); Altschul et al., *Nucleic Acids Res.* 25:3389-402 (1997); incorporated herein by reference.

The length of polypeptide sequences compared for homology will generally be at least about 16 amino acid residues, usually at least about 20 residues, more usually at least about 24 residues, typically at least about 28 residues, and preferably more than about 35 residues.

According to the invention, one type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be made in a CDR or framework region of a variable domain or in the constant domain of an antibody. In some embodiments, the cysteine is canonical.

Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity.

Another type of amino acid substitution is to eliminate asparagine-glycine pairs, which form potential deamidation sites, by altering one or both of the residues.

Another type of amino acid substitution that may be made in one of the variants according to the invention is a conservative amino acid substitution. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well known to those of skill in the art. See, e.g., Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement may be defined as any change having a positive value in the PAM250 log-likelihood matrix disclosed in Gonnet et al., *Science* 256:1443-45 (1992). A "moderately conservative" replacement is any change having a nonnegative value in the PAM250 log-likelihood matrix.

In certain embodiments, amino acid substitutions to an antibody or antigen-binding portion of the invention are those which: (1) reduce susceptibility to proteolysis, (2) reduce susceptibility to oxidation, (3) alter binding affinity for forming protein complexes, and (4) confer or modify other physicochemical or functional properties of such analogs, but still retain specific binding to human MET. Analogs can include various substitutions to the normally-occurring peptide sequence. For example, single or multiple amino acid substitutions, preferably conservative amino acid substitutions, may be made in the normally-occurring sequence, for example in the portion of the polypeptide outside the domain(s) forming intermolecular contacts. Amino acid substitutions can also be made in the domain(s) that form intermolecular contacts that can improve the activity of the polypeptide. A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354:105 (1991).

In another aspect of the invention, the antibody may be deimmunized to reduce its immunogenicity using the techniques described in, e.g., PCT Publications WO 98/52976 and WO 00/34317.

In some embodiments, any of the anti-MET antibodies or antigen-binding portions described herein also may have at least one functional property selected from the group consisting of:

does not bind to mouse or chicken MET;
binds to an epitope of human MET comprising residues that are present on the SEMA domain;
induces degradation of MET;
binds to human MET with a $K_D$ of $1 \times 10^{-9}$ M or less;
inhibits growth in vitro of at least one cell line selected from SNU5, EBC1, MKN45, KatoII, OE33, and Okajima; and
inhibits tumor growth in vivo;

or any combination of said functional properties. In some embodiments, binding of one or more antibodies or antigen-binding portions of the invention (and in particular an anti-MET antibody composition of the invention) to MET may inhibit the growth and proliferation of cells expressing the receptors (i.e., tumor cells).

In some embodiments, any of the anti-MET antibodies or antigen-binding portions described herein may inhibit binding of HGF alpha or HGF beta to MET. In some embodiments, the antibodies or portions may inhibit binding of unprocessed HGF to MET.

As used herein, the term "inhibits growth" (e.g., referring to cells) is intended to include any measurable decrease in the proliferation (increase in number of cells) or metabolism of a cell when contacted with an anti-MET antibody or antigen-binding portion or anti-MET antibody composition as compared to the growth of the same cells in the absence of the antibody or composition, e.g., inhibition of growth of a cell culture by at least about 10%, and preferably more, such as at least about 20% or 30%, more preferably at least about 40% or 50%, such as at least about 60%, 70%, 80%, 90%, 95% or 99%, or even about 100%. Growth inhibition can be determined in relevant cancer cell lines, e.g., as described in the examples below.

The class of an anti-MET antibody obtained by the methods described herein may be switched with another class. In one aspect of the invention, a nucleic acid molecule encoding VL or VH is isolated using methods well-known in the art such that it does not include nucleic acid sequences encoding CL or CH. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH chain, as described above. For example, an anti-MET antibody that was originally IgM may be class switched to IgG. Further, the class switching may be used to convert one IgG subclass to another, e.g., from IgG1 to IgG2. A preferred method for producing an antibody of the invention with a desired isotype comprises the steps of isolating a nucleic acid molecule encoding the heavy chain of an anti-MET antibody and a nucleic acid molecule encoding the light chain of an anti-MET antibody, obtaining the variable domain of the heavy chain, ligating the variable domain of the heavy chain with the constant domain of a heavy chain of the desired isotype, expressing the light chain and the ligated heavy chain in a cell, and collecting the anti-MET antibody with the desired isotype.

The anti-MET antibody of the invention can be an IgG, an IgM, an IgE, an IgA, or an IgD molecule. In one embodiment, the anti-MET antibody is an IgG molecule and is of the IgG1, IgG2, IgG3, or IgG4 subclass. In certain embodiments, the antibody is of subclass IgG1.

In certain embodiments, an antibody or antigen-binding portion thereof of the invention may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., *Mol. Immunol.* 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another embodiment, a fusion antibody or immunoadhesin may be made that comprises all or a portion of an anti-MET antibody of the invention linked to another polypeptide. In certain embodiments, only the variable domains of the anti-MET antibody are linked to the polypeptide. In certain embodiments, the VH domain of an anti-MET antibody is linked to a first polypeptide, while the VL domain of an anti-MET antibody is linked to a second polypeptide that associates with the first polypeptide in a manner such that the VH and VL domains can interact with one another to form an antigen-binding site. In another preferred embodiment, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody (scFv), the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH domains joined by the flexible linker. See, e.g., Bird et al., *Science* 242:423-426 (1988); Huston et al., *Proc. Natl. Acad. Sci. USA* 85:5879-5883 (1988); and McCafferty et al., *Nature* 348:552-554 (1990). The single chain antibody may be monovalent, if only a single VH and VL are used; bivalent, if two VH and VL are used; or polyvalent, if more than two VH and VL are used. Bispecific or polyvalent antibodies may be generated that bind specifically to human MET and to another molecule, for instance.

In other embodiments, other modified antibodies may be prepared using anti-MET antibody-encoding nucleic acid molecules. For instance, "kappa bodies" (111 et al., *Protein Eng.* 10:949-57 (1997)), "minibodies" (Martin et al., *EMBO J.* 13:5303-9 (1994)), "diabodies" (Holliger et al., *Proc. Natl. Acad. Sci. USA* 90:6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

An anti-MET antibody or antigen-binding portion of the invention can be derivatized or linked to another molecule (e.g., another peptide or protein). In general, the antibodies or portions thereof are derivatized such that MET binding is not affected adversely by the derivatization or labeling. Accordingly, the antibodies and antibody portions of the invention are intended to include both intact and modified forms of the human anti-MET antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

An anti-MET antibody can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody according to the present invention may also be labeled. As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain embodiments, the antibodies of the invention may be present in a neutral form (including zwitter ionic forms) or as a positively or negatively-charged species. In some embodiments, the antibodies may be complexed with a counterion to form a pharmaceutically acceptable salt.

The term "pharmaceutically acceptable salt" refers to a complex comprising one or more antibodies and one or more counterions, wherein the counterions are derived from pharmaceutically acceptable inorganic and organic acids and bases.

Pharmaceutically acceptable inorganic bases include metallic ions including, but are not limited to, appropriate alkali metal salts, alkaline earth metal salts and other physiological acceptable metal ions. Salts derived from inorganic bases include aluminum, ammonium, calcium, cobalt, nickel, molybdenum, vanadium, manganese, chromium, selenium, tin, copper, ferric, ferrous, lithium, magnesium, manganic or manganous salts, potassium, rubidium, sodium, and zinc, e.g., in their usual valences.

Pharmaceutically acceptable acid addition salts of the antibodies of the present invention can be prepared from the following acids, including, without limitation, formic, acetic, acetamidobenzoic, adipic, ascorbic, boric, propionic, benzoic, camphoric, carbonic, cyclamic, dehydrocholic, malonic, edetic, ethylsulfuric, fendizoic, metaphosphoric, succinic, glycolic, gluconic, lactic, malic, tartaric, tannic, citric, nitric, ascorbic, glucuronic, maleic, folic, fumaric, propionic, pyruvic, aspartic, glutamic, benzoic, hydrochloric, hydrobromic, hydroiodic, lysine, isocitric, trifluoroacetic, pamoic, propionic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, glutamic, cacodylate, diaminohexanoic, camphorsulfonic, gluconic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N, N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris(hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino]ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxypropanesulfonic acid, 2-hydroxy-3-[tris(hydroxymethyl)methylamino]-1-propanesulfonic acid, 4-(2-hydroxyethyl)piperazine-1-(2-hydroxypropanesulfonic acid), piperazine-1,4-bis(2-hydroxypropanesulfonic acid) dihydrate, 4-(2-hydroxyethyl)-1-piperazinepropanesulfonic acid, N,N-bis(2-hydroxyethyl)glycine, N-(2-hydroxyethyl)piperazine-N'-(4-butanesulfonic acid), N-[tris(hydroxymethyl)methyl]-3-aminopropanesulfonic acid, N-tris(Hydroxymethyl)methyl-4-aminobutanesulfonic acid, N-(1,1-dimethyl-2-hydroxyethyl)-3-amino-2-hydroxypropanesulfonic acid, 2-(cyclohexylamino)ethanesulfonic acid, 3-(cyclohexylamino)-2-hydroxy-1-propanesulfonic acid, 3-(cyclohexylamino)-1-propanesulfonic acid, N-(2-acetamido)iminodiacetic acid, 4-(cyclohexylamino)-1-butanesulfonic acid, N-[tris(hydroxymethyl)methyl]glycine, 2-amino-2-(hydroxymethyl)-1,3-propanediol, and trometamol.

Anti-MET Antibody Compositions

In one aspect, the invention provides an antibody composition comprising at least two antibodies or antigen-binding portions thereof of the invention. The term "anti-MET antibody composition" refers to a composition comprising at least two anti-MET antibodies or antigen-binding portions thereof.

In one embodiment, the antibody composition comprises a first anti-MET antibody or an antigen-binding portion thereof and a second anti-MET antibody or an antigen-binding portion thereof, wherein the first anti-MET antibody is selected from the group consisting of:

an anti-MET antibody or an antigen-binding portion thereof that competes for binding to human MET with an antibody having an H-CDR1, H-CDR2, H-CDR3, L-CDR1, L-CDR2, and L-CDR3 that comprise the amino acid sequences of SEQ ID NOs: 21, 22, 23, 24, 25, and 26, respectively;

an anti-MET antibody or an antigen-binding portion thereof that binds to the same epitope of human MET as an antibody having an H-CDR1, H-CDR2, H-CDR3, L-CDR1, L-CDR2, and L-CDR3 that comprise the amino acid sequences of SEQ ID NOs: 21, 22, 23, 24, 25, and 26, respectively;

an anti-MET antibody or an antigen-binding portion thereof that competes for binding to human MET with an antibody having a heavy chain variable domain comprising the amino acid sequence of SEQ ID NO: 6 and a light chain variable domain comprising the amino acid sequence of SEQ ID NO: 8;

an anti-MET antibody or an antigen-binding portion thereof that competes for binding to human MET with an antibody having a heavy chain variable domain comprising the amino acid sequence of SEQ ID NO: 14 and a light chain variable domain comprising the amino acid sequence of SEQ ID NO: 16;

an anti-MET antibody or an antigen-binding portion thereof that binds to the same epitope of human MET as an antibody having a heavy chain variable domain comprising the amino acid sequence of SEQ ID NO: 6 and a light chain variable domain comprising the amino acid sequence of SEQ ID NO: 8;

an anti-MET antibody or an antigen-binding portion thereof that binds to the same epitope of human MET as an antibody having a heavy chain variable domain comprising the amino acid sequence of SEQ ID NO: 14 and a light chain variable domain comprising the amino acid sequence of SEQ ID NO: 16;

an anti-MET antibody or an antigen-binding portion thereof having an H-CDR3 comprising the amino acid sequence of SEQ ID NO: 23;

an anti-MET antibody or an antigen-binding portion thereof having an L-CDR3 comprising the amino acid sequence of SEQ ID NO: 26;

an anti-MET antibody or an antigen-binding portion thereof having an H-CDR3 comprising the amino acid sequence of SEQ ID NO: 23 and an L-CDR3 comprising the amino acid sequence of SEQ ID NO: 26;

an anti-MET antibody or an antigen-binding portion thereof having an H-CDR1, H-CDR2, and H-CDR3 comprising the amino acid sequences of SEQ ID NOS: 21, 22, and 23, respectively;

an anti-MET antibody or an antigen-binding portion thereof having an L-CDR1, L-CDR2, and L-CDR3 comprising the amino acid sequences of SEQ ID NOS: 24, 25, and 26, respectively;

an anti-MET antibody or an antigen-binding portion thereof having an H-CDR1, H-CDR2, and H-CDR3 comprising the amino acid sequences of SEQ ID NOs: 21, 22, and 23, respectively, and an L-CDR1, L-CDR2, and L-CDR3 comprising the amino acid sequences of SEQ ID NOS: 24, 25, and 26, respectively;

an anti-MET antibody or an antigen-binding portion thereof having a heavy chain variable domain comprising the amino acid sequence of SEQ ID NO: 6 or 14;

an anti-MET antibody or an antigen-binding portion thereof having a light chain variable domain comprising the amino acid sequence of SEQ ID NO: 8 or 16;

an anti-MET antibody or an antigen-binding portion thereof having a heavy chain variable domain comprising the amino acid sequence of SEQ ID NO: 6 and a light chain variable domain comprising the amino acid sequence of SEQ ID NO: 8;

an anti-MET antibody or an antigen-binding portion thereof having a heavy chain variable domain comprising the amino acid sequence of SEQ ID NO: 14 and a light chain variable domain comprising the amino acid sequence of SEQ ID NO: 16;

an anti-MET antibody or an antigen-binding portion thereof having a heavy chain variable domain at least 91%, 92%, 93%, 94%, 95%, 96%, 97%, 98%, or 99% identical to the amino acid sequence of SEQ ID NO: 6 and a light chain variable domain at least 91%, 92%, 93%, 94%, 95%, 96%, 97%, 98%, or 99% identical to the amino acid sequence of SEQ ID NO: 8;

an anti-MET antibody or an antigen-binding portion thereof having a heavy chain variable domain at least 91%, 92%, 93%, 94%, 95%, 96%, 97%, 98%, or 99% identical to the amino acid sequence of SEQ ID NO: 14 and a light chain variable domain at least 91%, 92%, 93%, 94%, 95%, 96%, 97%, 98%, or 99% identical to the amino acid sequence of SEQ ID NO: 16;

an anti-MET antibody or an antigen-binding portion thereof having a heavy chain comprising the amino acid sequence of SEQ ID NO: 34 and a light chain comprising the amino acid sequence of SEQ ID NO: 33; and an anti-MET antibody or an antigen-binding portion thereof having a heavy chain at least 91%, 92%, 93%, 94%, 95%, 96%, 97%, 98%, or 99% identical to the amino acid sequence of SEQ ID NO: 34 and a light chain at least 91%, 92%, 93%, 94%, 95%, 96%, 97%, 98%, or 99% identical to the amino acid sequence of SEQ ID NO: 33;

and wherein the second anti-MET antibody is selected from the group consisting of:

an anti-MET antibody or an antigen-binding portion thereof that competes for binding to human MET with an antibody having an H-CDR1, H-CDR2, H-CDR3, L-CDR1, L-CDR2, and L-CDR3 that comprise the amino acid sequences of SEQ ID NOs: 27, 28, 29, 30, 31, and 32, respectively;

an anti-MET antibody or an antigen-binding portion thereof that binds to the same epitope of human MET as an antibody having an H-CDR1, H-CDR2, H-CDR3, L-CDR1, L-CDR2, and L-CDR3 that comprise the amino acid sequences of SEQ ID NOs: 27, 28, 29, 30, 31, and 32, respectively;

an anti-MET antibody or an antigen-binding portion thereof that competes for binding to human MET with an antibody having a heavy chain variable domain comprising the amino acid sequence of SEQ ID NO: 10 and a light chain variable domain comprising the amino acid sequence of SEQ ID NO: 12;

an anti-MET antibody or an antigen-binding portion thereof that competes for binding to human MET with an antibody having a heavy chain variable domain comprising the amino acid sequence of SEQ ID NO: 18 and a light chain variable domain comprising the amino acid sequence of SEQ ID NO: 20;

an anti-MET antibody or an antigen-binding portion thereof that binds to the same epitope of human MET as an antibody having a heavy chain variable domain comprising the amino acid sequence of SEQ ID NO: 10 and a light chain variable domain comprising the amino acid sequence of SEQ ID NO: 12;

an anti-MET antibody or an antigen-binding portion thereof that binds to the same epitope of human MET as an antibody having a heavy chain variable domain comprising the amino acid sequence of SEQ ID NO: 18 and a light chain variable domain comprising the amino acid sequence of SEQ ID NO: 20;

an anti-MET antibody or an antigen-binding portion thereof having an H-CDR3 comprising the amino acid sequence of SEQ ID NO: 29;

an anti-MET antibody or an antigen-binding portion thereof having an L-CDR3 comprising the amino acid sequence of SEQ ID NO: 32;

an anti-MET antibody or an antigen-binding portion thereof having an H-CDR3 comprising the amino acid sequence of SEQ ID NO: 29 and an L-CDR3 comprising the amino acid sequence of SEQ ID NO: 32;

an anti-MET antibody or an antigen-binding portion thereof having an H-CDR1, H-CDR2, and H-CDR3 comprising the amino acid sequences of SEQ ID NOS: 27, 28, and 29, respectively;

an anti-MET antibody or an antigen-binding portion thereof having an L-CDR1, L-CDR2, and L-CDR3 comprising the amino acid sequences of SEQ ID NOS: 30, 31, and 32, respectively;

an anti-MET antibody or an antigen-binding portion thereof having an H-CDR1, H-CDR2, and H-CDR3 comprising the amino acid sequences of SEQ ID NOs: 27, 28, and 29, respectively, and an L-CDR1, L-CDR2, and L-CDR3 comprising the amino acid sequences of SEQ ID NOS: 30, 31, and 32, respectively;

an anti-MET antibody or an antigen-binding portion thereof having a heavy chain variable domain comprising the amino acid sequence of SEQ ID NO: 10 or 18;

an anti-MET antibody or an antigen-binding portion thereof having a light chain variable domain comprising the amino acid sequence of SEQ ID NO: 12 or 20;

an anti-MET antibody or an antigen-binding portion thereof having a heavy chain variable domain comprising the amino acid sequence of SEQ ID NO: 10 and a light chain variable domain comprising the amino acid sequence of SEQ ID NO: 12;

an anti-MET antibody or an antigen-binding portion thereof having a heavy chain variable domain comprising the amino acid sequence of SEQ ID NO: 18 and a light chain variable domain comprising the amino acid sequence of SEQ ID NO: 20;

an anti-MET antibody or an antigen-binding portion thereof having a heavy chain variable domain at least 91%, 92%, 93%, 94%, 95%, 96%, 97%, 98%, or 99% identical to the amino acid sequence of SEQ ID NO: 10 and a light chain variable domain at least 91%, 92%, 93%, 94%, 95%, 96%, 97%, 98%, or 99% identical to the amino acid sequence of SEQ ID NO: 12;

an anti-MET antibody or an antigen-binding portion thereof having a heavy chain variable domain at least 91%, 92%, 93%, 94%, 95%, 96%, 97%, 98%, or 99% identical to the amino acid sequence of SEQ ID NO: 18 and a light chain variable domain at least 91%, 92%, 93%, 94%, 95%, 96%, 97%, 98%, or 99% identical to the amino acid sequence of SEQ ID NO: 20;

an anti-MET antibody or an antigen-binding portion thereof having a heavy chain comprising the amino acid sequence of SEQ ID NO: 36 and a light chain comprising the amino acid sequence of SEQ ID NO: 35; and an anti-MET antibody or an antigen-binding portion thereof having a heavy chain at least 91%, 92%, 93%, 94%, 95%, 96%, 97%, 98%, or 99% identical to the amino acid sequence of SEQ ID NO: 36 and a light chain at least 91%, 92%, 93%, 94%, 95%, 96%, 97%, 98%, or 99% identical to the amino acid sequence of SEQ ID NO: 35.

Any combination of the above first and second anti-MET antibodies is contemplated.

In one embodiment, the antibody composition comprises:

an anti-MET antibody or an antigen-binding portion thereof that competes for binding to human MET with an antibody having an H-CDR1, H-CDR2, H-CDR3, L-CDR1, L-CDR2, and L-CDR3 that comprise the amino acid sequences of SEQ ID NOs: 21, 22, 23, 24, 25, and 26, respectively; and an anti-MET antibody or an antigen-binding portion thereof that competes for binding to human MET with an antibody having an H-CDR1, H-CDR2, H-CDR3, L-CDR1, L-CDR2, and L-CDR3 that comprise the amino acid sequences of SEQ ID NOs: 27, 28, 29, 30, 31, and 32, respectively.

In one embodiment, the antibody composition comprises:
an anti-MET antibody or an antigen-binding portion thereof that binds to the same epitope of human MET as an antibody having an H-CDR1, H-CDR2, H-CDR3, L-CDR1, L-CDR2, and L-CDR3 that comprise the amino acid sequences of SEQ ID NOs: 21, 22, 23, 24, 25, and 26, respectively; and
an anti-MET antibody or an antigen-binding portion thereof that binds to the same epitope of human MET as an antibody having an H-CDR1, H-CDR2, H-CDR3, L-CDR1, L-CDR2, and L-CDR3 that comprise the amino acid sequences of SEQ ID NOs: 27, 28, 29, 30, 31, and 32, respectively.

In one embodiment, the antibody composition comprises:
an anti-MET antibody or an antigen-binding portion thereof that competes for binding to human MET with an antibody having a heavy chain variable domain comprising the amino acid sequence of SEQ ID NO: 6 and a light chain variable domain comprising the amino acid sequence of SEQ ID NO: 8; and
an anti-MET antibody or an antigen-binding portion thereof that competes for binding to human MET with an antibody having a heavy chain variable domain comprising the amino acid sequence of SEQ ID NO: 10 and a light chain variable domain comprising the amino acid sequence of SEQ ID NO: 12.

In one embodiment, the antibody composition comprises:
an anti-MET antibody or an antigen-binding portion thereof that competes for binding to human MET with an antibody having a heavy chain variable domain comprising the amino acid sequence of SEQ ID NO: 14 and a light chain variable domain comprising the amino acid sequence of SEQ ID NO: 16; and
an anti-MET antibody or an antigen-binding portion thereof that competes for binding to human MET with an antibody having a heavy chain variable domain comprising the amino acid sequence of SEQ ID NO: 18 and a light chain variable domain comprising the amino acid sequence of SEQ ID NO: 20.

In one embodiment, the antibody composition comprises:
an anti-MET antibody or an antigen-binding portion thereof that competes for binding to human MET with an antibody having a heavy chain comprising the amino acid sequence of SEQ ID NO: 34 and a light chain comprising the amino acid sequence of SEQ ID NO: 33; and
an anti-MET antibody or an antigen-binding portion thereof that competes for binding to human MET with an antibody having a heavy chain comprising the amino acid sequence of SEQ ID NO: 36 and a light chain comprising the amino acid sequence of SEQ ID NO: 35.

In one embodiment, the antibody composition comprises:
an anti-MET antibody or an antigen-binding portion thereof that binds to the same epitope of human MET as an antibody having a heavy chain variable domain comprising the amino acid sequence of SEQ ID NO: 6 and a light chain variable domain comprising the amino acid sequence of SEQ ID NO: 8; and
an anti-MET antibody or an antigen-binding portion thereof that binds to the same epitope of human MET as an antibody having a heavy chain variable domain comprising the amino acid sequence of SEQ ID NO: 10 and a light chain variable domain comprising the amino acid sequence of SEQ ID NO: 12.

In one embodiment, the antibody composition comprises:
an anti-MET antibody or an antigen-binding portion thereof that binds to the same epitope of human MET as an antibody having a heavy chain variable domain comprising the amino acid sequence of SEQ ID NO: 14 and a light chain variable domain comprising the amino acid sequence of SEQ ID NO: 16; and
an anti-MET antibody or an antigen-binding portion thereof that binds to the same epitope of human MET as an antibody having a heavy chain variable domain comprising the amino acid sequence of SEQ ID NO: 18 and a light chain variable domain comprising the amino acid sequence of SEQ ID NO: 20.

In one embodiment, the antibody composition comprises:
an anti-MET antibody or an antigen-binding portion thereof that binds to the same epitope of human MET as an antibody having a heavy chain comprising the amino acid sequence of SEQ ID NO: 34 and a light chain comprising the amino acid sequence of SEQ ID NO: 33; and
an anti-MET antibody or an antigen-binding portion thereof that binds to the same epitope of human MET as an antibody having a heavy chain comprising the amino acid sequence of SEQ ID NO: 36 and a light chain comprising the amino acid sequence of SEQ ID NO: 35.

In one embodiment, the antibody composition comprises:
an anti-MET antibody or an antigen-binding portion thereof having an H-CDR3 comprising the amino acid sequence of SEQ ID NO: 23; and
an anti-MET antibody or an antigen-binding portion thereof having an H-CDR3 comprising the amino acid sequence of SEQ ID NO: 29.

In one embodiment, the antibody composition comprises:
an anti-MET antibody or an antigen-binding portion thereof having an L-CDR3 comprising the amino acid sequence of SEQ ID NO: 26; and
an anti-MET antibody or an antigen-binding portion thereof having an L-CDR3 comprising the amino acid sequence of SEQ ID NO: 32.

In one embodiment, the antibody composition comprises:
an anti-MET antibody or an antigen-binding portion thereof having an H-CDR3 comprising the amino acid sequence of SEQ ID NO: 23 and an L-CDR3 comprising the amino acid sequence of SEQ ID NO: 26; and
an anti-MET antibody or an antigen-binding portion thereof having an H-CDR3 comprising the amino acid sequence of SEQ ID NO: 29 and an L-CDR3 comprising the amino acid sequence of SEQ ID NO: 32.

In one embodiment, the antibody composition comprises:
an anti-MET antibody or an antigen-binding portion thereof having an H-CDR1, H-CDR2, and H-CDR3 comprising the amino acid sequences of SEQ ID NOS: 21, 22, and 23, respectively; and
an anti-MET antibody or an antigen-binding portion thereof having an H-CDR1, H-CDR2, and H-CDR3 comprising the amino acid sequences of SEQ ID NOS: 27, 28, and 29, respectively.

In one embodiment, the antibody composition comprises:
an anti-MET antibody or an antigen-binding portion thereof having an L-CDR1, L-CDR2, and L-CDR3 comprising the amino acid sequences of SEQ ID NOS: 24, 25, and 26, respectively; and
an anti-MET antibody or an antigen-binding portion thereof having an L-CDR1, L-CDR2, and L-CDR3 comprising the amino acid sequences of SEQ ID NOS: 30, 31, and 32, respectively.

In one embodiment, the antibody composition comprises:
an anti-MET antibody or an antigen-binding portion thereof having an H-CDR1, H-CDR2, and H-CDR3 comprising the amino acid sequences of SEQ ID NOs: 21, 22, and 23, respectively, and an L-CDR1, L-CDR2, and L-CDR3 comprising the amino acid sequences of SEQ ID NOS: 24, 25, and 26, respectively; and
an anti-MET antibody or an antigen-binding portion thereof having an H-CDR1, H-CDR2, and H-CDR3 comprising the amino acid sequences of SEQ ID NOs: 27, 28, and 29, respectively, and an L-CDR1, L-CDR2, and L-CDR3 comprising the amino acid sequences of SEQ ID NOS: 30, 31, and 32, respectively.

In one embodiment, the antibody composition comprises:
an anti-MET antibody or an antigen-binding portion thereof having a heavy chain variable domain comprising the amino acid sequence of SEQ ID NO: 6 and a light chain variable domain comprising the amino acid sequence of SEQ ID NO: 8; and
an anti-MET antibody or an antigen-binding portion thereof having a heavy chain variable domain comprising the amino acid sequence of SEQ ID NO: 10 and a light chain variable domain comprising the amino acid sequence of SEQ ID NO: 12.

In one embodiment, the antibody composition comprises:
an anti-MET antibody or an antigen-binding portion thereof having a heavy chain variable domain comprising the amino acid sequence of SEQ ID NO: 14 and a light chain variable domain comprising the amino acid sequence of SEQ ID NO: 16; and
an anti-MET antibody or an antigen-binding portion thereof having a heavy chain variable domain comprising the amino acid sequence of SEQ ID NO: 18 and a light chain variable domain comprising the amino acid sequence of SEQ ID NO: 20.

In one embodiment, the antibody composition comprises:
an anti-MET antibody or an antigen-binding portion thereof having a heavy chain comprising the amino acid sequence of SEQ ID NO: 34 and a light chain comprising the amino acid sequence of SEQ ID NO: 33; and
an anti-MET antibody or an antigen-binding portion thereof having a heavy chain comprising the amino acid sequence of SEQ ID NO: 36 and a light chain comprising the amino acid sequence of SEQ ID NO: 35.

In one embodiment, the antibody composition comprises:
an anti-MET antibody or an antigen-binding portion thereof having a heavy chain variable domain at least 91%, 92%, 93%, 94%, 95%, 96%, 97%, 98%, or 99% identical to the amino acid sequence of SEQ ID NO: 6 and a light chain variable domain at least 91%, 92%, 93%, 94%, 95%, 96%, 97%, 98%, or 99% identical to the amino acid sequence of SEQ ID NO: 8; and
an anti-MET antibody or an antigen-binding portion thereof having a heavy chain variable domain at least 91%, 92%, 93%, 94%, 95%, 96%, 97%, 98%, or 99% identical to the amino acid sequence of SEQ ID NO: 10 and a light chain variable domain at least 91%, 92%, 93%, 94%, 95%, 96%, 97%, 98%, or 99% identical to the amino acid sequence of SEQ ID NO: 12.

Any combination of the above identity percentages of the first and second antibodies is contemplated.

In one embodiment, the antibody composition comprises:
an anti-MET antibody or an antigen-binding portion thereof having a heavy chain variable domain at least 91%, 92%, 93%, 94%, 95%, 96%, 97%, 98%, or 99% identical to the amino acid sequence of SEQ ID NO: 14 and a light chain variable domain at least 91%, 92%, 93%, 94%, 95%, 96%, 97%, 98%, or 99% identical to the amino acid sequence of SEQ ID NO: 16; and
an anti-MET antibody or an antigen-binding portion thereof having a heavy chain variable domain at least 91%, 92%, 93%, 94%, 95%, 96%, 97%, 98%, or 99% identical to the amino acid sequence of SEQ ID NO: 18 and a light chain variable domain at least 91%, 92%, 93%, 94%, 95%, 96%, 97%, 98%, or 99% identical to the amino acid sequence of SEQ ID NO: 20.

Any combination of the above identity percentages of the first and second antibodies is contemplated.

In one embodiment, the antibody composition comprises:
an anti-MET antibody or an antigen-binding portion thereof having a heavy chain at least 91%, 92%, 93%, 94%, 95%, 96%, 97%, 98%, or 99% identical to the amino acid sequence of SEQ ID NO: 34 and a light chain at least 91%, 92%, 93%, 94%, 95%, 96%, 97%, 98%, or 99% identical to the amino acid sequence of SEQ ID NO: 33; and
an anti-MET antibody or an antigen-binding portion thereof having a heavy chain at least 91%, 92%, 93%, 94%, 95%, 96%, 97%, 98%, or 99% identical to the amino acid sequence of SEQ ID NO: 36 and a light chain at least 91%, 92%, 93%, 94%, 95%, 96%, 97%, 98%, or 99% identical to the amino acid sequence of SEQ ID NO: 35.

Any combination of the above identity percentages of the first and second antibodies is contemplated.

Bispecific Binding Molecules

In a further aspect, the binding specificities of any two individual antibodies disclosed herein may be combined in one bispecific binding molecule. For example, a bispecific binding molecule may have the binding specificities of anti-MET antibodies 9006 and 9338. In some embodiments, the bispecific binding molecule may have the binding specificities of:
an anti-MET antibody or an antigen-binding portion thereof having an H-CDR1, H-CDR2, and H-CDR3 comprising the amino acid sequences of SEQ ID NOs: 21, 22, and 23, respectively, and an L-CDR1, L-CDR2, and L-CDR3 comprising the amino acid sequences of SEQ ID NOS: 24, 25, and 26, respectively; and
an anti-MET antibody or an antigen-binding portion thereof having an H-CDR1, H-CDR2, and H-CDR3 comprising the amino acid sequences of SEQ ID NOs: 27, 28, and 29, respectively, and an L-CDR1, L-CDR2, and L-CDR3 comprising the amino acid sequences of SEQ ID NOS: 30, 31, and 32, respectively.

In some embodiments, the bispecific binding molecule may have the binding specificities of:
an anti-MET antibody or an antigen-binding portion thereof having a heavy chain variable domain comprising the amino acid sequence of SEQ ID NO: 6 and a light chain variable domain comprising the amino acid sequence of SEQ ID NO: 8; and
an anti-MET antibody or an antigen-binding portion thereof having a heavy chain variable domain comprising the amino acid sequence of SEQ ID NO: 10 and a light chain variable domain comprising the amino acid sequence of SEQ ID NO: 12.

In some embodiments, the bispecific binding molecule may have the binding specificities of:

an anti-MET antibody or an antigen-binding portion thereof having a heavy chain variable domain comprising the amino acid sequence of SEQ ID NO: 14 and a light chain variable domain comprising the amino acid sequence of SEQ ID NO: 16; and an anti-MET antibody or an antigen-binding portion thereof having a heavy chain variable domain comprising the amino acid sequence of SEQ ID NO: 18 and a light chain variable domain comprising the amino acid sequence of SEQ ID NO: 20.

In some embodiments, the bispecific binding molecule may have the binding specificities of:

an anti-MET antibody or an antigen-binding portion thereof having a heavy chain comprising the amino acid sequence of SEQ ID NO: 34 and a light chain comprising the amino acid sequence of SEQ ID NO: 33; and an anti-MET antibody or an antigen-binding portion thereof having a heavy chain comprising the amino acid sequence of SEQ ID NO: 36 and a light chain comprising the amino acid sequence of SEQ ID NO: 35.

The bispecific binding molecule may be a dual variable domain antibody, i.e., wherein the two arms of the antibody comprise two different variable domains, or may be in the form of an antibody fragment such as a bispecific Fab fragment or a bispecific scFv.

Nucleic Acid Molecules and Vectors

The present invention also provides nucleic acid molecules and sequences encoding anti-MET antibodies or antigen-binding portions thereof described herein. In some embodiments, different nucleic acid molecules encode the heavy chain and light chain amino acid sequences of the anti-MET antibody or an antigen-binding portion thereof. In other embodiments, the same nucleic acid molecule encodes the heavy chain and light chain amino acid sequences of the anti-MET antibody or an antigen-binding portion thereof.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single and double stranded forms.

The invention also provides nucleotide sequences that are at least 70%, 75%, 80%, 85%, 90%, 95%, 97%, 98% or 99% identical to one or more of the above-recited nucleotide sequences or to a nucleotide sequence encoding an amino acid sequence selected from the group consisting of SEQ ID NOs: 6, 8, 10, 12, 14, 16, 18, 20, and 33-36. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In one aspect, the invention provides a nucleic acid molecule comprising a nucleotide sequence selected from the group consisting of SEQ ID NOs: 5, 7, 9, 11, 13, 15, 17, and 19. In some embodiments, the nucleic acid molecule may comprise the nucleotide sequences of SEQ ID NOs: 5 and 7, 9 and 11, 13 and 15, or 17 and 19.

In any of the above embodiments, the nucleic acid molecules may be isolated.

In a further aspect, the present invention provides a vector suitable for expressing one of the chains of an antibody or antigen-binding portion thereof as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The invention provides vectors comprising nucleic acid molecules that encode the heavy chain of an anti-MET antibody of the invention or an antigen-binding portion thereof, the light chain of an anti-MET antibody of the invention or an antigen-binding portion thereof, or both the heavy and light chains of an anti-MET antibody of the invention or an antigen-binding portion thereof. The invention further provides vectors comprising nucleic acid molecules encoding fusion proteins, modified antibodies, antibody fragments, and probes thereof.

A nucleic acid molecule encoding the heavy and/or light chain of an anti-MET antibody or portion thereof can be isolated from any source that produces such an antibody or portion. In various embodiments, the nucleic acid molecules are isolated from B cells that express an anti-MET antibody isolated from an animal immunized with a human MET antigen, or from an immortalized cell produced from such a B cell. Methods of isolating nucleic acids encoding an antibody are well-known in the art. mRNA may be isolated and used to produce cDNA for use in polymerase chain reaction (PCR) or cDNA cloning of antibody genes. In certain embodiments, a nucleic acid molecule of the invention can be synthesized rather than isolated.

In some embodiments, a nucleic acid molecule of the invention can comprise a nucleotide sequence encoding a VH domain from an anti-MET antibody or antigen-binding portion of the invention joined in-frame to a nucleotide sequence encoding a heavy chain constant domain from any source. Similarly, a nucleic acid molecule of the invention can comprise a nucleotide sequence encoding a VL domain from an anti-MET antibody or antigen-binding portion of the invention joined in-frame to a nucleotide sequence encoding a light chain constant domain from any source.

In a further aspect of the invention, nucleic acid molecules encoding the variable domain of the heavy (VH) and/or light (VL) chains may be "converted" to full-length antibody genes. In one embodiment, nucleic acid molecules encoding the VH or VL domains are converted to full-length antibody genes by insertion into an expression vector already encoding heavy chain constant (CH) or light chain constant (CL) domains, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into full-length antibody genes by linking, e.g., ligating, a nucleic acid molecule encoding a VH and/or VL domains to a nucleic acid molecule encoding a CH and/or CL domain using standard molecular biological techniques. Nucleic acid molecules encoding the full-length heavy and/or light chains may then be expressed from a cell into which they have been introduced and the anti-MET antibody isolated.

The nucleic acid molecules may be used to recombinantly express large quantities of anti-MET antibodies. The nucleic acid molecules also may be used to produce chimeric antibodies, bispecific antibodies, single chain antibodies, immunoadhesins, diabodies, mutated antibodies and antibody derivatives, as described herein.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-MET antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of the anti-MET antibodies or antigen-binding portions thereof of the invention as described herein.

In another embodiment, the nucleic acid molecules and vectors may be used to make mutated anti-MET antibodies. The antibodies may be mutated in the variable domains of the heavy and/or light chains, e.g., to alter a binding property of the antibody. For example, a mutation may be made in one or more of the CDR regions to increase or decrease the $K_D$ of the anti-MET antibody, to increase or decrease $k_{off}$, or to alter the binding specificity of the antibody. In another embodiment, one or more mutations are made at an amino acid residue that is known to be changed compared to the germline in a monoclonal antibody of the invention. The mutations may be made in a CDR region or framework region of a variable domain, or in a constant domain. In a preferred embodiment, the mutations are made in a variable domain. In some embodiments, one or more mutations are made at an amino acid residue that is known to be changed compared to the germline in a CDR region or framework region of a variable domain of an antibody or antigen-binding portion thereof of the invention.

In another embodiment, the framework region(s) are mutated so that the resulting framework region(s) have the amino acid sequence of the corresponding germline gene. A mutation may be made in a framework region or constant domain to increase the half-life of the anti-MET antibody. See, e.g., PCT Publication WO 00/09560. A mutation in a framework region or constant domain also can be made to alter the immunogenicity of the antibody, and/or to provide a site for covalent or non-covalent binding to another molecule. According to the invention, a single antibody may have mutations in any one or more of the CDRs or framework regions of the variable domain or in the constant domain.

In some embodiments, the anti-MET antibodies of the invention or antigen-binding portions thereof are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene may be ligated into a vector such that transcriptional and translational control sequences within the vector serve their intended function of regulating the transcription and translation of the antibody gene. The expression vector and expression control sequences may be chosen to be compatible with the expression host cell used. The antibody light chain gene and the antibody heavy chain gene can be inserted into separate vectors. In one embodiment, both genes are inserted into the same expression vector. The antibody genes may be inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can easily be inserted and expressed, as described above. In such vectors, splicing usually occurs between the splice donor site in the inserted J region and the splice acceptor site preceding the human C domain, and also at the splice regions that occur within the human CH exons. Polyadenylation and transcription termination may occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants, are known in the art. See, e.g., U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Hybridoma Methods of Producing Antibodies and Antibody Compositions of the Invention In certain embodiments, the invention provides methods for producing a cell line that produces a human monoclonal antibody or an antigen-binding portion thereof directed against MET, comprising (a) immunizing a non-human transgenic animal with MET, a portion of MET or a cell or tissue expressing MET; (b) allowing the transgenic animal to mount an immune response to MET; (c) isolating antibody-producing cells from the transgenic animal; (d) immortalizing the antibody-producing cells; (e) creating individual monoclonal populations of the immortalized antibody-producing cells; and (f) screening the immortalized antibody-producing cells to identify an antibody directed against MET.

In another aspect, the invention provides a cell line that produces a human anti-MET antibody. In some embodiments the cell line is a hybridoma cell line. In some embodiments, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

In another embodiment, a transgenic animal is immunized with an MET antigen, primary cells, e.g., spleen or peripheral blood B cells, are isolated from the immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable domain sequences, e.g., degenerate primers that recognize most or all of the FR1 regions of human heavy and light chain variable domain genes and anti-sense primers that anneal to constant or joining region sequences. cDNAs of the heavy and light chain variable domains are then cloned and expressed in any suitable host cell, e.g., a myeloma cell, as chimeric antibodies with respective immunoglobulin constant regions, such as the heavy chain and κ or λ constant domains. See Babcook et al., *Proc Natl Acad Sci USA* 93:7843-48 (1996). Anti-MET antibodies may then be identified and isolated as described herein.

Phage Display Libraries

The invention provides a method for producing an anti-MET antibody or antigen-binding portion thereof comprising the steps of synthesizing a library of human antibodies on phage, screening the library with MET or an antibody-binding portion thereof, isolating phage that bind to MET, and obtaining the antibody from the phage. By way of example, one method for preparing the library of antibodies for use in phage display techniques comprises the steps of immunizing a non-human animal with MET or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-MET antibodies of the invention may be obtained in this way.

Recombinant human anti-MET antibodies of the invention can be isolated by screening a recombinant combinatorial antibody library. Preferably the library is a scFv phage display library, generated using human VL and VH cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publications. WO 92/18619, WO 91/17271, WO 92/20791, WO 92/15679, WO 93/01288, WO 92/01047, and WO 92/09690; Fuchs et al., *Bio/Technology* 9:1370-1372 (1991); Hay et al., *Hum Antibod Hybridomas* 3:81-85 (1992); Huse et al., *Science* 246:1275-1281 (1989); McCafferty et al., *Nature* 348:552-554 (1990); Griffiths et al., *EMBO J* 12:725-734 (1993); Hawkins et al., *J Mol Biol* 226:889-896 (1992); Clackson et al., *Nature* 352:624-628 (1991); Gram et al., *Proc Natl Acad Sci USA*

89:3576-3580 (1992); Garrad et al., *Bio/Technology* 9:1373-1377 (1991); Hoogenboom et al., *Nuc Acid Res* 19:4133-4137 (1991); and Barbas et al., *Proc Natl Acad Sci USA* 88:7978-7982 (1991), all incorporated herein by reference.

In one embodiment, to isolate and produce human anti-MET antibodies with the desired characteristics, a human anti-MET antibody as described herein is first used to select human heavy and light chain sequences having similar binding activity toward MET, using the epitope imprinting methods described in PCT Publication WO 93/06213, incorporated herein by reference. The antibody libraries used in this method are preferably scFv libraries prepared and screened as described in PCT Publication WO 92/01047, McCafferty et al., *Nature* 348:552-554 (1990); and Griffiths et al., *EMBO J* 12:725-734 (1993), all incorporated herein by reference. The scFv antibody libraries preferably are screened using human MET as the antigen.

Once initial human VL and VH domains are selected, "mix and match" experiments can be performed, in which different pairs of the initially selected VL and VH segments are screened for MET binding to select preferred VL/VH pair combinations. Additionally, to further improve the quality of the antibody, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL domains using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be re-screened for binding to MET.

Following screening and isolation of an anti-MET antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described herein. To express a recombinant human antibody isolated by screening of a combinatorial library, the DNA encoding the antibody is cloned into a recombinant expression vector and introduced into a mammalian host cell, as described herein.

Non-Hybridoma Host Cells and Methods of Antibody and Antibody Composition Production An additional aspect of the invention relates to methods for producing the antibody compositions and antibodies and antigen-binding portions thereof of the invention. One embodiment of this aspect of the invention relates to a method for producing an antibody as defined herein, comprising providing a recombinant host cell capable of expressing the antibody, cultivating said host cell under conditions suitable for expression of the antibody, and isolating the resulting antibody. Antibodies produced by such expression in such recombinant host cells are referred to herein as "recombinant antibodies". The invention also provides progeny cells of such host cells, and antibodies produced by same.

The term "recombinant host cell" (or simply "host cell"), as used herein, means a cell into which a recombinant expression vector has been introduced. The invention provides host cells that may comprise, e.g., a vector according to the invention described above. The invention also provides host cells that comprise, e.g., a nucleotide sequence encoding the heavy chain or an antigen-binding portion thereof, a nucleotide sequence encoding the light chain or an antigen-binding portion thereof, or both, of an anti-MET antibody or antigen-binding portion thereof of the invention. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-MET antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention or antigen-binding portions thereof from production cell lines can be enhanced using a number of known techniques. For example, the glutamine synthetase gene expression system (the GS system) is a common approach for enhancing expression under certain conditions. The GS system is discussed in whole or part in connection with EP patents 0 216 846, 0 256 055, 0 323 997 and 0 338 841.

It is likely that antibodies expressed by different cell lines or in transgenic animals will have different glycosylation patterns from each other. However, all antibodies encoded by the nucleic acid molecules provided herein, or comprising the amino acid sequences provided herein are part of the instant invention, regardless of the glycosylation state of the antibodies, and more generally, regardless of the presence or absence of post-translational modification(s).

In a further embodiment, the invention relates to a method for producing an antibody composition comprising at least two anti-MET antibodies, the method comprising:

providing at least first and second host cells, wherein the first host cell is capable of expressing a first anti-MET antibody of the invention and the second host cell is capable of expressing a second anti-MET antibody of the invention;

cultivating the first and second host cells under conditions suitable for expression of the anti-MET antibodies; and isolating the resulting antibodies.

An antibody or antigen-binding portion thereof or antibody composition of the present invention may be produced by methods generally known in the art for production of recombinant monoclonal or polyclonal antibodies. Thus, in the case of production of a single antibody of the invention, any method known in the art for production of recombinant monoclonal antibodies may be used. For production of an antibody composition of the invention comprising a mixture of antibodies, the individual antibodies may be produced separately, i.e., each antibody being produced in a separate bioreactor, or the individual antibodies may be produced together in single bioreactor. If the antibody composition is produced in more than one bioreactor, the purified antibody composition can be obtained by pooling the antibodies obtained from individually purified supernatants from each bioreactor. Various approaches for production of a polyclonal antibody composition in multiple bioreactors, where the cell lines or antibody preparations are combined at a later point upstream or prior to or during downstream processing, are described in WO 2009/129814 (incorporated herein by reference).

In the case of producing individual antibodies in a single bioreactor, this may be performed, e.g., as described in WO 2004/061104 or WO 2008/145133 (both of which are incorporated herein by reference). The method described in WO 2004/061104 is based on site-specific integration of the antibody coding sequence into the genome of the individual host cells, while the method of WO 2008/145133 involves an alternative approach using random integration to produce antibodies in a single bioreactor.

Further information regarding methods suitable for preparing the antibodies and compositions of the invention may be found in WO 2012/059857 (incorporated herein by reference).

Transgenic Animals and Plants

Anti-MET antibodies and antigen-binding portions thereof of the invention also can be produced transgenically through the generation of a mammal or plant that is transgenic for the immunoglobulin heavy and light chain sequences of interest and production of the antibody in a recoverable form therefrom. In connection with transgenic production in mammals, anti-MET antibodies and portions can be produced in, and recovered from, the milk of goats, cows, or other mammals. See, e.g., U.S. Pat. Nos. 5,827,690, 5,756,687, 5,750,172, and 5,741,957. In some embodiments, non-human transgenic animals that comprise human immunoglobulin loci are immunized with human MET or an immunogenic portion thereof, as described above. Methods for making antibodies in plants are described, e.g., in U.S. Pat. Nos. 6,046,037 and 5,959,177.

In some embodiments, non-human transgenic animals or plants are produced by introducing one or more nucleic acid molecules encoding an anti-MET antibody or antigen-binding portion thereof of the invention (e.g., any of the above-described nucleic acid molecules encoding an anti-MET antibody or antigen-binding portion thereof) into the animal or plant by standard transgenic techniques. See, e.g., U.S. Pat. No. 6,417,429. The transgenic cells used for making the transgenic animal can be embryonic stem cells or somatic cells or a fertilized egg. The transgenic non-human organisms can be chimeric, nonchimeric heterozygotes, and non-chimeric homozygotes. See, e.g., Hogan et al., *Manipulating the Mouse Embryo: A Laboratory Manual* $2^{nd}$ ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999). In some embodiments, the transgenic non-human animals have a targeted disruption and replacement by a targeting construct that encodes a heavy chain and/or a light chain of interest. The non-human transgenic animals or plants may comprise, e.g., a nucleotide sequence encoding the heavy chain or an antigen-binding portion thereof, a nucleotide sequence encoding the light chain or an antigen-binding portion thereof, or both, of an anti-MET antibody of the invention. In a preferred embodiment, the transgenic animals comprise and express nucleic acid molecules encoding heavy and light chains, or antigen-binding portions thereof, that specifically bind to human MET. The anti-MET antibodies or portions may be made in any transgenic animal. In a preferred embodiment, the non-human animals are mice, rats, sheep, pigs, goats, cattle or horses. The non-human transgenic animal may express said encoded polypeptides in, e.g., blood, milk, urine, saliva, tears, mucus and other bodily fluids.

Pharmaceutical Compositions

Another aspect of the invention is a pharmaceutical composition comprising as an active ingredient (or as the sole active ingredient) an anti-MET antibody or antigen-binding portion thereof or anti-MET antibody composition of the invention. The pharmaceutical composition may comprise any anti-MET antibody composition or antibody or antigen-binding portion thereof as described herein. In some embodiments, the compositions are intended for amelioration, prevention, and/or treatment of a MET-mediated disorder (e.g., a disorder characterized by overexpression of MET) and/or cancer. In certain embodiments, the compositions are intended for amelioration, prevention, and/or treatment of non-small cell lung cancer, gastric cancer, hepatocellular carcinoma, esophageal cancer, colorectal cancer, kidney papillary cell cancer, glioblastoma, renal cell carcinoma, prostate cancer, and/or adrenocortical carcinoma.

Generally, the antibodies of the invention or antigen-binding portions thereof are suitable to be administered as a formulation in association with one or more pharmaceutically acceptable excipient(s). The term "excipient" is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in *Remington's Pharmaceutical Sciences*, 19th Edition (Mack Publishing Company, 1995). Pharmaceutical compositions are preferably manufactured under GMP (good manufacturing practices) conditions.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and antigen-binding portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Regional perfusion is also contemplated. Preferred embodiments include the intravenous and the subcutaneous routes.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-MET antibody or antigen-binding portion thereof or anti-MET antibody composition in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin, and/or by using modified-release coatings (e.g., slow-release coatings).

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the antibody of the invention per actuation and the actuation volume may for example vary from 1 µL to 100 µL.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Immunoconjugates

Another option for therapeutic use of the antibody compositions and antibodies and antigen-binding portions thereof of the invention is in the form of immunoconjugates, i.e., antibodies or antigen-binding portions conjugated to one or more agents such as anti-cancer agents. Compositions of the invention comprising two or more anti-MET antibodies may contain a single antibody in the form of an immunoconjugate, or they may contain two or more antibodies in the form of an immunoconjugate.

Various types of anti-cancer agents may be conjugated to the antibodies of the invention, including cytotoxic agents (e.g., conventional chemotherapy agents and other small molecule anti-cancer drugs), cytokines (in which case the conjugate may be termed an "immunocytokine"), toxins (in which case the conjugate may be termed an "immunotoxin") and radionuclides. A few immunoconjugates have already been approved for clinical use. These include Zevalin® (a murine anti-CD20 antibody conjugated to $^{90}$Y), Bexxar® (a murine anti-CD20 antibody conjugated to $^{131}$I) and Mylotarg® (a humanized anti-CD33 antibody conjugated to calicheamicin). Other immunoconjugates that have been tested in clinical trials include antibodies conjugated to, e.g., doxorubicin or a maytansinoid compound. Immunotoxins that have been tested in clinical trials include several antibodies conjugated to a truncated *Pseudomonas* exotoxin A. An immunocytokine comprising a humanized EpCAM antibody conjugated to IL-2 has also been tested.

In the case of antibodies of the invention conjugated to cytotoxic agents, these may belong, e.g., to any of the major classes of chemotherapy drugs, including alkylating agents (e.g., carboplatin, cisplatin, oxaliplatin), antimetabolites (e.g., methotrexate, capecitabine, gemcitabine), anthracyclines (e.g., bleomycin, doxorubicin, mitomycin-C) and plant alkaloids (e.g., taxanes such as docetaxel and paclitaxel, and *vinca* alkaloids such as vinblastine, vincristine and vinorelbine). Since the use of immunoconjugates specifically directs the anti-cancer agent to the tumors, immunoconjugates based on the antibodies of the invention may advantageously be based on highly cytotoxic agents such as calicheamicin or maytansine derivatives, or on toxins such as bacterial toxins (e.g., *Pseudomonas* exotoxin A, diphtheria toxin) or plant toxins (e.g., ricin).

The conjugated anti-cancer agent in an immunoconjugate is generally linked to the antibody by means of a labile linker that is relatively stable in serum but which allows release of the agent when the immunoconjugate is internalized into the target cell. Suitable linkers include, for example, chemical linkers that are stable at neutral pH in serum but are subjected to acid hydrolysis in the mildly acidic conditions within the lysosomes subsequent to internalization, disulfide linkers that are cleaved by intracellular thiols, and peptide linkers that are stable in serum but which are subjected to enzymatic cleavage in intracellular compartments.

Various conjugation arrangements can be envisioned in compositions containing two or more antibodies of the invention. For example, with two antibodies it would be possible to conjugate the antibodies to two or more different anti-cancer drugs or to conjugate one antibody to a prodrug which is activated by an agent such as an enzyme conjugated to the other antibody. The general concept of antibody-directed enzyme prodrug therapy (ADEPT) has been described for monoclonal antibodies, where a prodrug is activated by an enzyme targeted to the tumor by an mAB-enzyme conjugate, but the present invention may provide an opportunity for tailoring this approach to particular conditions. It may thus be possible to specifically increase tumor cell killing while sparing or reducing damage to normal tissues.

For further information on anti-cancer immunoconjugates, see Wu et al., *Nature Biotechnology* 23(9):1137-1146 (2005); Schrama et al., *Nature Reviews/Drug Discovery* 5:147-159 (2006); and Rohrer, *Chimica Oggi/Chemistry Today* 27(5):56-60 (2009).

Therapeutic Uses of Antibodies and Compositions of the Invention

In one aspect, the anti-MET antibodies and antigen-binding portions thereof and anti-MET compositions of the invention are used in the treatment of a MET-mediated disorder. In some embodiments, the MET-mediated disorder is a condition characterized by overexpression of MET. In certain embodiments, the pharmaceutical composition is for use in the treatment of cancer, e.g., non-small cell lung cancer, gastric cancer, hepatocellular carcinoma, esophageal cancer, colorectal cancer, kidney papillary cell cancer, glioblastoma, adrenocortical carcinoma, renal cell carcinoma, prostate cancer, and other cancers that express or overexpress MET or rely on MET pathway activation.

In some aspects, the antibodies or antibody compositions are used to treat a disorder, such as a cancer, characterized by abnormal MET overactivity. In some embodiments, the abnormal overactivity stems from gene amplification, protein overexpression, a MET activating gene mutation (e.g., a point mutation or abnormal gene splicing event), or HGF overexpression.

In certain aspects, the anti-MET antibodies and antigen-binding portions thereof and anti-MET compositions of the invention may be used to treat a patient who is resistant to treatment with an agent targeting a different tyrosine kinase receptor. In some embodiments, the patient is resistant to treatment with an ErbB kinase inhibitor. In certain embodiments, the ErbB kinase inhibitor targets EGFR, ErbB2, ErbB3, or ErbB4. In a particular embodiment, the ErbB kinase inhibitor targets EGFR. In another embodiment, the ErbB kinase inhibitor targets HER3. The ErbB kinase inhibitor may be selected from, e.g., gefitinib, erlotinib, cetuximab, pantinumumab, trastuzumab, or any combination thereof.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

"Therapeutically effective amount" refers to that amount of the therapeutic agent being administered which will relieve to some extent one or more of the symptoms of the disorder being treated.

The ratio between the individual antibodies in a therapeutic composition of the invention, or in the case of individual antibodies of the invention being administered simultaneously, sequentially or separately, will often be such that the antibodies are administered in equal amounts, but this need not necessarily be the case. Thus, a composition of the invention comprising two anti-MET antibodies or antigen-binding portions thereof will often contain them in approximately a 1:1 ratio, but depending on the characteristics of the individual antibodies, it may be desirable to use non-equal amounts of the antibodies or portions. For example, the ratio of one antibody or portion relative to another antibody or portion in a two-antibody composition may be, e.g., between 5 and 95%, between 10 and 90%, between 20 and 80%, between 30 and 70%, between 40 and 60%, or between 45 and 55%.

The antibody compositions or antibodies or antigen-binding portions thereof of the invention may be administered alone or in combination with one or more other drugs or antibodies (or as any combination thereof). The pharmaceutical compositions, methods and uses of the invention thus also encompass embodiments of combinations (co-administration) with other active agents, as detailed below.

As used herein, the terms "co-administration", "co-administered" and "in combination with," referring to the antibody compositions and antibodies and antigen-binding portions thereof with one or more other therapeutic agents, is intended to mean, and does refer to and include the following:

simultaneous administration of such combination of antibody composition/antibody/antigen-binding portion of the invention and therapeutic agent(s) to a patient in need of treatment, when such components are formulated together into a single dosage form which releases said components at substantially the same time to said patient, substantially simultaneous administration of such combination of antibody composition/antibody/antigen-binding portion of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination of antibody composition/antibody/antigen-binding portion of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of antibody composition/antibody/antigen-binding portion of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The antibody compositions and antibodies and antigen-binding portions thereof of the invention may be administered without additional therapeutic treatments, i.e., as a stand-alone therapy. Alternatively, treatment with the antibody compositions and antibodies and antigen-binding portions thereof of the invention may include at least one additional therapeutic treatment (combination therapy). In some embodiments, the antibody composition or antibody or antigen-binding portion thereof may be co-administered or formulated with another medication/drug for the treatment of cancer. The additional therapeutic treatment may comprise, e.g., a chemotherapeutic, anti-neoplastic, or anti-angiogenic agent, a different anti-cancer antibody, and/or radiation therapy.

By combining the antibody compositions, antibodies, or antigen-binding portions of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. In some embodiments, the compound is selected from the group consisting of retinoic acid, phenylbutyrate, all-trans-retinoic acid and active form vitamin D.

Pharmaceutical articles comprising an anti-MET antibody composition or anti-MET antibody or antigen-binding portion thereof of the invention and at least one other agent (e.g., a chemotherapeutic, anti-neoplastic, or anti-angiogenic agent) may be used as a combination treatment for simultaneous, separate or successive administration in cancer therapy. The other agent may by any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; and/or antimetabolites, e.g., fluorouracil and/or other fluoropyrimidines.

It is also contemplated that an anti-MET antibody or antigen-binding portion thereof or anti-MET antibody composition of the invention may be used in adjunctive therapy in connection with tyrosine kinase inhibitors. These are synthetic, mainly quinazoline-derived, low molecular weight molecules that interact with the intracellular tyrosine kinase domain of receptors and inhibiting ligand-induced receptor phosphorylation by competing for the intracellular Mg-ATP binding site. Pharmaceutical articles comprising an antibody composition of the invention and at least one TKI targeting MET thus may also be used as a combination treatment for simultaneous, separate or successive administration in cancer therapy.

In certain aspects, the antibody compositions and antibodies and antigen-binding portions thereof of the invention may be administered in combination with another inhibitor of the MET pathway, which may target MET or HGF. In some embodiments, the inhibitor is selected from the group consisting of, but not limited to, AMG 102, AMG 208, AMG 458, ARQ 197, AV299, BAY-853474, CGEN241, DN30, E7050, EMD 1204831, EMD 1214063, INCB28060, JNJ38877605, K252a, LY-2875358, MGCD265, MK-2461, MP-470, NK4, OA-5D5, PF-02341066, PF-04217903, PF-02341066, PHA-665752, SGX-523, SU5416, SU11274, TAK701, XL184, XL880, cabozantinib, crizotinib, ficlatuzumab, foretinib, golvatinib, onartuzumab, rilotumumab, and tivantinib.

In some embodiments, the antibody compositions and antibodies and antigen-binding portions thereof of the invention may be administered in combination with an ErbB inhibitor (such as gefitinib or erlotinib) or a heat shock protein 90 (hsp90) inhibitor (such as 17-AAG).

In other embodiments, the antibody compositions and antibodies and antigen-binding portions thereof of the invention may be used in combination with other antibody therapeutics, e.g., an antibody against VEGF (e.g., Avastin®). In yet other embodiments, the antibody compositions of the present invention may be used in combination with an agent known to stimulate cells of the immune system, such combination treatment leading to enhanced immune-mediated enhancement of the efficacy of the antibody compositions of the invention. Examples of such immune-stimulating agents include recombinant interleukins (e.g., IL-21 and IL-2).

It is understood that the antibody compositions and antibodies and antigen-binding portions thereof of the invention may be used in a method of treatment as described above, may be for use in a treatment as described above, and/or may be for use in the manufacture of a medicament for a treatment as described above, Dose and Route of Administration The antibody compositions of the invention will be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

It is contemplated that a suitable dose of an antibody composition of the invention will be in the range of 0.1-100 mg/kg, such as about 0.5-50 mg/kg, e.g., about 1-20 mg/kg. The antibody composition may for example be administered in a dosage of at least 0.25 mg/kg, e.g., at least 0.5 mg/kg, such as at least 1 mg/kg, e.g., at least 1.5 mg/kg, such as at least 2 mg/kg, e.g., at least 3 mg/kg, such as at least 4 mg/kg, e.g., at least 5 mg/kg; and e.g., up to at most 50 mg/kg, such as up to at the most 30 mg/kg, e.g., up to at the most 20 mg/kg, such as up to at the most 15 mg/kg. Administration will normally be repeated at suitable intervals, e.g., once every week, once every two weeks, once every three weeks, or once every four weeks, and for as long as deemed appropriate by the responsible doctor, who may optionally increase or decrease the dosage as necessary.

An effective amount for tumor therapy may be measured by its ability to stabilize disease progression and/or ameliorate symptoms in a patient, and preferably to reverse disease progression, e.g., by reducing tumor size. The ability of an antibody or composition of the invention to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

Diagnostic Uses and Compositions

The antibodies of the present invention also are useful in diagnostic processes (e.g., in vitro, ex vivo). For example, the antibodies can be used to detect and/or measure the level of MET in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassay, and immunohistology. The invention further encompasses kits (e.g., diagnostic kits) comprising the antibodies described herein.

In order that this invention may be better understood, the following examples are set forth. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

EXAMPLES

Example 1: Cloning of Anti-MET Antibodies

Anti-MET antibodies were obtained using the Symplex™ procedure essentially as described in WO 2005/042774. Briefly, BALB/c, C57 and C3H mice were immunized bi-weekly with human cancer cell lines over-expressing MET (HCT-116), recombinant human MET protein (Sino Biologicals), recombinant human MET protein pre-incubated with ligand (HGF), or trypsin-digested MET. Murine plasma cells obtained from spleens and inguinal lymph nodes were FACS sorted, and linkage of VH and VL coding sequences was performed on the sorted plasma cells, facilitating cognate pairing of the sequences, utilizing a two-step PCR procedure based on a one-step multiplex overlap-extension RT-PCR followed by nested PCR. The principle for linkage of cognate VH and VL sequences is described in detail in WO 2005/042774 and in Meijer et al., *J Mol Biol* 358(3):764-72 (2006).

In order to identify antibodies with binding specificity to MET, the VH and VL coding sequences obtained above were expressed as full-length antibodies. This involved insertion of the repertoire of VH and VL coding pairs into an expression vector and transfection into a host cell using the method described in WO 2012/059858.

The specificity of the produced antibodies was determined by ELISA using as antigen either the extracellular domain of the MET protein or the extracellular domain of the MET protein translationally fused to a human immunoglobulin Fc domain. Nunc MaxiSorp plates (Cat. No. 464718) were coated with 1 µg/ml of the recombinant MET protein diluted in PBS at 4° C. overnight. The plates were washed once with PBS+0.05% Tween 20 (PBS-T) prior to blocking in 50 µl 2% Milk-PBS-T. The plates were washed once again with PBS-T, then 20 µl of 2% milk-PBS-T. 10 µl of supernatants from the FreeStyle293 transfectants were added and incubated for 1 hour at room temperature, after which the plates were washed once with PBS-T. Secondary antibody (HRP-Goat-anti-human kappa light chain, Serotec, Cat. No. STAR 100P) diluted 1:25000 in 2% milk-PBS-T was added to detect the antibodies bound to the wells and incubated for 1 hour at room temperature. The plates were washed once in PBS-T before addition of 25 µl substrate (Kem-En-Tec Diagnostics, Cat. No. 4518) and incubation for 5 min. 25 µl 1M sulphuric acid was added after the incubation to stop the reaction. Specific signal was detected on an ELISA reader at 450 nm. From the ELISA data, positive antibody clones were identified and selected for sequence analysis and validation of binding to MET.

Example 2: Screening of Functional Anti-MET Antibody Mixtures

This example describes in vitro testing of chimeric monoclonal antibodies targeting MET and mixtures of these monoclonal antibodies to identify lead candidates. The monoclonal antibodies and mixtures were evaluated for their ability to inhibit the growth of the cancer cell lines EBC1, MKN45, OE33 and SNU5.

Methods

Mouse-derived antibodies targeting human MET were assayed for their ability to inhibit growth of human cancer cell lines in vitro. The monoclonal antibodies and 2-antibody mixtures (1:1 mixtures of two monoclonal antibodies) were diluted to a final total antibody concentration of 100 µg/ml in RPMI 1640 Glutamax media supplemented with 2% FBS and 1% P/S, yielding a final concentration of 5 µg/ml. Relevant numbers of cells (EBC1: 1500 cells/well, MKN45: 2000 cells/well, OE33 4300 cells/well and SNU5: 800 cells/well) were then added to the experimental wells in a 384 well plate, and incubated with antibodies for 4 days in a humidified incubator at 37° C. WST-1 reagent was subsequently added to the plates, and incubated for one hour at 37° C. The absorbance was measured at 450 nm and 620 nm (reference wavelength) using an ELISA reader. The absorbance at 620 nM was subtracted from the absorbance at 450 nM. The amount of metabolically active cells (MAC) was calculated as a percentage of the untreated control as follows:

$$\% \ MAC = \left( \frac{QDexp. - QDMedia}{ODuntreat. - QDMedia} \right) \times 100$$

It is assumed that the metabolic activity correlates with the number of viable cells, meaning that a lower % MAC corresponds to a higher level of cell growth inhibition by the antibodies.

Results

Antibody mixtures were ranked based on their ability to inhibit cell growth among a panel of cancer cell lines. The viability results from monoclonal antibodies and mixtures of two antibodies on the metabolic activity of cell lines EBC1, MKN45, OE33 and SNU5 are shown in Table 3. Seven different mixtures of two antibodies inhibit metabolic activity to an average below 50%.

Among the most efficacious mixtures, the combination of the two antibodies 9006 and 9338 exhibited a broad cell growth inhibitory activity. Interestingly, each antibody alone exhibited lower efficacy than the combination, suggesting that the two antibodies can act synergistically. In addition to 9006+9338, it may be seen from Table 3 that other highly efficacious mixtures include 9206+9232, 8955+9338, 9206+9338, 9006+9232, 8955+9006, 8955+9096 and 8955+9232. Further, it will be apparent that these top eight mixtures are based on relatively few individual monoclonal antibodies, in particular 8955, 9006, 9232, 9338 and 9206.

TABLE 3

Anti-proliferative effect of monoclonal antibodies and antibody mixtures

| mAb or mAb mixture | Sequence Cluster(s) | Metabolic activty of cells treated with mAb or mAb mixture (% of untreated control) | | | | | |
|---|---|---|---|---|---|---|---|
| | | SNU5 | OE33 | MKN45 | EBC1 | Average | Rank |
| 9206 + 9232 | 008 + 007 | 32 | 70 | 32 | 37 | 43 | 1 |
| 9006 + 9338 | 018 + 004 | 33 | 54 | 31 | 54 | 43 | 2 |
| 8955 + 9338 | 029 + 004 | 33 | 60 | 24 | 63 | 45 | 3 |
| 9206 + 9338 | 008 + 004 | 39 | 52 | 34 | 55 | 45 | 4 |
| 9006 + 9232 | 018 + 007 | 36 | 72 | 24 | 59 | 48 | 5 |
| 8955 + 9006 | 029 + 018 | 46 | 62 | 25 | 61 | 48 | 6 |
| 8955 + 9096 | 029 + 018 | 55 | 41 | 40 | 59 | 49 | 7 |
| 8955 + 9232 | 029 + 007 | 46 | 66 | 25 | 69 | 51 | 8 |
| 9206 + 9217 | 008 + 012 | 35 | 60 | 54 | 99 | 62 | 9 |
| 8955 + 9206 | 029 + 008 | 39 | 71 | 57 | 82 | 62 | 10 |
| 9044 + 9111 | 011 + 009 | 47 | 77 | 37 | 91 | 63 | 11 |
| 9111 + 9217 | 009 + 012 | 40 | 101 | 24 | 93 | 64 | 12 |
| 9111 + 9232 | 009 + 007 | 67 | 83 | 53 | 63 | 66 | 13 |
| 9006 + 9111 | 018 + 009 | 31 | 101 | 36 | 98 | 66 | 14 |
| 9111 + 9206 | 009 + 008 | 39 | 79 | 53 | 96 | 67 | 15 |
| 9006 + 9154 | 018 + 009 | 34 | 91 | 49 | 98 | 68 | 16 |
| 9096 + 9232 | 018 + 007 | 50 | 79 | 54 | 94 | 69 | 17 |
| 9184 + 9217 | 009 + 012 | 45 | 103 | 30 | 101 | 70 | 18 |
| 9184 + 9206 | 009 + 008 | 30 | 88 | 63 | 97 | 70 | 19 |
| 9173 + 9232 | 028 + 007 | 51 | 90 | 84 | 57 | 71 | 20 |
| 9006 + 9184 | 018 + 009 | 35 | 105 | 44 | 107 | 73 | 21 |
| 9154 + 9217 | 009 + 012 | 52 | 98 | 36 | 105 | 73 | 22 |
| 9212 + 9232 | 025 + 007 | 57 | 92 | 90 | 64 | 76 | 23 |
| 9154 + 9206 | 009 + 008 | 48 | 66 | 87 | 103 | 76 | 24 |
| 9096 + 9184 | 018 + 009 | 47 | 80 | 71 | 108 | 76 | 25 |
| 9096 + 9111 | 018 + 009 | 43 | 107 | 65 | 94 | 77 | 26 |
| 9173 + 9340 | 028 + 072 | 40 | 98 | 79 | 98 | 79 | 27 |
| 9044 + 9184 | 011 + 009 | 57 | 104 | 54 | 102 | 79 | 28 |
| 9184 + 9232 | 009 + 007 | 92 | 100 | 62 | 63 | 79 | 29 |
| 9111 + 9173 | 009 + 028 | 47 | 103 | 69 | 103 | 80 | 30 |
| 9111 + 9133 | 009 + 028 | 54 | 103 | 64 | 106 | 82 | 31 |
| 9006 + 9122 | 018 + 031 | 46 | 112 | 50 | 118 | 82 | 32 |
| 9096 + 9338 | 018 + 004 | 50 | 57 | 100 | 120 | 82 | 33 |
| 9173 | 028 | 38 | 99 | 83 | 108 | 82 | 34 |
| 9006 + 9146 | 018 + 036 | 61 | 75 | 79 | 118 | 83 | 35 |
| 9146 + 9173 | 036 + 028 | 48 | 115 | 66 | 105 | 83 | 36 |
| 9173 + 9184 | 028 + 009 | 44 | 113 | 70 | 108 | 84 | 37 |
| 8820 + 9006 | 044 + 018 | 55 | 103 | 65 | 115 | 85 | 38 |
| 9044 + 9154 | 011 + 009 | 59 | 100 | 67 | 113 | 85 | 39 |
| 8908 + 9006 | 032 + 018 | 42 | 110 | 50 | 138 | 85 | 40 |
| 9173 + 9206 | 028 + 008 | 47 | 107 | 74 | 112 | 85 | 41 |
| 9173 + 9212 | 028 + 025 | 46 | 99 | 93 | 102 | 85 | 42 |
| 9133 + 9232 | 028 + 007 | 77 | 110 | 88 | 66 | 85 | 43 |
| 9044 + 9206 | 011 + 008 | 89 | 65 | 83 | 107 | 86 | 44 |
| 9146 + 9232 | 036 + 007 | 105 | 90 | 86 | 65 | 86 | 45 |
| 8955 + 9111 | 029 + 009 | 73 | 96 | 61 | 117 | 87 | 46 |
| 9006 + 9173 | 018 + 028 | 43 | 109 | 84 | 113 | 87 | 47 |
| 9154 + 9173 | 009 + 028 | 55 | 104 | 79 | 112 | 88 | 48 |
| 9154 + 9232 | 009 + 007 | 94 | 115 | 73 | 70 | 88 | 49 |
| 9006 + 9212 | 018 + 025 | 61 | 79 | 94 | 120 | 88 | 50 |
| 9096 + 9154 | 018 + 009 | 73 | 82 | 83 | 115 | 88 | 51 |
| 9006 | 018 | 68 | 73 | 90 | 122 | 88 | 52 |
| 9122 + 9206 | 031 + 008 | 67 | 110 | 56 | 125 | 89 | 53 |
| 8820 + 8955 | 044 + 029 | 87 | 87 | 80 | 106 | 90 | 54 |
| 8908 + 9217 | 032 + 012 | 74 | 96 | 65 | 125 | 90 | 55 |
| 9006 + 9096 | 018 + 018 | 68 | 71 | 90 | 131 | 90 | 56 |
| 9133 + 9212 | 028 + 025 | 59 | 96 | 102 | 104 | 90 | 57 |
| 9122 + 9232 | 031 + 007 | 117 | 86 | 95 | 62 | 90 | 58 |
| 9006 + 9133 | 018 + 028 | 58 | 111 | 81 | 113 | 90 | 59 |
| 8955 + 9007 | 029 + 046 | 83 | 81 | 98 | 100 | 91 | 60 |

TABLE 3-continued

Anti-proliferative effect of monoclonal antibodies and antibody mixtures

| mAb or mAb mixture | Sequence Cluster(s) | Metabolic activty of cells treated with mAb or mAb mixture (% of untreated control) | | | | | |
|---|---|---|---|---|---|---|---|
| | | SNU5 | OE33 | MKN45 | EBC1 | Average | Rank |
| 8908 + 8955 | 032 + 029 | 79 | 70 | 87 | 128 | 91 | 61 |
| 9096 + 9173 | 018 + 028 | 39 | 119 | 88 | 117 | 91 | 62 |
| 9133 + 9173 | 028 + 028 | 45 | 102 | 116 | 102 | 91 | 63 |
| 9217 + 9232 | 012 + 007 | 114 | 100 | 82 | 68 | 91 | 64 |
| 8955 + 9146 | 029 + 036 | 83 | 72 | 92 | 118 | 91 | 65 |
| 9122 + 9217 | 031 + 012 | 65 | 126 | 46 | 128 | 91 | 66 |
| 8955 + 9154 | 029 + 009 | 80 | 80 | 85 | 122 | 92 | 67 |
| 9133 + 9184 | 028 + 009 | 58 | 112 | 85 | 111 | 92 | 68 |
| 9006 + 9044 | 018 + 011 | 66 | 75 | 91 | 135 | 92 | 69 |
| 8955 + 8958 | 029 + 029 | 72 | 94 | 81 | 121 | 92 | 70 |
| 8820 + 9111 | 044 + 009 | 61 | 135 | 53 | 120 | 92 | 71 |
| 8955 + 9122 | 029 + 031 | 69 | 91 | 81 | 129 | 93 | 72 |
| 9096 + 9133 | 018 + 028 | 57 | 99 | 95 | 120 | 93 | 73 |
| 9006 + 9217 | 018 + 012 | 67 | 93 | 92 | 120 | 93 | 74 |
| 9111 + 9122 | 009 + 031 | 98 | 106 | 50 | 118 | 93 | 75 |
| 9146 + 9184 | 036 + 009 | 89 | 93 | 81 | 110 | 93 | 76 |
| 9212 + 9340 | 025 + 072 | 69 | 117 | 86 | 99 | 93 | 77 |
| 8820 + 9232 | 044 + 007 | 88 | 103 | 75 | 108 | 93 | 78 |
| 9146 + 9206 | 036 + 008 | 79 | 75 | 101 | 119 | 94 | 79 |
| 9044 + 9122 | 011 + 031 | 80 | 109 | 63 | 124 | 94 | 80 |
| 9006 + 9340 | 018 + 072 | 70 | 78 | 101 | 127 | 94 | 81 |
| 9173 + 9338 | 028 + 004 | 61 | 102 | 92 | 120 | 94 | 82 |
| 8820 + 9184 | 044 + 009 | 67 | 121 | 60 | 128 | 94 | 83 |
| 9006 + 9206 | 018 + 008 | 81 | 78 | 101 | 117 | 94 | 84 |
| 9173 + 9217 | 028 + 012 | 58 | 124 | 72 | 123 | 94 | 85 |
| 9133 + 9206 | 028 + 008 | 67 | 102 | 95 | 112 | 94 | 86 |
| 9006 + 9007 | 018 + 046 | 61 | 92 | 81 | 142 | 94 | 87 |
| 9212 | 025 | 86 | 90 | 101 | 100 | 94 | 88 |
| 9232 + 9338 | 007 + 004 | 86 | 93 | 77 | 122 | 94 | 89 |
| 9133 | 028 | 68 | 102 | 99 | 109 | 95 | 90 |
| 8820 + 9206 | 044 + 008 | 58 | 129 | 69 | 123 | 95 | 91 |
| 8955 + 9340 | 029 + 072 | 81 | 70 | 97 | 133 | 95 | 92 |
| 9111 + 9146 | 009 + 036 | 93 | 108 | 74 | 109 | 96 | 93 |
| 9096 + 9206 | 018 + 008 | 70 | 79 | 98 | 138 | 96 | 94 |
| 9133 + 9146 | 028 + 036 | 67 | 100 | 112 | 106 | 96 | 95 |
| 9096 + 9122 | 018 + 031 | 49 | 121 | 77 | 139 | 96 | 96 |
| 8906 + 9232 | 056 + 007 | 89 | 111 | 74 | 112 | 97 | 97 |
| 9133 + 9340 | 028 + 072 | 69 | 123 | 93 | 101 | 97 | 98 |
| 8908 + 9232 | 032 + 007 | 95 | 100 | 76 | 116 | 97 | 99 |
| 8955 + 9184 | 029 + 009 | 74 | 96 | 87 | 130 | 97 | 100 |
| 9044 + 9232 | 011 + 007 | 85 | 112 | 82 | 110 | 97 | 101 |
| 8955 + 9212 | 029 + 025 | 105 | 75 | 91 | 118 | 97 | 102 |
| 8899 + 8955 | 029 + 029 | 78 | 77 | 97 | 137 | 97 | 103 |
| 9111 + 9212 | 009 + 025 | 89 | 91 | 101 | 109 | 97 | 104 |
| 8820 + 9173 | 044 + 028 | 46 | 158 | 77 | 112 | 98 | 105 |
| 9096 + 9146 | 018 + 036 | 81 | 78 | 101 | 133 | 98 | 106 |
| 9096 + 9212 | 018 + 025 | 83 | 86 | 98 | 127 | 98 | 107 |
| 8955 + 9133 | 029 + 028 | 85 | 96 | 89 | 126 | 99 | 108 |
| 9212 + 9338 | 025 + 004 | 66 | 118 | 93 | 119 | 99 | 109 |
| 8820 + 9338 | 044 + 004 | 90 | 96 | 91 | 119 | 99 | 110 |
| 8906 + 9217 | 056 + 012 | 82 | 106 | 81 | 128 | 99 | 111 |
| 9206 | 008 | 90 | 86 | 97 | 125 | 99 | 112 |
| 8955 + 9173 | 029 + 028 | 69 | 113 | 94 | 123 | 100 | 113 |
| 9007 + 9232 | 046 + 007 | 109 | 99 | 77 | 114 | 100 | 114 |
| 8908 + 9111 | 032 + 009 | 93 | 114 | 79 | 114 | 100 | 115 |
| 9111 + 9184 | 009 + 009 | 88 | 99 | 100 | 115 | 100 | 116 |
| 9007 + 9217 | 046 + 012 | 89 | 97 | 90 | 126 | 100 | 117 |
| 8955 | 029 | 100 | 68 | 101 | 132 | 100 | 118 |
| 9154 + 9184 | 009 + 009 | 90 | 102 | 91 | 119 | 101 | 119 |
| 9122 + 9173 | 031 + 028 | 75 | 131 | 80 | 116 | 101 | 120 |
| 8820 + 9096 | 044 + 018 | 82 | 95 | 86 | 140 | 101 | 121 |
| 9111 + 9154 | 009 + 009 | 93 | 103 | 91 | 117 | 101 | 122 |
| 9096 + 9340 | 018 + 072 | 80 | 81 | 105 | 139 | 101 | 123 |
| 8908 + 9206 | 032 + 008 | 90 | 108 | 80 | 127 | 101 | 124 |
| 9206 + 9212 | 008 + 025 | 91 | 77 | 114 | 124 | 101 | 125 |
| 8820 + 9122 | 044 + 031 | 63 | 158 | 61 | 125 | 102 | 126 |
| 9146 | 036 | 119 | 92 | 100 | 100 | 103 | 127 |
| 9206 + 9340 | 008 + 072 | 103 | 94 | 94 | 120 | 103 | 128 |
| 8906 + 9006 | 056 + 018 | 66 | 142 | 52 | 152 | 103 | 129 |
| 8820 + 9133 | 044 + 028 | 63 | 152 | 80 | 116 | 103 | 130 |
| 8902 + 8955 | 029 + 029 | 72 | 87 | 105 | 149 | 103 | 131 |
| 9232 + 9340 | 007 + 072 | 115 | 93 | 85 | 120 | 103 | 132 |
| 8955 + 9026 | 029 + 029 | 91 | 75 | 101 | 146 | 104 | 133 |

TABLE 3-continued

Anti-proliferative effect of monoclonal antibodies and antibody mixtures

| mAb or mAb mixture | Sequence Cluster(s) | Metabolic activty of cells treated with mAb or mAb mixture (% of untreated control) | | | | | |
|---|---|---|---|---|---|---|---|
| | | SNU5 | OE33 | MKN45 | EBC1 | Average | Rank |
| 9146 + 9212 | 036 + 025 | 110 | 93 | 106 | 106 | 104 | 134 |
| 9111 | 009 | 97 | 96 | 102 | 119 | 104 | 135 |
| 8955 + 9217 | 029 + 012 | 94 | 97 | 91 | 134 | 104 | 136 |
| 8820 + 9154 | 044 + 009 | 72 | 148 | 73 | 123 | 104 | 137 |
| 8906 + 9206 | 056 + 008 | 90 | 126 | 75 | 127 | 104 | 138 |
| 8820 + 9217 | 044 + 012 | 91 | 151 | 65 | 112 | 105 | 139 |
| 9044 + 9217 | 011 + 012 | 103 | 102 | 93 | 120 | 105 | 140 |
| 9232 | 007 | 115 | 100 | 84 | 121 | 105 | 141 |
| 9340 | 072 | 113 | 99 | 95 | 114 | 105 | 142 |
| 9217 + 9338 | 012 + 004 | 83 | 124 | 89 | 126 | 106 | 143 |
| 9096 | 018 | 90 | 86 | 103 | 144 | 106 | 144 |
| 9184 + 9212 | 009 + 025 | 98 | 103 | 108 | 114 | 106 | 145 |
| 9007 + 9173 | 046 + 028 | 67 | 153 | 95 | 109 | 106 | 146 |
| 8908 + 9184 | 032 + 009 | 85 | 127 | 90 | 123 | 106 | 147 |
| 9111 + 9340 | 009 + 072 | 107 | 109 | 101 | 111 | 107 | 148 |
| 9044 + 9133 | 011 + 028 | 91 | 132 | 87 | 119 | 107 | 149 |
| 9133 + 9154 | 028 + 009 | 90 | 123 | 101 | 117 | 108 | 150 |
| 8820 + 9044 | 044 + 011 | 97 | 138 | 79 | 117 | 108 | 151 |
| 8820 + 9212 | 044 + 025 | 82 | 143 | 87 | 119 | 108 | 152 |
| 9122 + 9184 | 031 + 009 | 96 | 140 | 73 | 124 | 108 | 153 |
| 9007 + 9206 | 046 + 008 | 89 | 113 | 95 | 136 | 108 | 154 |
| 9184 | 009 | 101 | 110 | 101 | 123 | 109 | 155 |
| 9338 | 004 | 100 | 98 | 96 | 141 | 109 | 156 |
| 8906 + 9111 | 056 + 009 | 112 | 120 | 84 | 122 | 110 | 157 |
| 9111 + 9338 | 009 + 004 | 107 | 121 | 90 | 121 | 110 | 158 |
| 9146 + 9340 | 036 + 072 | 112 | 137 | 90 | 100 | 110 | 159 |
| 9133 + 9338 | 028 + 004 | 89 | 133 | 96 | 120 | 110 | 160 |
| 8820 + 8906 | 044 + 056 | 86 | 148 | 80 | 126 | 110 | 161 |
| 9217 | 012 | 96 | 108 | 100 | 135 | 110 | 162 |
| 9044 + 9338 | 011 + 004 | 101 | 101 | 103 | 135 | 110 | 163 |
| 8908 + 9154 | 032 + 009 | 98 | 132 | 87 | 124 | 110 | 164 |
| 9007 + 9096 | 046 + 018 | 88 | 96 | 96 | 160 | 110 | 165 |
| 9212 + 9217 | 025 + 012 | 80 | 121 | 111 | 129 | 110 | 166 |
| 9044 + 9173 | 011 + 028 | 72 | 150 | 95 | 126 | 111 | 167 |
| 9007 + 9154 | 046 + 009 | 100 | 135 | 83 | 126 | 111 | 168 |
| 9154 + 9340 | 009 + 072 | 113 | 117 | 85 | 131 | 111 | 169 |
| 9338 + 9340 | 004 + 072 | 103 | 106 | 103 | 134 | 112 | 170 |
| 9096 + 9217 | 018 + 012 | 106 | 108 | 96 | 137 | 112 | 171 |
| 9007 + 9184 | 046 + 009 | 85 | 137 | 95 | 131 | 112 | 172 |
| 9007 + 9340 | 046 + 072 | 109 | 112 | 95 | 133 | 112 | 173 |
| 9044 + 9340 | 011 + 072 | 92 | 120 | 100 | 138 | 113 | 174 |
| 9184 + 9340 | 009 + 072 | 109 | 132 | 99 | 110 | 113 | 175 |
| 9122 + 9133 | 031 + 028 | 92 | 133 | 105 | 124 | 113 | 176 |
| 8955 + 9044 | 029 + 011 | 102 | 100 | 102 | 151 | 114 | 177 |
| 8906 + 9044 | 056 + 011 | 96 | 122 | 86 | 151 | 114 | 178 |
| 9007 + 9122 | 046 + 031 | 108 | 135 | 85 | 127 | 114 | 179 |
| 8820 + 9146 | 044 + 036 | 101 | 153 | 84 | 119 | 114 | 180 |
| 8908 + 9122 | 032 + 031 | 131 | 132 | 76 | 117 | 114 | 181 |
| 8906 + 9133 | 056 + 028 | 92 | 155 | 92 | 118 | 114 | 182 |
| 8908 + 9133 | 032 + 028 | 95 | 158 | 96 | 110 | 115 | 183 |
| 8908 + 9096 | 032 + 018 | 85 | 117 | 88 | 169 | 115 | 184 |
| 9217 + 9340 | 012 + 072 | 106 | 137 | 87 | 129 | 115 | 185 |
| 9133 + 9217 | 028 + 012 | 99 | 135 | 98 | 127 | 115 | 186 |
| 8906 + 9173 | 056 + 028 | 72 | 185 | 79 | 122 | 115 | 187 |
| 9007 + 9146 | 046 + 036 | 108 | 146 | 79 | 127 | 115 | 188 |
| 8906 + 9184 | 056 + 009 | 105 | 147 | 81 | 128 | 115 | 189 |
| 9007 + 9111 | 046 + 009 | 108 | 138 | 86 | 129 | 115 | 190 |
| 8908 + 9173 | 032 + 028 | 85 | 170 | 90 | 118 | 116 | 191 |
| 8908 + 9044 | 032 + 011 | 87 | 135 | 81 | 159 | 116 | 192 |
| 9044 + 9146 | 011 + 036 | 119 | 129 | 93 | 122 | 116 | 193 |
| 8908 + 9212 | 032 + 025 | 120 | 125 | 95 | 123 | 116 | 194 |
| 9007 + 9212 | 046 + 025 | 115 | 127 | 93 | 128 | 116 | 195 |
| 9044 + 9212 | 011 + 025 | 133 | 117 | 96 | 118 | 116 | 196 |
| 8820 + 9007 | 044 + 046 | 96 | 152 | 84 | 134 | 117 | 197 |
| 9044 | 011 | 115 | 118 | 98 | 137 | 117 | 198 |
| 8906 + 9122 | 056 + 031 | 122 | 148 | 78 | 120 | 117 | 199 |
| 8908 + 9340 | 032 + 072 | 106 | 128 | 94 | 141 | 117 | 200 |
| 9184 + 9338 | 009 + 004 | 124 | 129 | 92 | 126 | 118 | 201 |
| 8906 + 9154 | 056 + 009 | 119 | 144 | 79 | 128 | 118 | 202 |
| 9007 + 9044 | 046 + 011 | 112 | 129 | 87 | 145 | 118 | 203 |
| 8906 + 9212 | 056 + 025 | 133 | 136 | 86 | 120 | 119 | 204 |
| 9146 + 9338 | 036 + 004 | 135 | 126 | 91 | 123 | 119 | 205 |
| 8908 + 9338 | 032 + 004 | 106 | 129 | 101 | 139 | 119 | 206 |

TABLE 3-continued

Anti-proliferative effect of monoclonal antibodies and antibody mixtures

| mAb or mAb mixture | Sequence Cluster(s) | Metabolic activty of cells treated with mAb or mAb mixture (% of untreated control) | | | | | |
|---|---|---|---|---|---|---|---|
| | | SNU5 | OE33 | MKN45 | EBC1 | Average | Rank |
| 9007 + 9338 | 046 + 004 | 96 | 136 | 101 | 144 | 119 | 207 |
| 9154 | 009 | 123 | 119 | 97 | 138 | 119 | 208 |
| 9122 + 9338 | 031 + 004 | 129 | 123 | 99 | 126 | 119 | 209 |
| 8820 + 8908 | 044 + 032 | 110 | 154 | 83 | 131 | 119 | 210 |
| 8820 | 044 | 111 | 157 | 88 | 121 | 119 | 211 |
| 9007 + 9133 | 046 + 028 | 92 | 166 | 101 | 119 | 120 | 212 |
| 9146 + 9217 | 036 + 012 | 123 | 128 | 104 | 126 | 120 | 213 |
| 9122 + 9154 | 031 + 009 | 112 | 151 | 88 | 129 | 120 | 214 |
| 8906 + 9096 | 056 + 018 | 93 | 127 | 86 | 176 | 120 | 215 |
| 8906 + 9146 | 056 + 036 | 102 | 176 | 83 | 121 | 121 | 216 |
| 9154 + 9212 | 009 + 025 | 135 | 111 | 110 | 128 | 121 | 217 |
| 8908 + 9146 | 032 + 036 | 126 | 150 | 90 | 121 | 122 | 218 |
| 8906 + 9340 | 056 + 072 | 106 | 157 | 95 | 129 | 122 | 219 |
| 9146 + 9154 | 036 + 009 | 116 | 130 | 111 | 132 | 122 | 220 |
| 9154 + 9338 | 009 + 004 | 137 | 128 | 88 | 139 | 123 | 221 |
| 8820 + 9340 | 044 + 072 | 113 | 143 | 96 | 140 | 123 | 222 |
| 9007 | 046 | 122 | 141 | 94 | 139 | 124 | 223 |
| 8906 + 8908 | 056 + 032 | 93 | 147 | 98 | 157 | 124 | 224 |
| 9122 + 9212 | 031 + 025 | 130 | 138 | 110 | 123 | 125 | 225 |
| 8908 | 032 | 135 | 134 | 96 | 140 | 126 | 226 |
| 8906 + 9338 | 056 + 004 | 119 | 166 | 93 | 129 | 127 | 227 |
| 9122 + 9146 | 031 + 036 | 146 | 128 | 109 | 128 | 128 | 228 |
| 8906 | 056 | 127 | 153 | 95 | 136 | 128 | 229 |
| 8906 + 9007 | 056 + 046 | 84 | 157 | 100 | 172 | 128 | 230 |
| 9044 + 9096 | 011 + 018 | 124 | 138 | 98 | 155 | 129 | 231 |
| 9122 | 031 | 142 | 134 | 106 | 136 | 130 | 232 |
| 9122 + 9340 | 031 + 072 | 146 | 150 | 98 | 125 | 130 | 233 |
| 8908 + 9007 | 032 + 046 | 109 | 152 | 101 | 169 | 133 | 234 |
| 8906 + 8955 | 056 + 029 | 136 | 167 | 99 | 150 | 138 | 235 |

Example 3: Humanization of the 9006 and 9338 Antibodies

This example describes humanization of the murine antibody framework regions of the 9006 and 9338 antibodies. Antibody humanization is performed to produce a molecule with minimal immunogenicity when applied to humans, while retaining the specificity and affinity of the parental non-human antibody.

Methods

Humanization of the 9006 and 9338 antibodies was performed using the "CDR grafting" approach. First, the original murine germline genes were identified by blasting the V gene sequences of 9006 (FIG. 26) and 9338 (FIG. 27) against mouse germline V and J gene databases. This indicated that the closest mouse germline genes were IGHV9-1*02/IGHJ4*01 and IGKV8-28*01/IGKJ2*01 for the variable heavy and variable light genes of 9006, respectively. Similarly, the closest mouse germline genes were IGHV1-4*01/IGHJ3*01 and IGKV4-79*01/IGKJ4*01 for the variable heavy and variable light genes of 9338, respectively. Second, the antibody VH and VL genes were aligned against the murine germlines to identify somatic mutations in the framework regions that may play a role in antibody function and/or structure. Such residues may be included in the final humanized antibody genes as so-called "back mutation" residues. The 9006 and 9338 variable antibody sequences were then blasted against human immunoglobulin databases to identify the closest human germlines whose framework regions will be used for the antibody humanization. For the antibody 9006, the retained human germlines were IGHV7-4-1*02/IGHJ6*01 and IGKV4-1*01/IGKJ2*01 for the variable heavy and variable light genes, respectively. For the antibody 9338, the retained human germlines were IGHV1-69*08/IGHJ1*01 and IGKV3-11*01/IGKJ2*01 for the variable heavy and variable light genes, respectively. Finally, for each antibody, the CDR regions from the chimeric antibodies were grafted onto the selected human framework and J gene segments. The CDR sequences were assigned in accordance with IMGT® definitions.

Results

Figure 28:
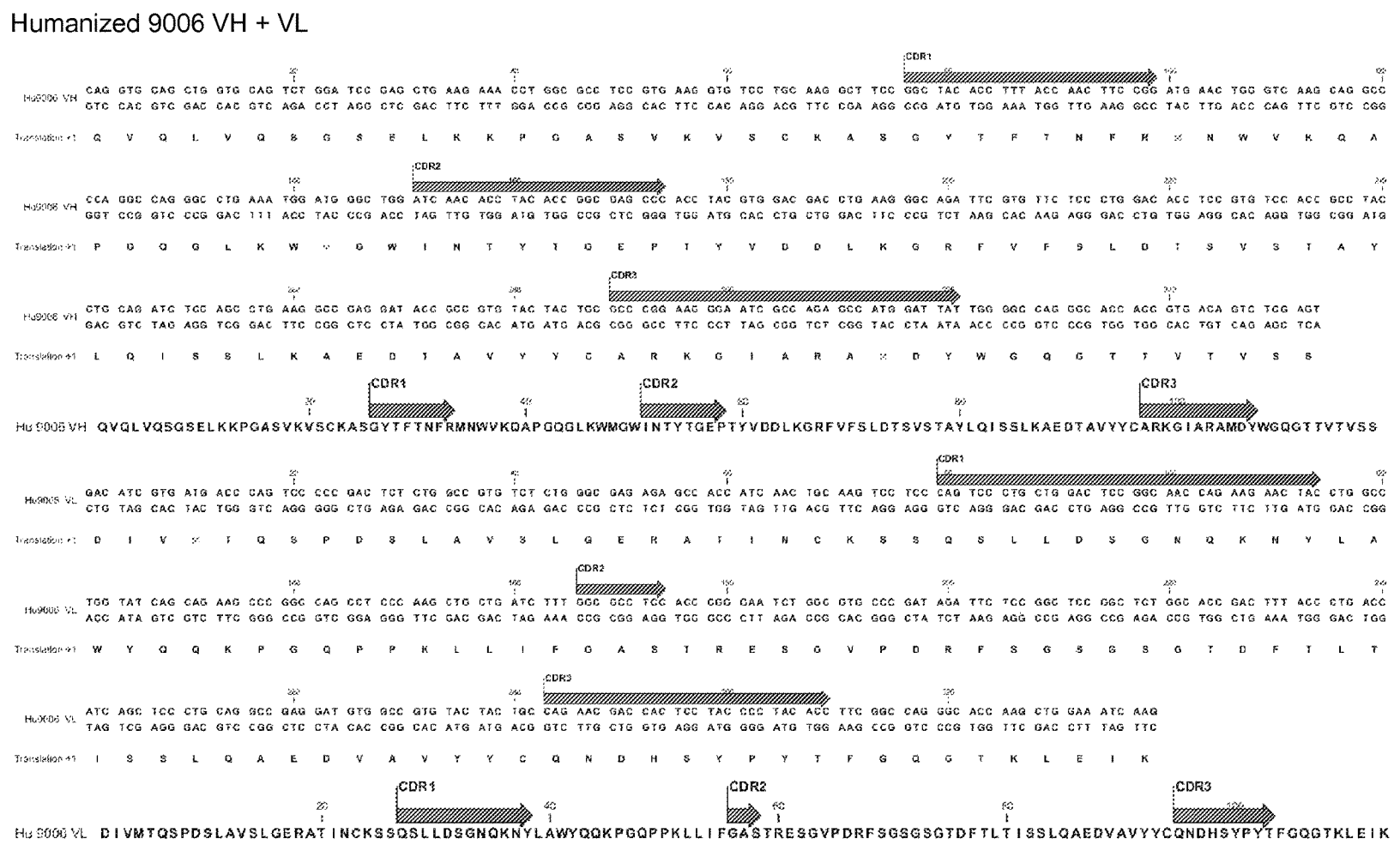
Figure 29:
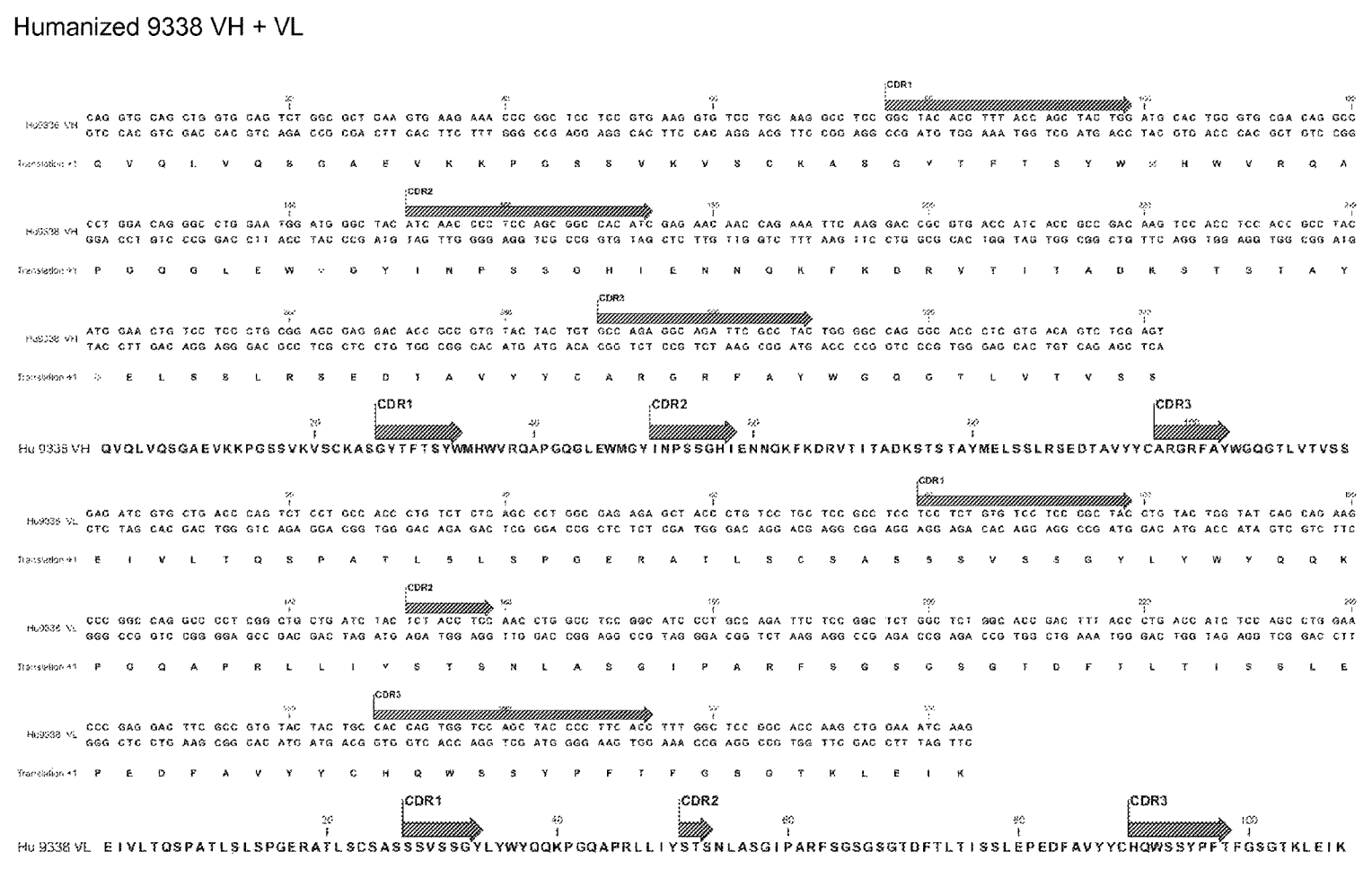

The final humanized 9006 and 9338 antibody sequences are shown in FIG. 28 and FIG. 29, respectively.

Example 4: Cloning of Anti-MET Reference Antibody Analogs

This example lists the sources of the amino acid sequences and the final antibody format used for generation of anti-MET reference antibody analogs. Some of the listed antibodies have been extensively characterized and have well-defined epitopes. A number of the antibodies have also entered clinical evaluation.

Methods

The amino acid sequences encoding the variable heavy and light chain domains of the antibody analogs in Table 4 were obtained from the listed patents or patent applications. The protein sequences were reverse translated to DNA sequences with human codon usage. The corresponding DNA sequences were gene synthesized and cloned into expression vectors containing constant human heavy or light chain domains, resulting in expression of full-length antibodies. One exception was for the 5D5 antibody that was expressed as a Fab fragment. The human antibody isotype selected for expression is listed in the antibody format column together with additional mutations introduced in the Fc region where applicable. CHO cells were transfected with the corresponding expression plasmids using a standard protein expression system, with the exception of hybridoma clone HB-12093, which was grown using standard hybridoma culturing technique. The corresponding antibody supernatants were purified using standard protein A purification column chromatography.

TABLE 4

Listing of gene-synthesized antibody analogs and the corresponding antibody format.

| Antibody clone | Research code | Antibody format | Reference |
|---|---|---|---|
| 224G11 | ABT-700, h224G11 | Recombinant IgG1 | EP2014681A1 |
| 223C4 | N.A. | Recombinant IgG1 | EP2014681A1 |
| C8-H241 | LY2875358, LA480, emibetuzumab | Recombinant IgG4 (S228P, F234A, L235A) | WO2010059654A1 |
| 36C4 | ARGX-111 | Recombinant IgG1 | US2012/0148607A1 |
| 5D5 | OA-5D5, MetMAb, onartuzumab | Recombinant IgG1 Fab | U.S. Pat. No. 7,476,724 B2 |
| 13-MET | N.A. | Recombinant IgG1 | WO2009/142738 A2 |
| 28-MET | N.A. | Recombinant IgG1 | WO2009/142738 A2 |
| HB-12093 | N.A. | Mouse Hybridoma | EP 0922102 |

Example 5: Epitope Binning of MET Antibodies

This example illustrates how the MET antibodies were grouped into epitope bins based on pairwise competition patterns. Antibodies belonging to different epitope bins recognize different epitopes on the MET extracellular domain (ECD).

Methods

Investigation of pairwise antibody competition was performed by Bio-layer Interferometry (BLI) analysis using an Octet QK384 instrument (Fortebio, USA). Commercially available human MET Fc fusion protein (R&D Systems) was captured on anti-human Fc sensor chips (Fortebio, USA) and residual anti-Fc sites blocked with Herceptin negative control antibody. The antigen coated surface was saturated with an anti-MET antibody concentration of 80 µg/ml followed by evaluation of pairwise anti-MET antibody combinations in competitive binding experiments. The sensor surface was regenerated by incubation with 10 mM glycine-HCl, pH 1.5 and reused for a new competition cycle.

Results

The competition pattern of the 13 tested MET antibodies is presented in FIG. 1. The MET antibodies were found to group in 12 distinct epitope bins. The antibody Hu9006 was found to bind a distinct epitope that overlapped with C8-H241. However the epitope was different compared to C8-H241, since C8-H241 was also blocked by Hu9338 and 36C4, while Hu9006 was not. Consequently, Hu9006 and C8-H241 were assigned to different epitope bins. The epitope of Hu9338 overlapped with 36C4 and both antibodies showed identical competition patterns with other antibodies in the tested panel, and these were consequently assigned to the same epitope bin.

Antibodies 224G11, 28-MET, 5D5, 9206 & 13-MET showed in some instances unidirectional inhibition. This observed phenomenon could be caused by allosteric effects and was observed in repeated competition experiments.

Example 6: Analysis of MET Antibodies for HGF Ligand Blocking Activity

This example illustrates how the panel of anti-MET antibodies was analyzed for HGF ligand blocking activity by performing a competition assay using Bio-Layer Interferometry analysis.

Methods

Investigation of HGF ligand blocking activity was performed by Bio-Layer Interferometry (BLI) analysis using an Octet QK384 instrument (Fortebio, USA). Commercially available human MET Fc fusion protein (R&D Systems) was captured on anti-human Fc sensor chips (Fortebio, USA) and residual anti-Fc sites blocked with Herceptin negative control antibody. Next the antigen coated surface was saturated with an anti-MET antibody concentration of 80 µg/ml (533 nM), except for 5D5 Fab fragment, which was diluted to 26.7 µg/ml (533 nM). After MET saturation with antibody HGF ligand blocking activity was assessed by incubation with human HGF ligand (R&D Systems) tested at 20 µg/ml (222 nM). Herceptin IgG1 was used as a negative control antibody.

Results

The result of the competition analysis is presented in Table 5 below. Antibody Hu9006 and Hu9338 were both found to inhibit HGF ligand binding by approx. 80%, while 5D5 Fab was found to fully block HGF binding (100%). When equimolar concentrations of Hu9006 and Hu9338 were mixed (80 µg/ml total concentration, 533 nM), HGF ligand binding was inhibited by approx. 90%. Consequently, more efficient HGF ligand blocking activity was obtained by mixing antibodies Hu9006 and Hu9338 1:1. The antibodies C8-H241 and 36C4 were found to inhibit HGF ligand binding by approx. 80 and 75%, respectively, while antibodies 13-MET and 28-MET blocked HGF binding by approx. 80 and 50%, respectively. The agonistic antibody 5882 and the negative control antibody Herceptin did not block HGF binding (3-7% HGF binding inhibition).

TABLE 5

HGF binding inhibition after MET antibody saturation.

| Antibody | % HGF binding inhibition |
|---|---|
| Hu9006 | 78 |
| Hu9338 | 81 |
| 5882 | 3 |
| Hu9006 + Hu9338 | 89 |
| C8-H241 | 81 |
| 36C4 | 74 |
| 224G11 | 20 |
| 223C4 | 69 |
| 13-MET | 81 |
| 28-MET | 50 |
| HB-12093 | 9 |
| 5D5 Fab | 100 |
| 12398 | 84 |
| 9206 | 62 |
| Herceptin | 6 |

Example 7: Epitope Mapping of Anti-MET Antibodies

This example illustrates how the binding epitopes of the MET antibodies of the invention were mapped to blade 2 or 3 in the SEMA-α domain, by analyzing binding to chimeric MET constructs expressed on cells. The example also illustrates how the epitopes of the antibodies of the invention are distinct compared to the tested reference antibody analogs.

Methods

The human MET receptor consists of an extracellular domain of 907 amino acids (residues 25-932). The extracellular domain can be subdivided into the SEMA domain (residues 27-515), a cysteine rich Plexin Semaphorin Integrin domain (PSI domain, residues 520-561) and four immunoglobulin like domains defined by the following amino acid sequences. IPT1: AA 563-655. IPT2: AA 657-739. IPT3: AA 742-836. IPT4: AA 837-932. The domain definitions are described in Gherardi et al., Proc Natl Acad Sci USA. 100(21):12039-44 (2003) and Uniprot entry P08581. The SEMA domain consists of seven beta sheets (blades) that fold into of a seven-bladed propeller structure (Stamos J. et al., EMBO J. 23:2325-2335. (2004)). A furin cleavage site is present at position 307-308, dividing the SEMA domain into α and β chains. The SEMA-α domain is encoded by amino acid residues 27-307 composing blades 1-4 and the SEMA-β domain is encoded by amino acid residues 308-515 composing blades 5-7. The SEMA-α domain contains a binding site for the β-chain of the HGF ligand while the MET binding site of the HGF α-chain remains elusive (Merchant et al., Proc Natl Acad Sci USA. 110(32):E2987-96 (2013)). A single report claims that the IPT3 and IPT4 domains of MET ECD also mediate high affinity HGF binding (Basilico et al., J Biol Chem. 283(30): 21267-21277 (2008)).

The mRNA sequence of human MET isoform 1 was downloaded from NCBI (ACCESSION NM_000245.2; the amino acid sequence is represented in SEQ ID NO: 1). Human MET also exists in a different isoform (isoform 2) where 19 amino acids (STWWKEPLNIVSFLFCFAS (SEQ ID NO: 2)) replace S755 in the IPT domain 3. The amino acid sequence of isoform 2 is listed as SEQ ID NO: 2. The full-length chicken and murine MET protein sequences including leader peptide sequences were downloaded from NCBI (ACCESSION NP_990543 (SEQ ID NO: 3) and NP_032617 (SEQ ID NO: 4) respectively). Chimeric human/chicken domain exchange variants of the extracellular domain (ECD), where each domain or subdomain was sequentially replaced with chicken DNA sequence, were gene synthesized together with fully human, murine or chicken MET ECD genes. Chimeric constructs where each of the seven blades in the SEMA domain were sequentially exchanged from human to mouse sequence were also synthesized.

The constructs used for determining the blade binding specificity were as follows (numbers refer to sequence exchanged to mouse sequence): Mouse blade 1: AA 25-83. Mouse blade 1-2: AA 25-162. Mouse blade 1-3: AA 25-233. Mouse blade 1-4: AA 25-295. Mouse blade 1-5: AA 25-430. Mouse blade 1-6: AA 25-479. Mouse blade 1-7: AA 25-513. The reverse constructs were also made. Mouse PSI-IPT4: (AA 515-932). Mouse blade 7-IPT4: (AA 480-932). Mouse blade 6-IPT4: (AA 431-932). Mouse blade 5b-IPT4: (AA 382-932). Mouse blade 5a-IPT4: (AA 293-932). Mouse blade 4-IPT4: (AA 234-932). Mouse blade 3-IPT4: (AA 163-932). Mouse blade 2-IPT4: (AA 84-932). Blades 1-4 are located in the SEMA-α subdomain and blades 5-7 in the SEMA-β subdomain.

Recently other chimeric constructs where llama sequences were exchanged with human sequences in the MET SEMA domain have been described (Basilico C. et al. J. Clin Invest. 124:3172-3186 (2014)). These constructs were synthesized as well, but with the modification that the mouse sequence was inserted instead of the llama sequence, since the llama MET sequence was not publicly available. The sequence definitions for the additional chimeric proteins were as follows (AA numbers refer to sequence exchanged to mouse sequence): LS1: AA25-122, LS2: AA25-224, LS3: AA25-312, LS4: AA25-371, LS5: AA25-473. LS1-3 reside in the SEMA-α subdomain and LS4-6 in the SEMA-β subdomain. Finally, constructs where 15 AA of the human MET ECD sequence in the SEMA-α subdomain were sequentially exchanged to mouse sequence were synthesized for more detailed mapping of linear epitopes. For construct 109-120 only 11 amino acids were exchanged to mouse sequence. Each construct was designed to overlap with 2 amino acids, and in total 22 constructs with up to 15 AA substitutions were made covering the human MET SEMA-α subdomain sequence after blade 1 (AA 89-313).

All the synthesized chimeric or wild type constructs described above were subcloned into expression vectors containing a SV5 peptide tag, a glycine serine linker and the coding sequence for a glycosylphospha-tidylinositol (GPI) anchor resulting in C-terminal fusion of this cassette to the gene of interest (Bouquin T. et al., J. Biotechnol. 125:516-528 (2006). The generated expression constructs were used for transient FreeStyle™ transfection of HEK293 cells and the produced fusion proteins were targeted to the cell membrane via the GPI anchor. MET antibodies were analyzed for binding to transfected cells by flow cytometry using an iQue® Screener (IntelliCyt corporation). Antibodies were tested in an 8-point titration experiment using 3 fold dilutions beginning from 50 µg/ml and detection with an anti-human IgG (H+L) Alexa Fluor® 647 dye. The expression levels of the MET constructs were monitored by biotinylated anti-SV5 mAb MCA1360B and detection with Streptavidin APC Cy7. Cut-off values defined as the average fluorescence signal of all antibodies tested at 50 µg/ml to the negative control chicken or mouse MET construct+four standard deviations were employed to discriminate background binding from specific binding for the domain exchange or blade exchange constructs. Antibody binding to constructs where single amino acids or 15 amino acids were exchanged to mouse sequence were normalized to 5D5 binding tested at 3 µg/ml, since the mutations were located in the SEMA-α subdomain and shown not to influence the binding of 5D5 directed against the SEMA-β subdomain.

Results

Figure 2:
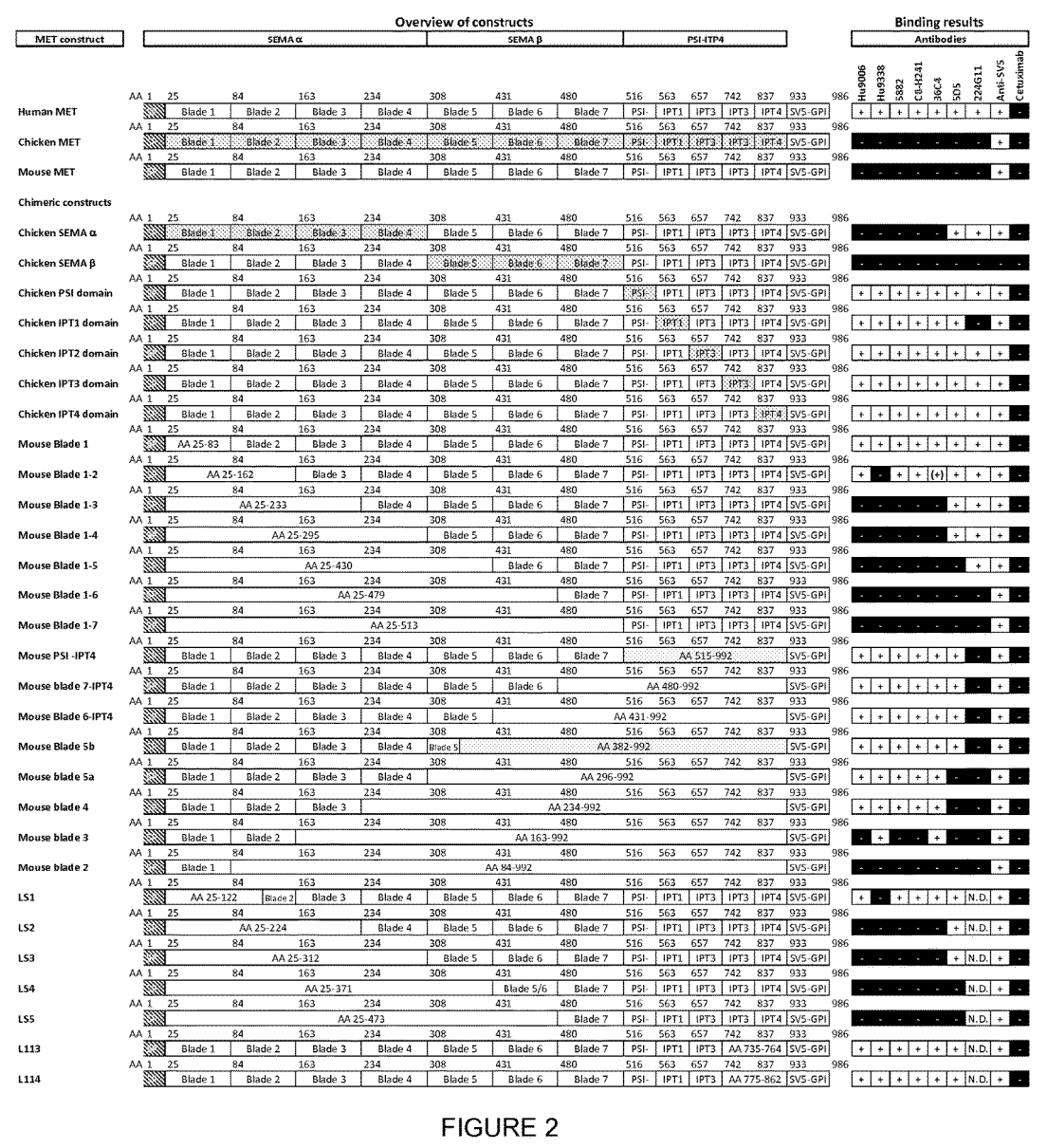

The surface expression level of the wild type and chimeric human, chicken or mouse MET ECD constructs were evaluated with SV5 staining. All evaluated constructs expressed well and could be stained with the SV5 antibody, except the construct containing chicken SEMA-β subdomain. The titers of each MET antibody binding to the constructs were evaluated (data not shown). A summary of the antibody binding to the different tested chimeric constructs is presented in FIG. 2. A summary of the differential antibody binding to human MET ECD constructs where 15 AA segments in SEMA-α subdomain were sequentially exchanged to mouse is presented in Table 6, and a summary of differential antibody binding to human MET ECD constructs where surface exposed residues in SEMA-α subdomain were mutated to mouse sequence is presented in Table 7. Finally, a summary of all the epitope findings is shown in Table 8.

All tested antibodies except 5D5 and 224G11 were found to bind the SEMA-α subdomain.

Fine epitope mapping using the chimeric constructs introducing mutations in the SEMA-α domain illustrated that Hu9338 bound to a linear epitope located in blade 2 as illustrated by a significant loss of binding (36% binding compared to 5D5), when the sequence segment AA 99-113 was exchanged to mouse (Table 6). The epitope for Hu9338 was distinct and not found for the other antibodies in the tested MET panel. Hu9006 was found to bind to an epitope present in a fragment of blade 3 (AA 163-224). None of single amino acid point mutated MET constructs or MET constructs with 15 AA inserted mouse MET sequence showed significantly different binding of hu9006 compared to fully human MET ECD. Consequently, the epitope of hu9006 was distinct compared to the other members of the anti-MET antibody panel. The finding that Hu9338 and Hu9006 bound to epitopes located in blade 2 and 3 respectively was consistent with these antibodies being non-competitive and belonging to different epitope bins.

The agonistic antibody 5882 was also found to bind to blade 3 (AA 163-224), but with contact residues at positions F206, D208, H209 & P210 as revealed by at least 50% or less binding compared to 5D5, when exchanging these positions to mouse sequence. Importantly, these closely located mutations did not significantly affect the binding of the other antibodies in the panel, illustrating that the strong agonistic activity of 5882 is related to binding the region defined by these 4 substitutions.

The C8-H241 antibody was found to bind to epitopes located in both blade 2 and 3. While blade exchange constructs showed that this antibody bound an important epitope in blade 3 (AA 163-224), further epitope refinement could be obtained by the observed reduction of binding to constructs where 15 AA in blade 2 (AA 119-133) or 24 AA blade 3 (AA 209-233) were exchanged to mouse sequence (68-30% binding respectively compared to 5D5). Finally, a contact residue identified in blade 3 (K223) resulting in only 19% binding compared to 5D5 indicated that the core epitope of the C8-H241 antibody is located in blade 3. The results were in good agreement with previously published data (Liu L. et al., Clin. Cancer. Res. 20:6059-6070 (2014)) showing that the linear epitopes of C8-H241 as determined by HD Exchange Mass Spectroscopy were present at positions 123-128, 144-156, 192-195 and 220-227.

Finally, we were able to map the epitope of 36C4 in finer detail. While Basilico et al. (Basilico C. et al. J. Clin Invest. 124:3172-3186 (2014)) described the epitope of 36C4 to be present in blade 2 & 3 (AA 98-199), we showed that the specificity can be divided into a linear epitope at position 129-143 in blade 2 (58% binding compared to 5D5) and a contact residue at position H209 in blade 3 (43% binding compared to 5D5). The contact residue at position H209 was also shared with the agonistic 5882 antibody, but since 5882 also bound three other closely located contact residues the binding and thus agonistic properties were clearly different.

The crystal structure of 5D5 binding to the SEMA domain has previously been published (Merchant M. et al., Proc. Natl. Acad. Sci. USA. 110:E2987-E2996 (2013)), and the study showed that 5D5 recognized mainly blade 5 and 6 in the SEMA β sub domain. Key amino acid residues at positions Q328, R331, L337 and N338 were present in blade 5, and when mutated to mouse residues these significantly reduced binding affinity. This result is in agreement with our binding analysis that clearly showed that 5D5 recognized a crucial epitope in blade 5 (AA 313-371).

We also found that the antibody 224G11 recognized the ITP1 domain in agreement with the information provided by Basilico and colleagues (Basilico C. et al. J. Clin Invest. 124:3172-3186 (2014)).

TABLE 6

Antibody binding to human MET ECD constructs expressed on HEK293 cells, where 15 AA segments in the SEMA-α domain were sequentially exchanged to mouse.

| Construct | Hu9338 | Hu9006 | C8-H241 | 36C4 | 5D5 | Cetuximab |
|---|---|---|---|---|---|---|
| MET 99-113 | 36 | 112 | 113 | 94 | 100 | 2 |
| MET 119-133 | 131 | 88 | 68 | 107 | 100 | 2 |
| MET 129-143 | 124 | 97 | 77 | 58 | 100 | 2 |
| MET 209-223 | 133 | 114 | 57 | 96 | 100 | 2 |
| MET 219-233 | 130 | 141 | 30 | 109 | 100 | 2 |
| human MET | 144 | 137 | 135 | 162 | 100 | 1 |

Antibody binding is expressed as the percentage of 5D5 binding. Bold numbers indicate less than 70% antibody binding compared to 5D5.

TABLE 7

Antibody binding to human MET ECD constructs expressed on HEK293 cells, where surface exposed residues in the SEMA-a domain were exchanged to mouse.

| Construct | Hu9338 | Hu9006 | 5882 | C8-H241 | 36C4 | 5D5 |
|---|---|---|---|---|---|---|
| F206P | 127 | 96 | 31 | 103 | 104 | 100 |
| D208G | 75 | 69 | 39 | 95 | 71 | 100 |
| H209Y | 94 | 90 | 49 | 84 | 43 | 100 |
| P210S | 100 | 79 | 18 | 105 | 89 | 100 |
| K223Q | 198 | 112 | 96 | 19 | 127 | 100 |
| human MET | 149 | 134 | 96 | 77 | 115 | 100 |

Antibody binding is expressed as the percentage of 5D5 binding. Bold numbers indicate less than 50% antibody binding compared to 5D5.

TABLE 8

Summary of the binding epitopes identified for tested MET antibodies using cell surface expressed mutated MET constructs.

| Antibody | SEMA Domain | Chimeric Blade | Fragment Residues (AA) | Linear epitope | Contact Residues | Epitope Bin | HGF blocking |
|---|---|---|---|---|---|---|---|
| Hu9338 | SEMA-â | 2 | AA 84-122 | BL 2 AA 99-113 | N.D. | Bin 8 | Yes |
| C8-H241 | SEMA-â | 2-3 | AA 163-224 | BL 2 AA 119-133 BL 3 AA 209-233 | BL 3 K223 | Bin 7 | Yes |
| 36C4 | SEMA-â | 2-3 | AA 84-224 | BL 2: 129-143 | BL 3 H209 | Bin 8 | Yes |
| Hu9006 | SEMA-â | 3 | AA 163-224 | N.D. | N.D. | Bin 6 | Yes |
| 5882 | SEMA-â | 3 | AA 163-224 | N.D. | BL 3 F206, D208, H209, P210 | Bin 9 | No |
| 5D5 | SEMA-â | 5 | AA 313-371 | N.D. | N.D. | Bin 4 | Yes |
| 224G11 | IPT1 | N.A. | AA 562-652 | N.D. | N.D. | Bin 1 | Yes |

Abbreviations:
AA: Amino Acid sequence.
N.A: Not applicable.
N.D: Not determined.
BL: Blade.

Example 8: Affinity Measurements for Chimeric and Humanized Anti-MET Antibodies This example demonstrates that the humanized variants of anti-MET antibodies 9006 and 9338 have affinities comparable to their chimeric counterparts, indicating that the humanized antibodies have the full functional activity of the chimeric antibodies. Furthermore, the humanized anti-MET antibodies show comparable binding to both human and cynomolgus MET ECD.

Methods

Kinetic binding analysis of the purified humanized and chimeric 9006 and 9338 variants was performed on an Octet QK384 Bio-Layer Interferometry (BLI) biosensor (Fortebio, USA) or an XPR-36 surface plasmon resonance (SPR) biosensor (Bio-Rad, USA).

His tagged human or cynomolgus MET ECD antigens were purchased from Sinobiological, China. Binding kinetics were measured under monovalent antigen conditions by immobilizing anti-MET antibodies and keeping the monovalent MET antigen in solution as described previously (Canziani et al., Anal Biochem 325(2):301-307 (2004). The lowest possible anti-MET antibody density was applied to prevent non-specific binding and mass transport limitation. For measuring antibody kinetics on the Octet system, antibodies at a concentration of 1.5 µg/ml were captured on anti-human Fc sensors (Fortebio, USA), and tested for binding to human MET ECD antigen (100 nM) serially diluted two-fold seven times. Measurements were conducted with a plate rotation speed of 1000 rpm and sensors were regenerated and reused by brief 5 second alternations between exposure to 10 mM Glycine:HCl buffer (pH 1.5) or PBS buffer containing 1% BSA and 0.001% Tween 20 three times. For the Surface Plasmon Resonance experiments conducted on the Bio-Rad XPR-36 instrument, anti-MET antibodies were adjusted to a concentration of 0.25-0.5 µg/ml and captured on anti-human IgG Fc surfaces generated by immobilizing a monoclonal anti-human Fc antibody (Biacore, Denmark). Anti-MET antibodies were tested for binding to human or cynomolgus MET ECD in a 2-fold concentration range from 25 nM to 1.56 nM followed by regeneration of the surfaces with 3 M $MgCl_2$ regeneration buffer (Biacore, Denmark). The recorded binding responses were fitted to a simple Langmuir 1:1 binding model for calculation of the on-rate (kon or ka), off-rate (koff or kd) and affinity (KD) constants using double referencing.

Results

The kinetic measurements using the Octet biosensor showed that the humanized variant of 9006 with 3 back mutations (Hu9006) and the humanized variant of 9338 (Hu9338) with no back mutations have slightly improved affinity for the human MET antigen compared to the chimeric parent antibodies (Table 9).

TABLE 9

Binding kinetics of chimeric and humanized MET antibodies to human MET ECD as measured by Bio-Layer Interferometry (BLI).

| Antibody | MET ECD | kon (M−1 s−1) | | kon Error | koff (s−1) | | koff Error | KD (M) |
|---|---|---|---|---|---|---|---|---|
| 9006 | human | 5.4E+04 | ± | 4.4E+02 | 1.2E−04 | ± | 2.2E−06 | 2.2E−09 |
| hu9006 | human | 6.2E+04 | ± | 6.8E+02 | 7.6E−05 | ± | 3.1E−06 | 1.2E−09 |
| 9338 | human | 1.9E+05 | ± | 2.7E+03 | 1.1E−04 | ± | 4.0E−06 | 6.0E−10 |
| hu9338 | human | 1.0E+05 | ± | 2.0E+03 | 2.7E−05 | ± | 3.6E−06 | 2.6E−10 |

The kinetic measurements using the Bio-Rad XPR36 SPR instrument showed that Hu9006 and Hu9338 recognize both human and cynomolgus MET ECD with affinities in the pM range (Table 10).

TABLE 10

Binding kinetics of humanized MET antibodies to human or cynomolgus MET ECD as measured by Surface Plasmon Resonance (SPR).

| Antibody | MET ECD | kon (M−1 s−1) | | kon Error | koff (s−1) | | koff Error | KD (M) |
|---|---|---|---|---|---|---|---|---|
| hu9006 | human | 1.9E+05 | ± | 1.2E+03 | 1.1E−05 | ± | 2.3E−07 | 5.5E−11 |
| hu9006 | cynomolgus | 1.8E+05 | ± | 1.5E+03 | 1.6E−05 | ± | 2.9E−07 | 8.6E−11 |
| hu9338 | human | 4.7E+05 | ± | 1.9E+02 | 6.3E−06 | ± | 3.7E−07 | 1.4E−11 |
| hu9338 | cynomolgus | 7.4E+05 | ± | 2.2E+03 | 5.4E−05 | ± | 3.6E−07 | 7.4E−11 |

Example 9: Degradation of MET with Anti-MET Antibodies

This example demonstrates that the anti-MET antibodies 9006 and 9338 induce degradation of MET, alone and in combination. The combination of the two antibodies induces more efficient degradation of the MET receptor than either antibody alone.

Methods

To investigate the level of MET receptor degradation induced by individual anti-MET antibodies 9006 and 9338, the mixture of 9006 and 9338, and the C8-H241 analogue (see Table 4), Western Blot or Simple Western analysis was performed on whole cell lysates of SNU5, EBC1 and MKN45 cells treated with antibody for 24 or 48 hours. In brief, cells were grown in T-75 culture flasks, and when 50% confluent the culture media were removed, the cells were washed and treated with a 20 μg/ml total antibody concentration of either C8-H241, 9006, 9338, 9338+9006, or a negative control antibody (human IgG1 against a non-mammalian target) for 24 or 48 hours in a humidified incubator at 37° C. Whole cell lysates were prepared using standard RIPA buffer. The total protein concentration was determined using a BCA assay and 1-10 μg protein analyzed by the Simple Western automated immunoassay on a Sally instrument (ProteinSimple) or by Western Blot analysis using primary detection antibodies against MET. An antibody against β-actin was used as loading control for the Western blot analysis.

Results

Figure 3:
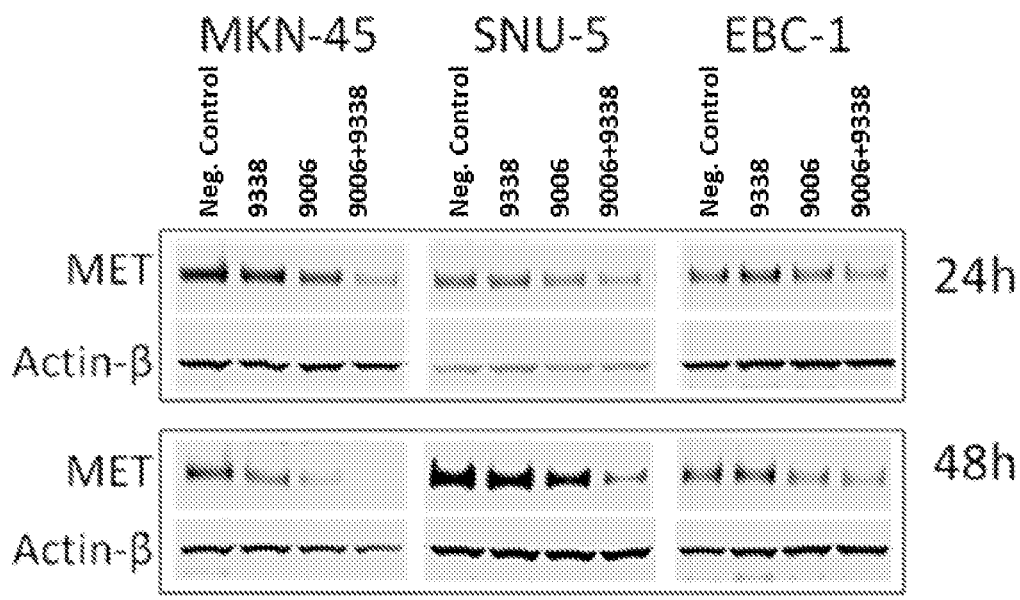
FIG. 3 shows the results of a Western blot analysis of MET receptor levels in cell lines treated with negative control antibody, 9006, 9338, or 9006+9338 for 24 or 48 hours.
Figure 4:
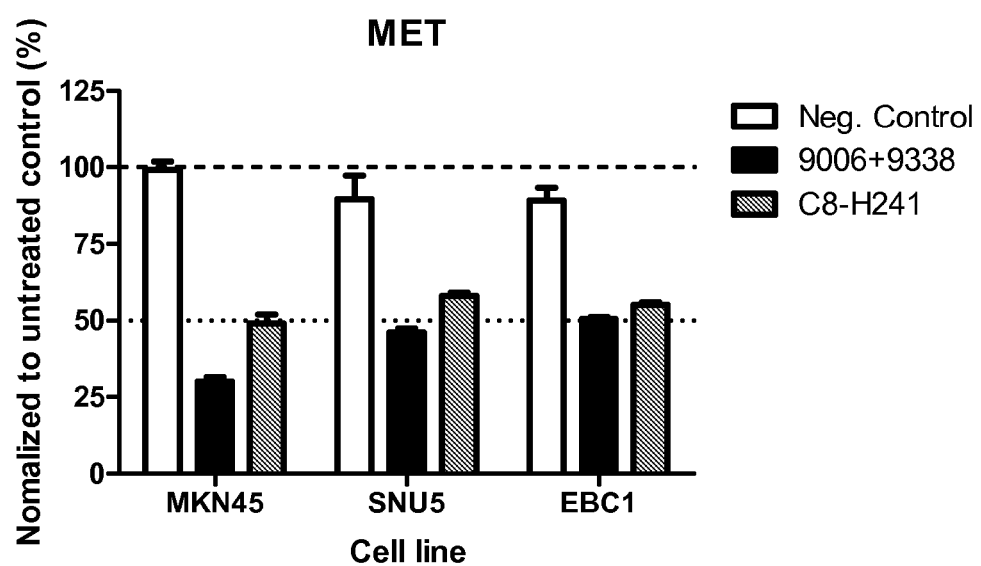
FIG. 4 shows the results of a Simple Western analysis of MET levels in cell lines treated with either negative control antibody, 9006+9338, or C8-H241 antibody for 24 hours.

The results from the Western Blot investigation (FIG. 3) show that treatment with the individual antibodies (especially 9006) induces some degradation of MET in all cell lines tested. However, the anti-MET antibody mixture 9338+9006 induces enhanced MET receptor degradation compared with the individual antibodies (9006 or 9338) across all cell lines tested. The cellular MET receptor level after 24 hours or treatment with 9006+9338 or C8-H241 was compared by Simple Western analysis in the three cell lines SNU5, EBC and MKN45. Results shown in FIG. 4 demonstrate enhanced MET degradation after treatment with 9006+9338 in all three cell lines.

Example 10: Inhibition of MET Phosphorylation and Downstream Signaling with Anti-MET Antibodies This example demonstrates that the anti-MET antibodies 9006 and 9338 have differential and cell line-dependent effects on MET phosphorylation and downstream signaling (as determined by levels of pERK2 and pAKT). The anti-MET antibody mixture 9006+9338 induces efficient inhibition of MET phosphorylation and downstream signaling.

Methods

To investigate the level of inhibition of MET phosphorylation and downstream signaling induced by anti-MET antibodies 9006 and 9338 and the anti-MET antibody mixture 9006+9338, Simple Western analysis was performed on whole cell lysates of MKN45 and EBC-1 cells treated with antibody for 24 hours. Cells were grown in 6-well plates. When 50% confluent, the culture media was removed, and the cells were washed in 1×PBS and treated with 20 μg/ml total antibody concentration (9006, 9338, 9006+9338, or the negative control antibody Synagis®) for 24 hours in a humidified incubator at 37° C. Whole cell lysates were prepared using standard RIPA buffer. The total protein concentration was determined using a BCA assay, and approximately 1 mg/ml protein analyzed by Simple Western analysis using a Sally instrument (automated size-based immunoassay system, ProteinSimple) and by using primary antibodies against phosphorylated MET (Tyr1234/1235 and Tyr1349), phosphorylated ERK2 (pERK2), and phosphorylated AKT (pAKT). An antibody against β-actin was used as loading control (data not shown).

Results

Figure 5:
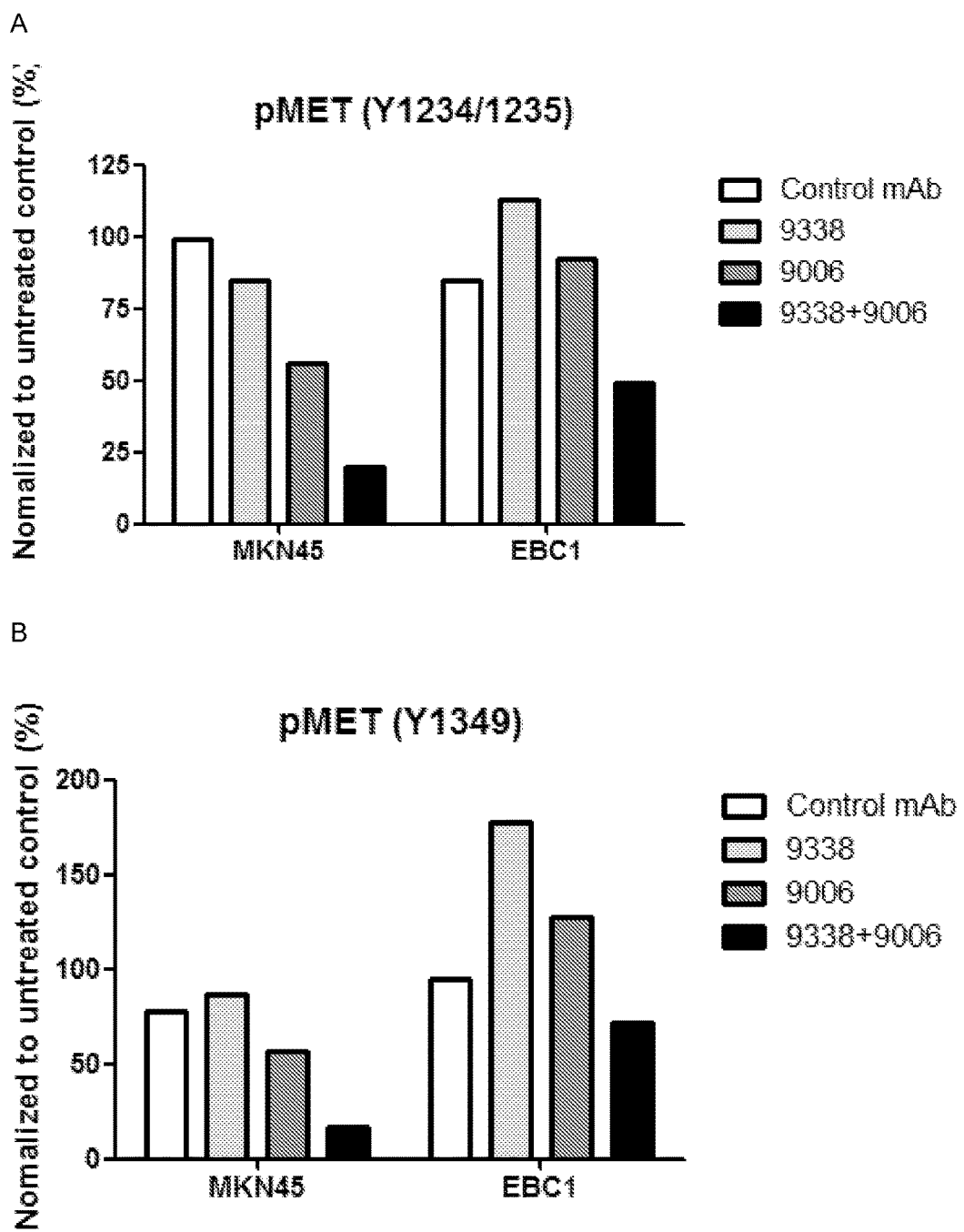
FIGS. 5A-5B show a Simple Western analysis of MET phosphorylation levels in cell lines treated with chimeric antibodies 9006 or 9338 or the antibody mixture 9006+9338
Figure 6:
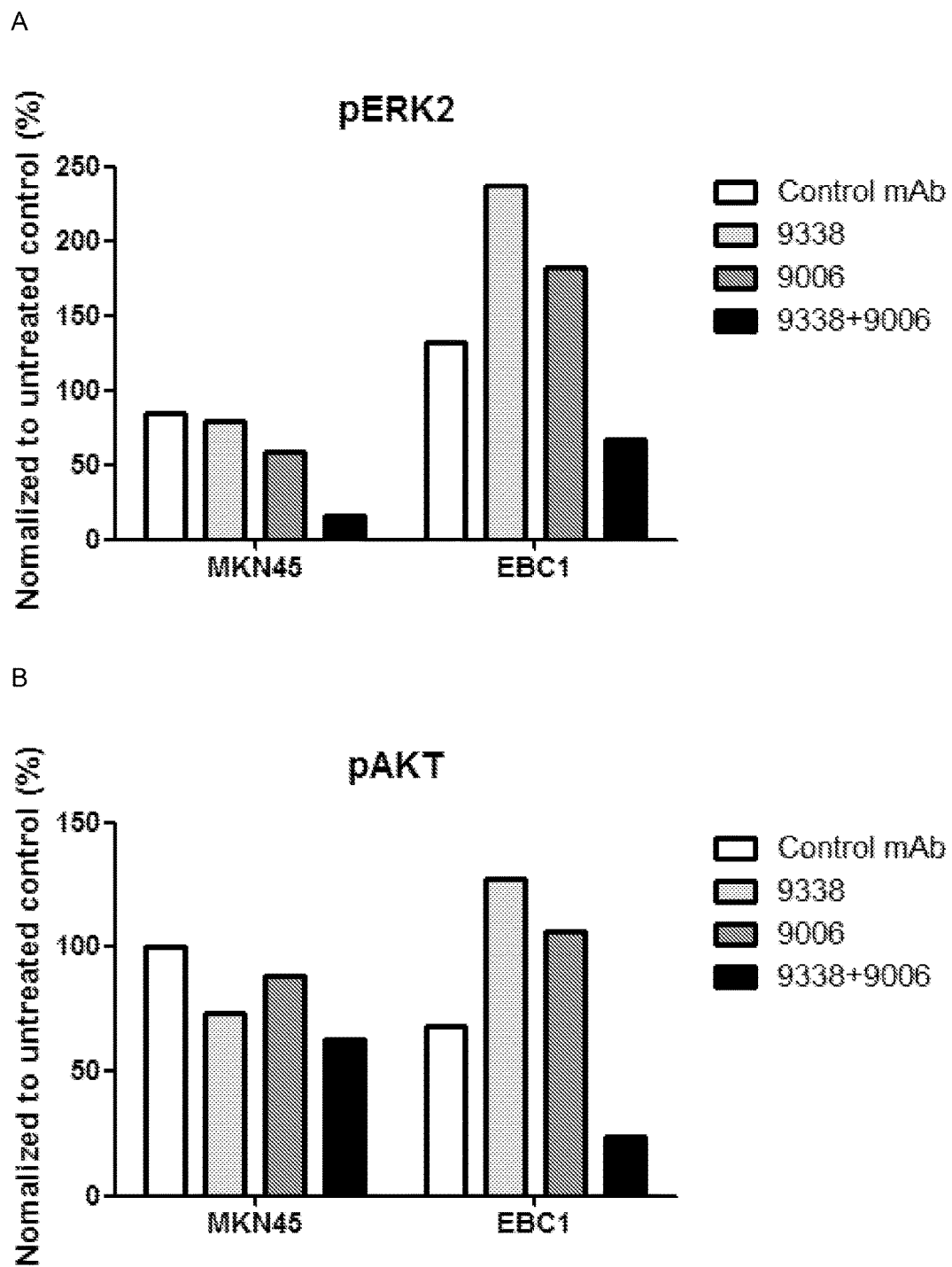
FIGS. 6A-6B show a Simple Western analysis of ERK2 and AKT phosphorylation levels in cell lines treated with chimeric antibodies 9006 or 9338 or the antibody mixture 9006+9338.
Figure 7:
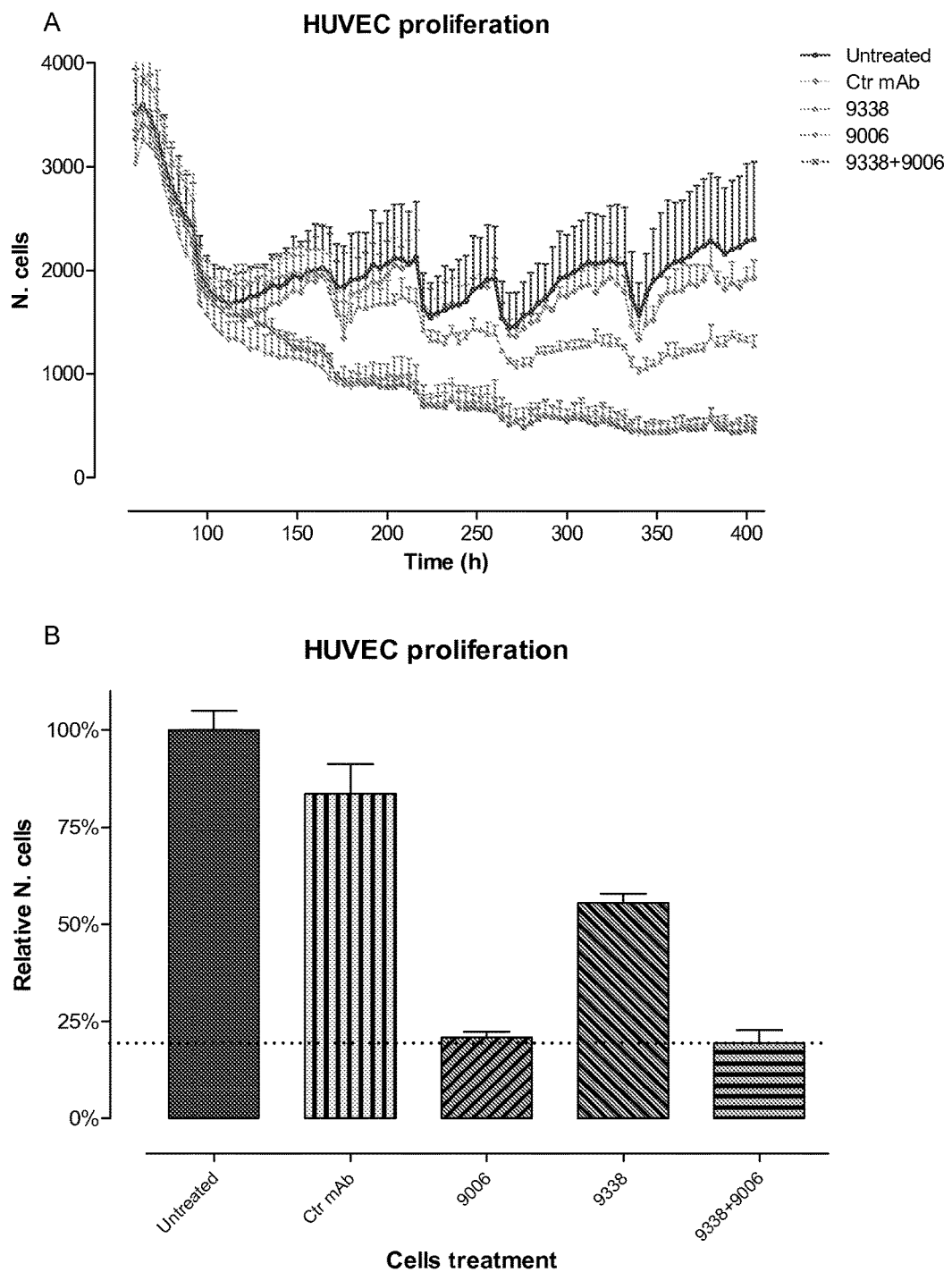
FIG. 7A shows the number of HUVECs after treatment with chimeric antibody 9006 or 9338, the antibody mixture 9006+9338, or a control antibody. 25 µg/ml of total antibody is used (both singly and in the antibody mixture).
FIG. 7B depicts the results of the assay at the final timepoint, 404 hours of incubation. The data are normalized to untreated cells (100%).
Figure 8:
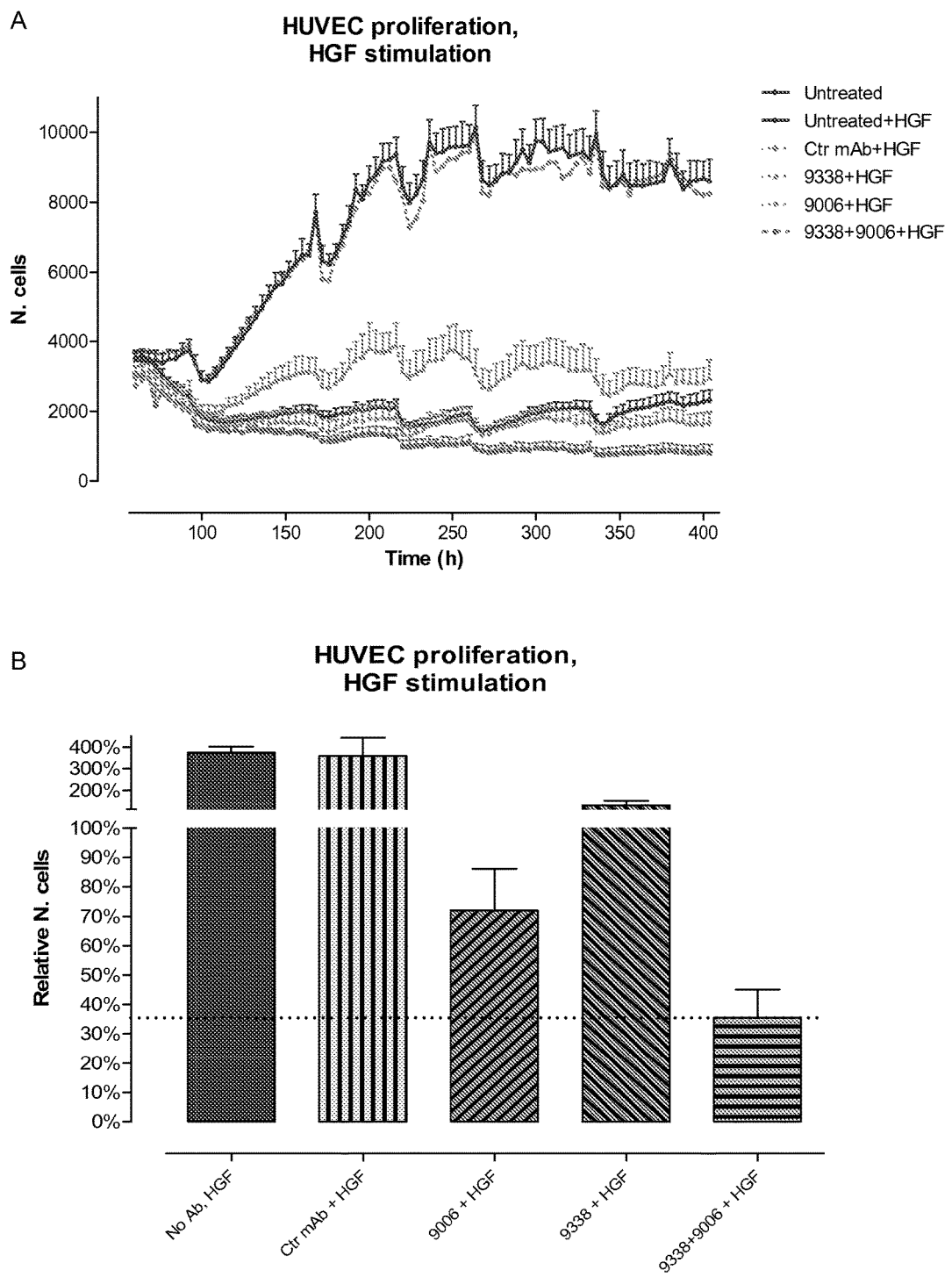
FIG. 8A shows the number of HUVECs after treatment with chimeric antibody 9006 or 9338, the antibody mixture 9006+9338, or a control antibody, in presence of HGF at 20 ng/ml. 25 µg/ml of total antibody is used (both singly and in the antibody mixture).
FIG. 8B depicts the results of the assay at the final timepoint, 404 hours of incubation/HGF stimulation. The data are normalized to untreated cells (100%).
Figure 9:
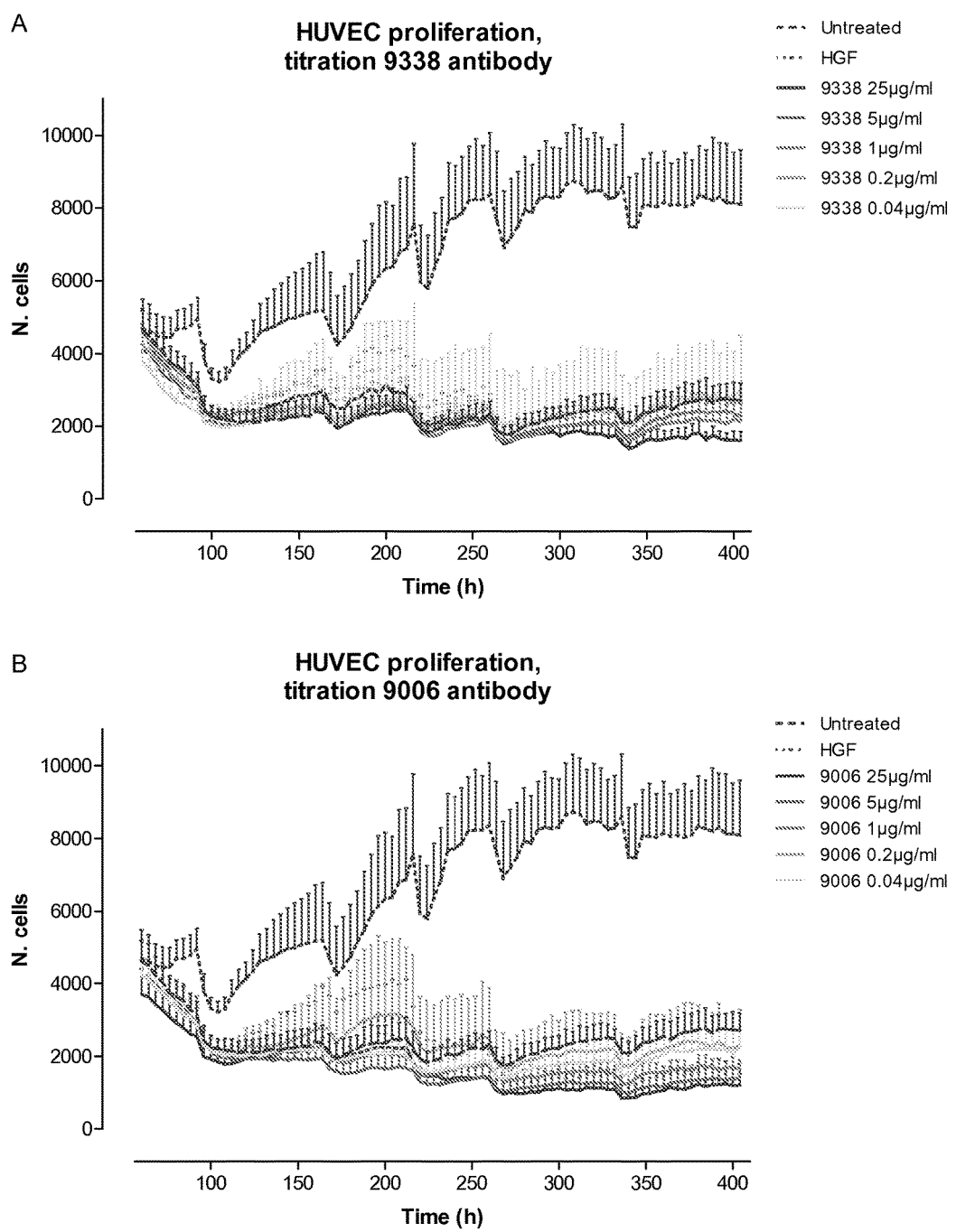
FIGS. 9A-9B show titration curves of the number of HUVECs after treatment with varying amounts of chimeric antibodies 9338 and 9006 (A and B, respectively).
Figure 10:
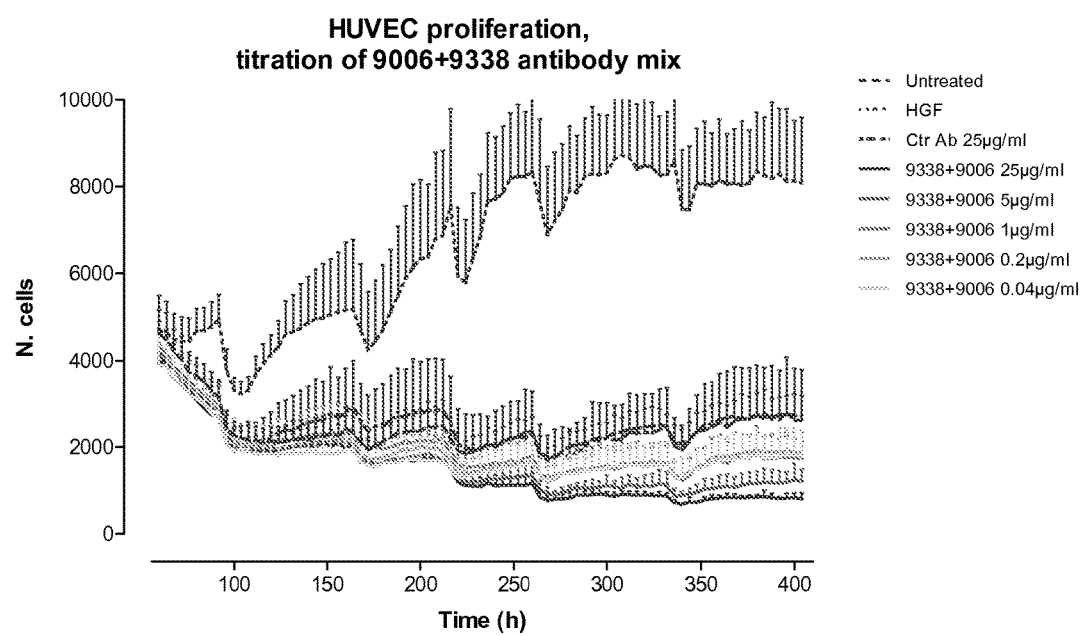
FIG. 10 shows titration curves of the number of HUVECs after treatment with varying amounts of the antibody mixture 9006+9338.
Figure 11:
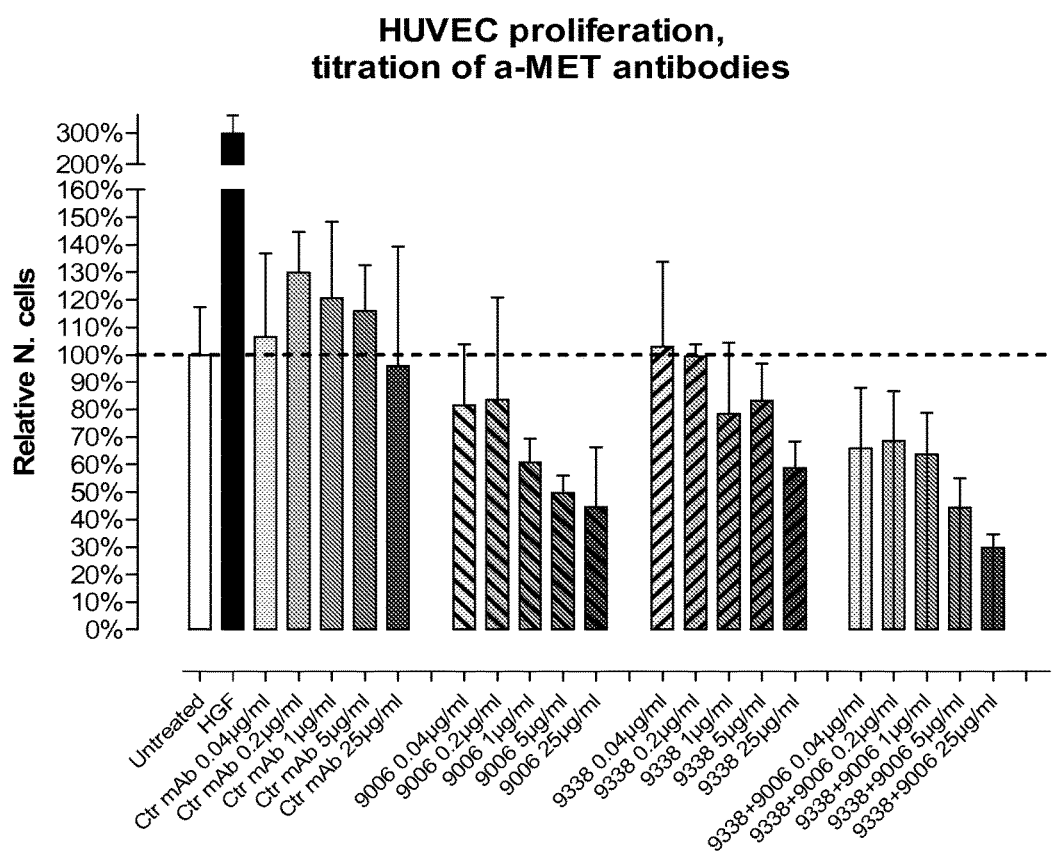
FIG. 11 depicts the results at the final time point from FIGS. 9 and 10. The data are normalized to untreated cells.

The results from the Simple Western analysis of phosphorylation levels of MET (FIG. 5) and ERK2 and AKT (FIG. 6) show that treatment with 9006 or 9338 alone induces differential and cell line-dependent effects on phosphorylation in the cell lines tested. The anti-MET antibody mixture 9006+9338, however, induces efficient inhibition of MET phosphorylation and downstream signaling compared to treatment with monoclonal anti-MET antibody 9006 or 9338 in both MKN45 and EBC-1 cells.

Example 11: Anti-Proliferative Effect of Chimeric Anti-MET Antibodies in Primary Endothelial Cells Human umbilical vein endothelial cells (HUVEC) are primary endothelial cells suitable for evaluating biological effects in a sensitive vascular model. The anti-MET antibodies 9006 and 9338 and the antibody mixture 9006+9338 are shown to be able to inhibit the growth of HUVECs, both in the absence and presence of the MET ligand HGF.

Materials and Methods

Dermal fibroblast cells were thawed and seeded in seeding medium in 96-well plates. After sedimentation of the fibroblasts at room temperature, a vial of GFP labeled-HUVECs was thawed. The HUVECs, resuspended in seeding medium, were added on top of the fibroblast suspension and incubated overnight in an Incucyte instrument (Essen Bioscience) at 37° C. and 5% $CO_2$. After overnight incubation, medium from the co-cultured cells was removed and replaced with growth medium for an additional 24 hours. The following day, assay medium was prepared, and different ligand/antibody mixtures were combined and mixed into the assay medium. The growth medium was removed and replaced with the assay medium containing the different combination of antibodies/ligands. The medium was exchanged with fresh assay medium containing antibody/ligand mixtures every two to three days. Pictures of GFP-HUVECs were recorded every four hours. Several cell parameters, including cell number, cell network length, and number of network branching points were analyzed using Incucyte software.

Results

FIGS. 7-11 show the efficacy of antibodies 9006 and 9338 antibodies in specifically inhibiting primary endothelial cell proliferation, in contrast to an unrelated antibody control that does not show any inhibitory effect. The antibody mixture 9006+9338 demonstrates superior inhibition of HUVEC proliferation, particularly when HGF is present in the medium.

Example 12: In Vitro Comparison of Chimeric and Humanized Anti-MET Antibodies

This example describes in vitro comparison of chimeric 9006, chimeric 9338 and chimeric 9338+9006 with the humanized variants i.e. humanized 9006 (Hu9006), humanized 9338 (Hu9338) and humanized 9338+9006 (Hu9338+Hu9006). The monoclonal antibodies and the mixture were evaluated for their ability to inhibit the growth of several cancer cell lines: Okajima, EBC1, MKN45, HCC827R1_cet#3, HCC827R1_cet#1 and KatoII.

Methods

Figure 12:
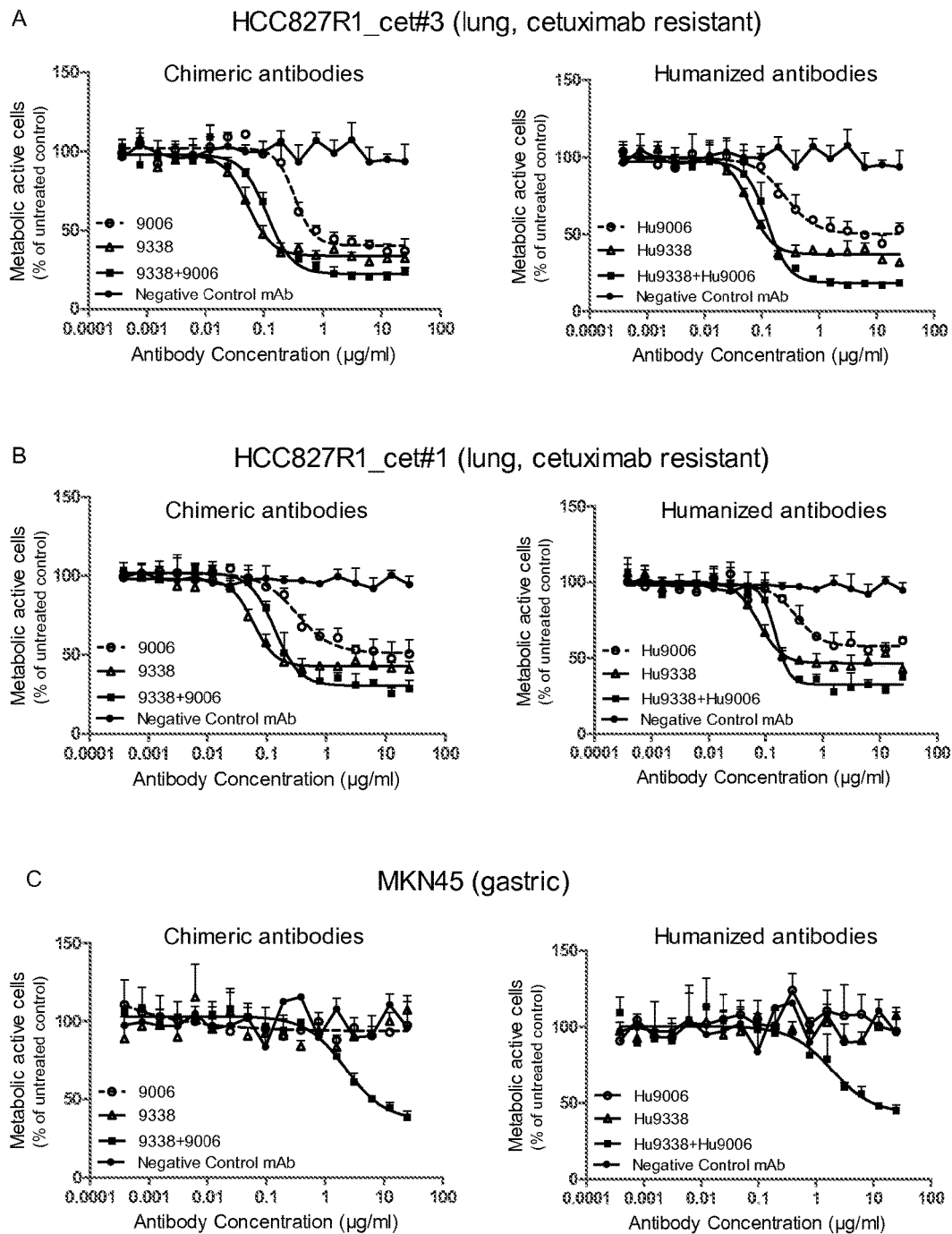
FIGS. 12A-12C show the results of a metabolic activity assay indicating the anti-proliferative effect of chimeric (left panel) or humanized (right panel) 9006, 9338, or 9006+9338 on the cell lines HCC827R1_cet#3 (12A), HCC827R1_cet#1 (12B) and MKN45 (12C).
Figure 13:
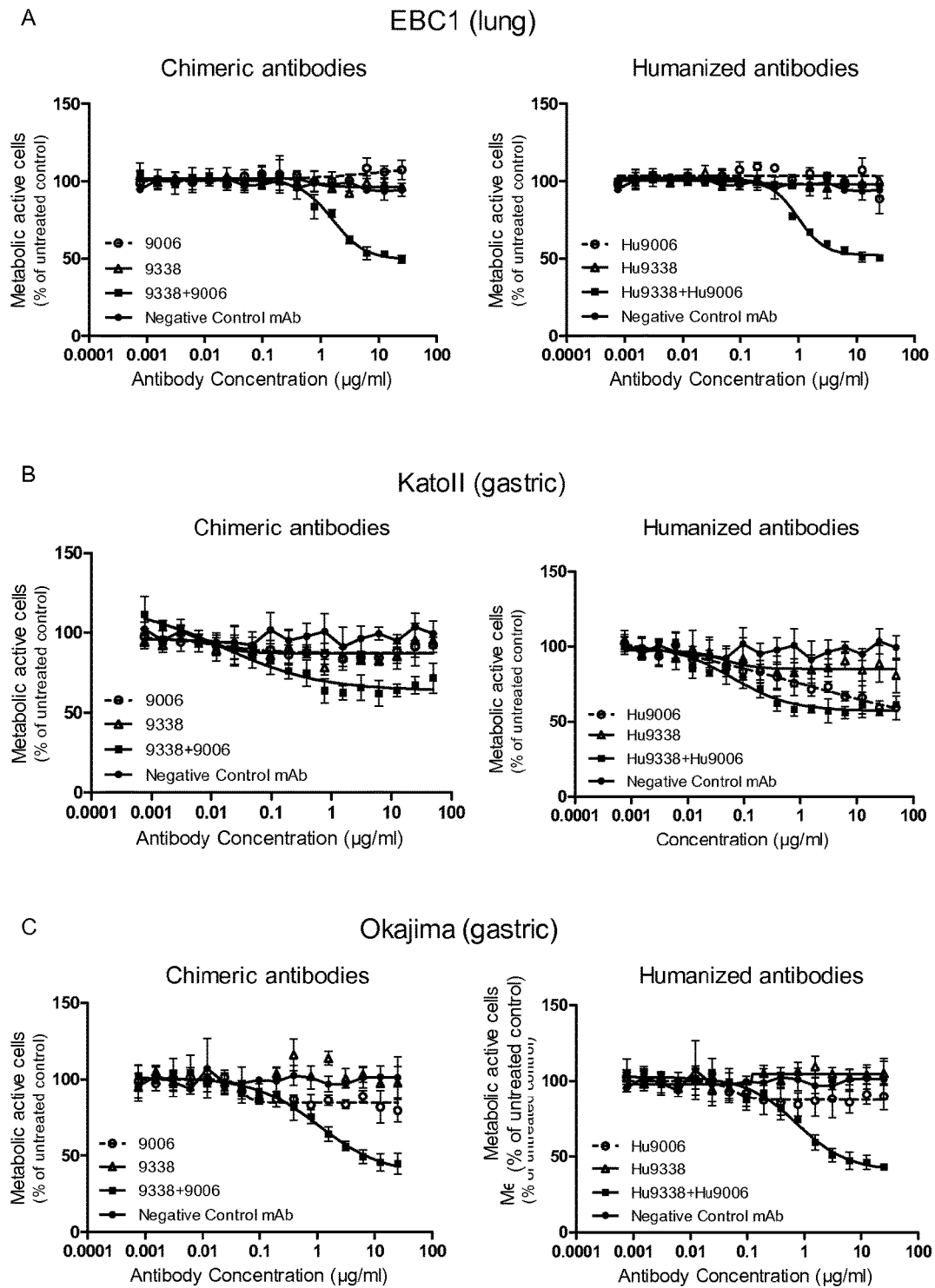
FIGS. 13A-13C show the results of a metabolic activity assay indicating the anti-proliferative effect of chimeric (left panel) or humanized (right panel) 9006, 9338, or 9006+9338 on the cell lines EBC-1 (13A), KatoII (13B), and Okajima (13C).

The 9006, 9338, 9338+9006 (1:1 mixture of the two components), Hu9006, Hu9338 and Hu9338+Hu9006 (1:1 mixture of the two components) along with the negative control antibody (Synagis®) were diluted to a final total antibody concentration of 100 μg/ml in RPMI 1640 Glutamax media supplemented with 2% FBS and 1% P/S, yielding a final concentration of 25 μg/ml in wells containing the highest antibody concentration. A twofold serial dilution of the antibodies was then performed, giving up to 17 different concentrations. Relevant numbers of cells (Okajima: 1000 cells/well, EBC1: 750 cells/well, MKN45: 500 cells/well, HCC827R1_cet#3: 500 cells/well, HCC827R1_cet#1: 500 cells/well; KatoII: 750 cells/well) were added to the experimental wells in a 384 well plate, and incubated with antibodies for 4 days in a humidified incubator at 37° C. WST-1 reagent was subsequently added to the plates and incubated for one hour at 37° C. The absorbance was measured at 450 nm and 620 nm (reference wavelength) using an ELISA reader. The absorbance at 620 nM were subtracted from the absorbance at 450 nM, and the amount of metabolically active cells (MAC) was calculated as a percentage of the untreated control as described in Example 2.
Results FIGS. 12 and 13 depict the viability results from titrations of chimeric and humanized 9006 and 9338 antibodies and the chimeric and humanized 9006+9338 antibody mixture on the cell lines HCC827R1_cet#3 (12A), HCC827R1_cet#1 (12B), MKN45 (12C), EBC-1 (13A), KatoII (13B), and Okajima (13C). It is evident from the graphs that Hu9006, Hu9338, and Hu9338+Hu9006 have an anti-proliferative effect comparable to that of their chimeric counterparts.

Example 13: In Vitro Comparison of Humanized 9338+9006 and 13-MET+28-MET

Figure 14:
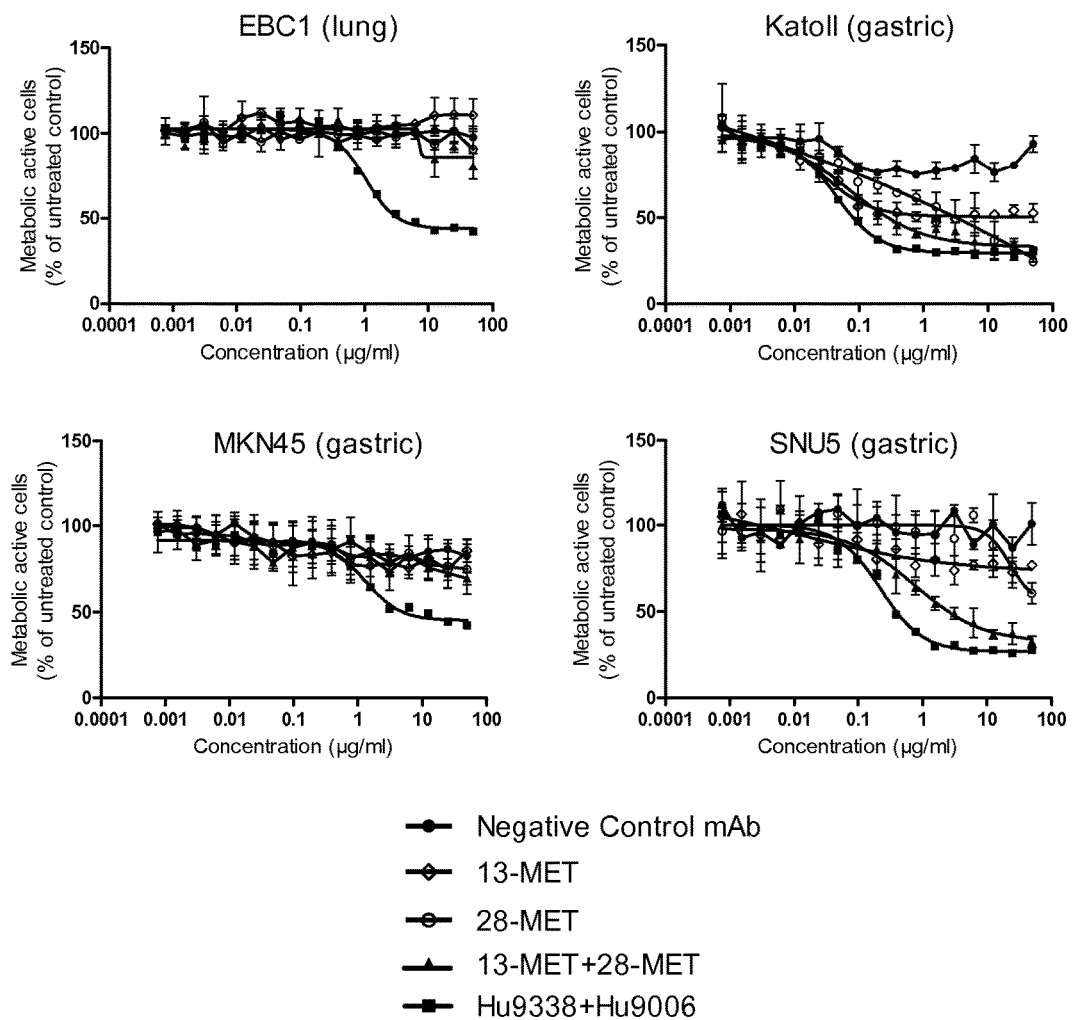
FIG. 14 shows viability results from titrations of Hu9338+ Hu9006, 13-MET, 28-MET and 13-MET+28-MET antibodies on the cell lines EBC1, MKN45, SNU5 and KatoII.

This example describes the in vitro testing of humanized 9338+9006 (Hu9338+Hu9006), 13-MET, 28-MET and 13-MET+28-MET (see Table 4). The monoclonal antibodies and the mixtures were evaluated for their ability to inhibit the growth of four cancer cell lines: EBC1, MKN45, SNU5 and KatoII.
Methods Antibodies Hu9338+Hu9006 (1:1 mixture of the two components), 13-MET, 28-MET and 13-MET+28-MET (1:1 mixture of the two components) along with the negative control antibody (Synagis®) were tested for anti-metabolic effect in EBC1 (500 cells/well), MKN45 (750 cells/well), SNU5 (750 cells/well) and KatoII (750 cells/well) as described above.
Results The viability results from titrations of Hu9338+Hu9006, 13-MET, 28-MET and 13-MET+28-MET antibodies on the cell lines EBC1, MKN45, SNU5 and KatoII are shown in FIG. 14. It is evident that the anti-MET antibodies have different levels of efficacy and potency depending on the cell line tested. However, the combination of Hu9338 and Hu9006 demonstrate superior inhibition of metabolic activity compared with 13-MET, 28-MET and 13-MET+28-MET across all cell lines tested.

Figure 15:
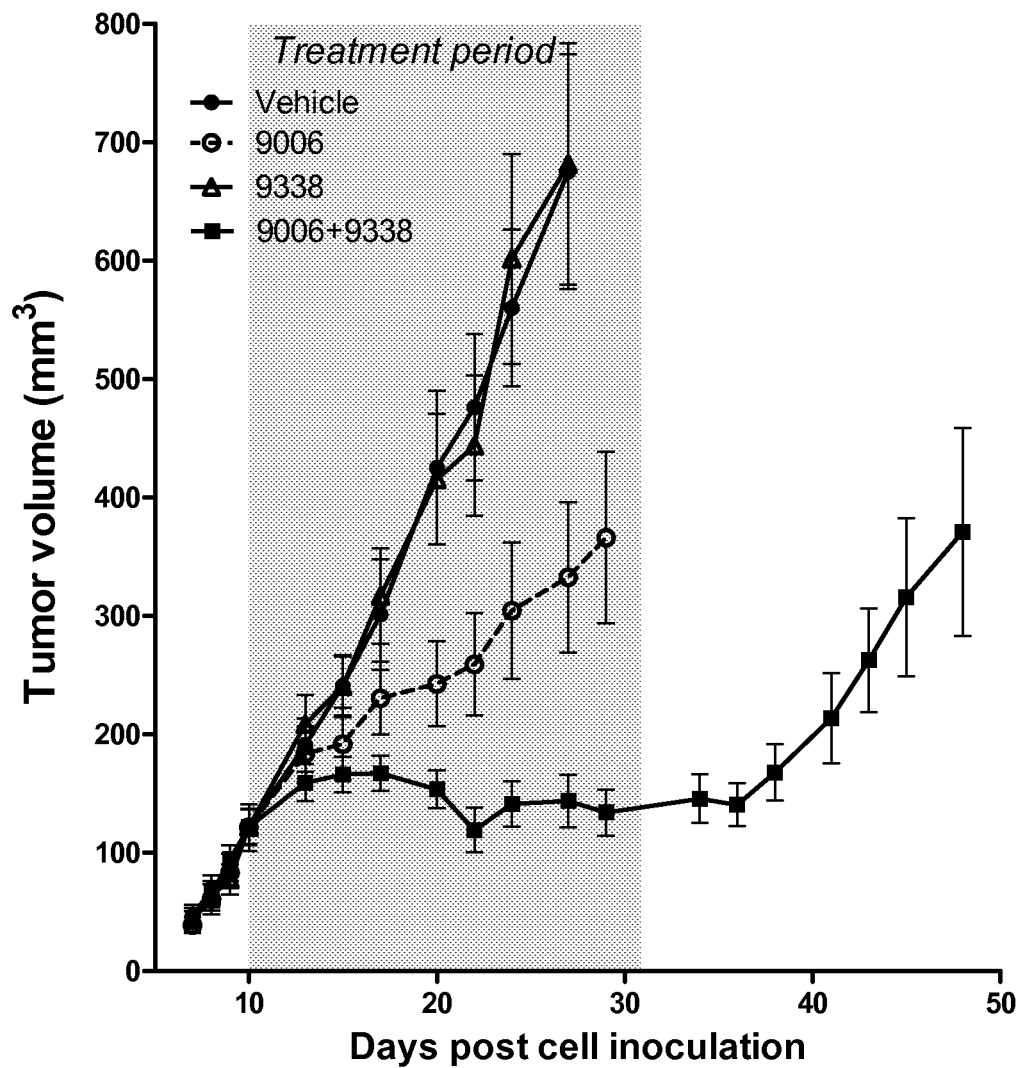
FIG. 15 shows the effect of chimeric 9006, 9338, 9006+ 9338, or vehicle treatment on tumor growth of xenografts of the human non-small cell lung cancer cell line EBC-1 in mice. The grey area denotes the treatment period.

Example 14: In Vivo Efficacy of the Chimeric 9006+9338 Antibody Mixture in a Human EBC-1 Tumor Xenograft Model This example demonstrates in vivo efficacy of the 9006+9338 antibody mixture in xenografts of the human MET-amplified non-small cell lung cancer cell line EBC-1.
Methods $5 \times 10^6$ EBC-1 cells were inoculated subcutaneously into the flanks of 8-9 week old female athymic nude mice. Tumors were measured three times weekly by caliper in two dimensions and tumor volume in $mm^3$ was calculated according to the formula: $(width)^2 \times length \times 0.5$. At an average tumor size of 120 $mm^3$, the mice were randomized and treatment was initiated. The mice were treated three times weekly for a total of ten treatments by intraperitoneal injection of vehicle buffer (10 mM sodium citrate, 150 mM sodium chloride, pH 6.0), monoclonal antibody 9006, monoclonal antibody 9338, or a 1:1 mixture of monoclonal antibodies 9006+9338, followed by an observation period. All antibody treatments were administered at 50 mg/kg total antibody concentration. Thus, 9006- and 9338-treated animals were dosed with 50 mg/kg of 9006 or 9338, respectively, whereas animals treated with 9006+9338 were dosed with a mixture containing 25 mg/kg of each antibody.
Results On day 10 post-inoculation, at an average tumor size of 120 $mm^3$, the mice were randomized into four groups of eight animals and treatment was initiated. As shown in FIG. 15, treatment with monoclonal antibody 9338 did not affect tumor growth in animals compared to the vehicle control. In contrast, treatment with 9006 resulted in tumor growth delay, whereas treatment with 9006+9338 induced growth stabilization during treatment and was superior to all other treatments in this model. Studies of the groups treated with vehicle or with 9006 or 9338 alone were closed during the treatment period due to tumor outgrowth or tumor related ulcerations, whereas animals in the 9006+9338 group completed treatment and observation for two to three weeks after the end of treatment.

Figure 16:
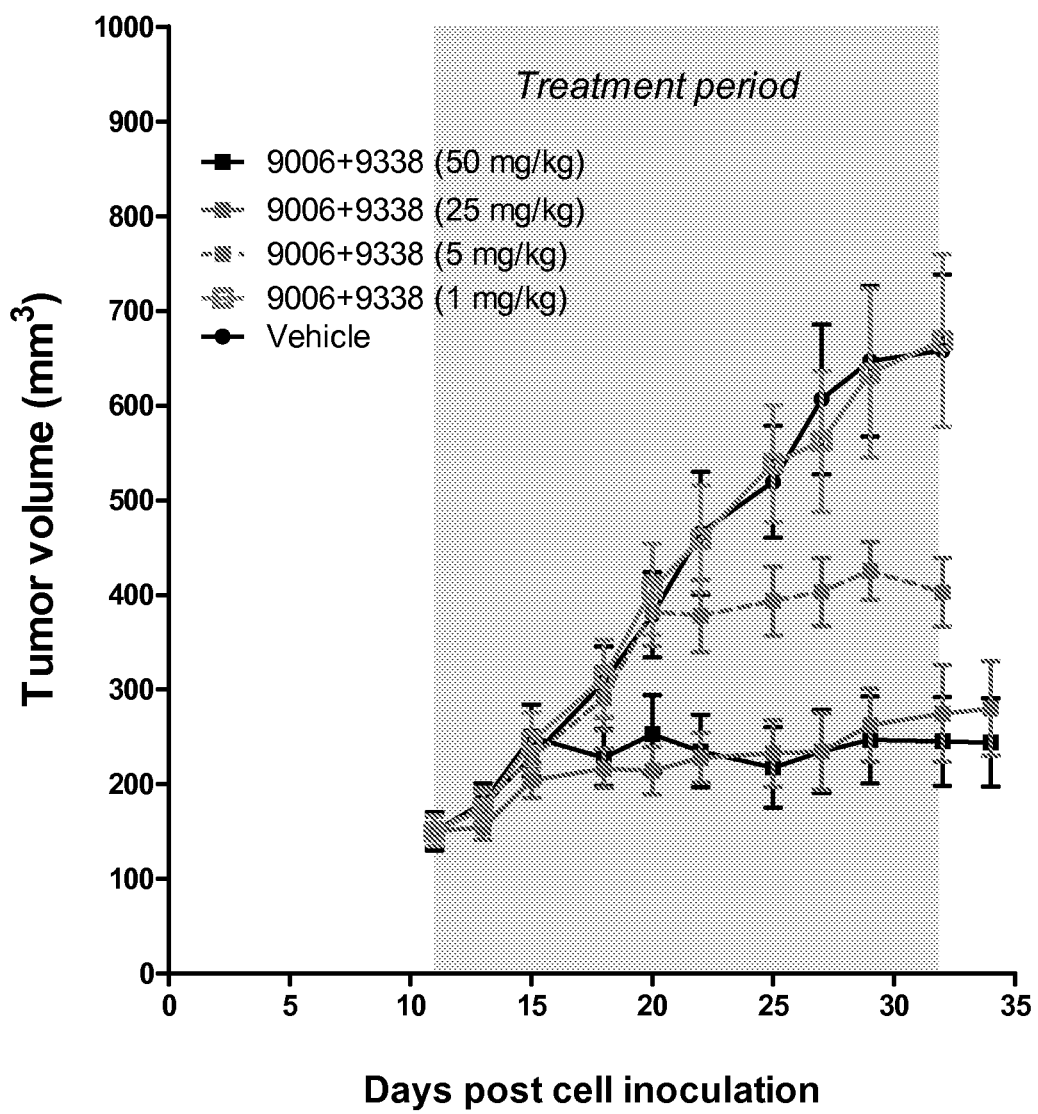
FIG. 16 shows the effect of treatment with chimeric 9006+9338 at four different concentrations compared to vehicle treatment on tumor growth of xenografts of the human non-small cell lung cancer cell line EBC-1 in mice. The grey area denotes the treatment period

Example 15: In Vivo Efficacy of Increasing Doses of the Chimeric 9006+9338 Antibody Mixture in a Human EBC-1 Tumor Xenograft Model This example demonstrates in vivo efficacy of increasing doses of the 9006+9338 antibody mixture in xenografts of the human MET-amplified non-small cell lung cancer cell line EBC-1.
Methods $5 \times 10^6$ EBC-1 cells were inoculated subcutaneously into the flanks of 8-9 week old female athymic nude mice. Tumors were measured three times weekly by caliper in two dimensions and tumor volume in $mm^3$ was calculated according to the formula: $(width)^2 \times length \times 0.5$. At an average tumor size of 150 $mm^3$, the mice were randomized and treatment was initiated. The mice were treated three times weekly for a total of ten treatments by intraperitoneal injection of vehicle buffer (10 mM sodium citrate, 150 mM sodium chloride, pH 6.0) or a 1:1 mixture of monoclonal antibodies 9006+9338, followed by an observation period. The 1:1 mixture of 9006+9338 was administered at 50, 25, 5 or 1 mg/kg total antibody concentration per injected dose.
Results On day 11 post-inoculation, at an average tumor size of 120 $mm^3$, the mice were randomized into five groups of ten animals and treatment was initiated. As shown in FIG. 16, tumor growth was not affected in animals treated with the lowest concentration of 9006+9338 (1 mg/kg) compared to vehicle control treated animals. Treatment with 5 mg/kg 9006+9338 resulted in tumor growth delay at later time points, whereas treatment with 25 or 50 mg/kg 9006+9338 induced comparable levels of potent tumor inhibition with growth stabilization.

Example 16: In Vivo Efficacy of the Chimeric 9006+9338 Antibody Mixture in a Human MKN-45 Tumor Xenograft Model This example demonstrates in vivo efficacy of the 9006+9338 antibody mixture in xenografts of the human MET-amplified gastric cancer cell line MKN-45.
Methods $5 \times 10^6$ MKN-45 cells were inoculated subcutaneously into the flanks of 8-9 week old female athymic nude mice. Tumors were measured three times weekly by caliper in two dimensions and tumor volume in mm$^3$ was calculated according to the formula: (width)$^2$×length×0.5. At an average tumor size of 80 mm$^3$, the mice were randomized and treatment was initiated. The mice were treated three times weekly for a total of ten treatments by intraperitoneal injection of vehicle buffer (10 mM sodium citrate, 150 mM sodium chloride, pH 6.0), monoclonal antibody 9006, monoclonal antibody 9338, or a 1:1 mixture of monoclonal antibodies 9006+9338, followed by an observation period. All antibody treatments were administered at 50 mg/kg total antibody concentration. Thus, 9006- and 9338-treated animals were dosed with 50 mg/kg of 9006 or 9338, respectively, whereas animals treated with 9006+9338 were dosed with a mixture containing 25 mg/kg of each antibody.

Results

Figure 17:
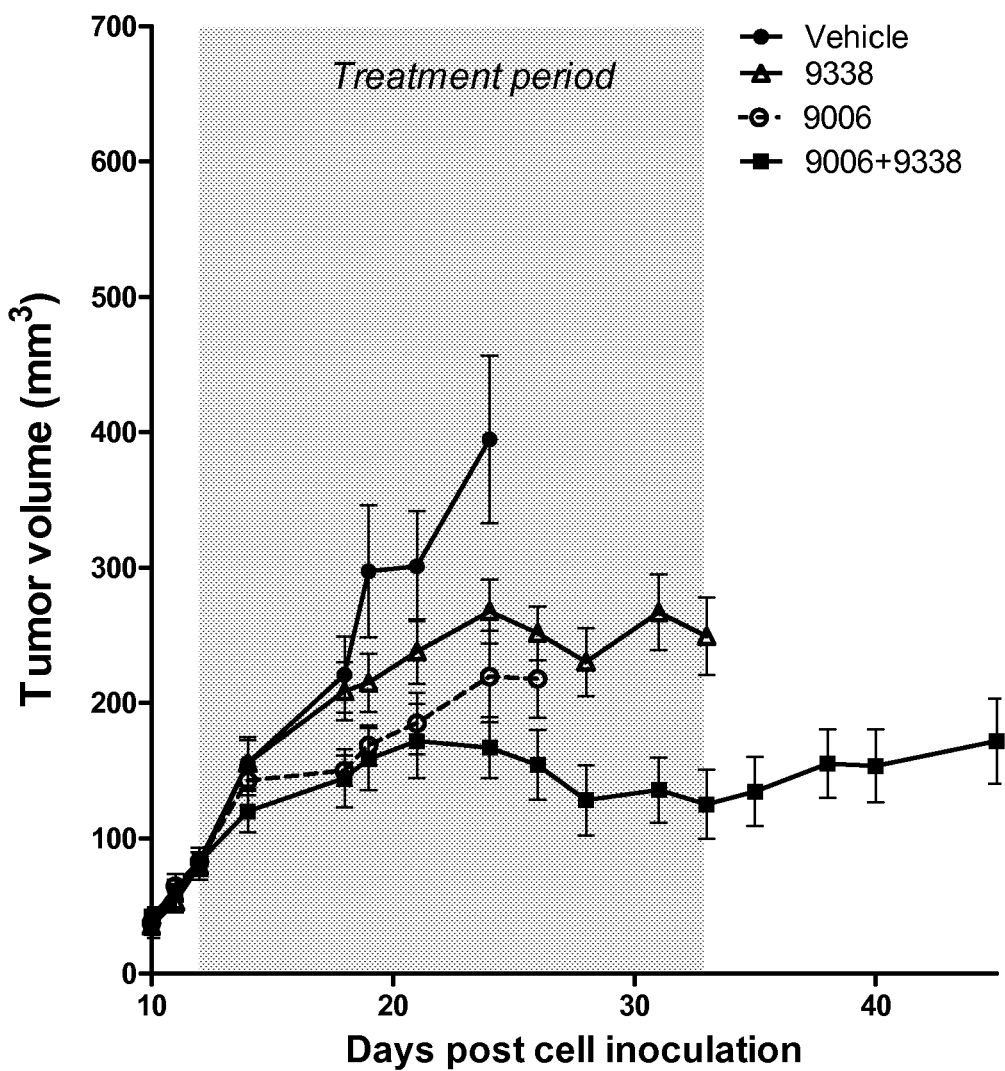
FIG. 17 shows the effect of chimeric 9006, 9338, 9006+ 9338, or vehicle treatment on tumor growth of xenografts of the human gastric cancer cell line MKN-45 in mice. The grey area denotes the treatment period.

On day 10 post-inoculation, at an average tumor size of 80 mm$^3$, the mice were randomized into four groups of eight animals and treatment was initiated. As shown in FIG. 17, tumor growth was slightly inhibited in animals treated with monoclonal antibody 9006 or 9338 alone compared to vehicle control treated animals. In contrast, treatment with 9006+9338 induced growth stabilization during treatment and was superior to all other treatments in this model. Studies of groups treated with vehicle or 9006 alone were closed during the treatment period due to tumor outgrowth or tumor related ulcerations, whereas the animals in the 9338 and 9006+9338 groups completed treatment. The 9006+9338 group was observed for 2 weeks after the end of treatment, and growth stabilization was retained during most of this period.

Example 17: In Vivo Efficacy of the Chimeric 9006+9338 Antibody Mixture in a Human SNU5 Tumor Xenograft Model This example demonstrates in vivo efficacy of the 9006+9338 antibody mixture in xenografts of the human MET-amplified gastric cancer cell line SNU5.

Methods

1×10$^7$ SNU5 cells were inoculated subcutaneously into the flanks of 8-9 week old female athymic nude mice. Tumors were measured three times weekly by caliper in two dimensions and tumor volume in mm$^3$ was calculated according to the formula: (width)$^2$×length×0.5. At an average tumor size of 165 mm$^3$', the mice were randomized and treatment was initiated. The mice were treated three times weekly for a total of ten treatments by intraperitoneal injection of vehicle buffer (10 mM sodium citrate, 150 mM sodium chloride, pH 6.0), monoclonal antibody 9006, monoclonal antibody 9338, or a 1:1 mixture of monoclonal antibodies 9006+9338, followed by an observation period. All antibody treatments were administered at 50 mg/kg total antibody concentration. Thus, 9006- and 9338-treated animals were dosed with 50 mg/kg of 9006 or 9338, respectively, whereas animals treated with 9006+9338 were dosed with a mixture containing 25 mg/kg of each antibody.

Results

Figure 18:
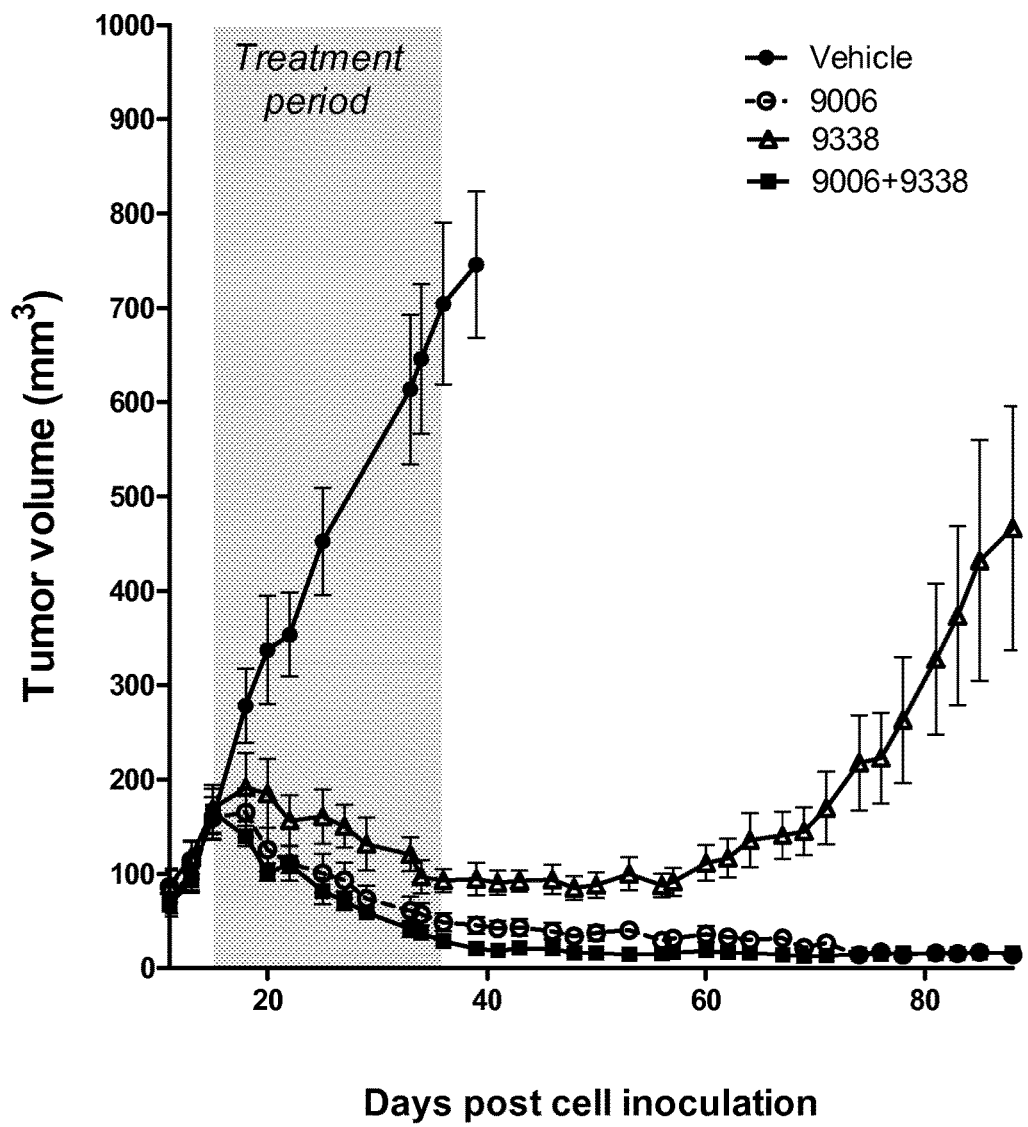
FIG. 18 shows the effect of chimeric 9006, 9338, 9006+ 9338, or vehicle treatment on tumor growth of xenografts of the human gastric cancer cell line SNU5 in mice. The grey area denotes the treatment period.

On day 15 post-inoculation, at an average tumor size of 165 mm$^3$, the mice were randomized into four groups of eight animals and treatment was initiated. As shown in FIG. 18, tumor regression was observed in animals treated with monoclonal antibody 9006 or 9338 or with the 9006+9338 antibody mixture compared to vehicle control treated animals. Treatment with 9006 or 9006+9338 was superior to treatment with 9338, and tumor regression was retained for more than 50 days after the end of treatment in the 9006- and 9006+9338-treated groups.

Example 18: In Vivo Efficacy of the Chimeric 9006+9338 Antibody Mixture in a Human Hepatocellular Carcinoma Patient-Derived Xenograft Model This example demonstrates in vivo efficacy of the 9006+9338 antibody mixture in a patient-derived xenograft model (LI1037) of human hepatocellular carcinoma (HCC).

Methods

The tumor source for model LI1037 is derived from a liver cancer patient tumor which was then maintained subcutaneously in nude mice. Tumors were minced into 3 mm$^3$ fragments, and one fragment was implanted subcutaneously at one front flank in each mouse. The animals were randomized into treatment groups when the tumor reached 220 mm$^3$ mean volume. The mice were treated three times weekly for a total of ten treatments by intraperitoneal injection of vehicle buffer (10 mM sodium citrate, 150 mM sodium chloride, pH 6.0) or a 1:1 mixture of monoclonal antibodies 9006+9338, followed by an observation period. All antibody treatments were administered at 50 mg/kg total antibody concentration. Thus, animals treated with 9006+9338 were dosed with a mixture containing 25 mg/kg of each antibody.

Results

Figure 19:
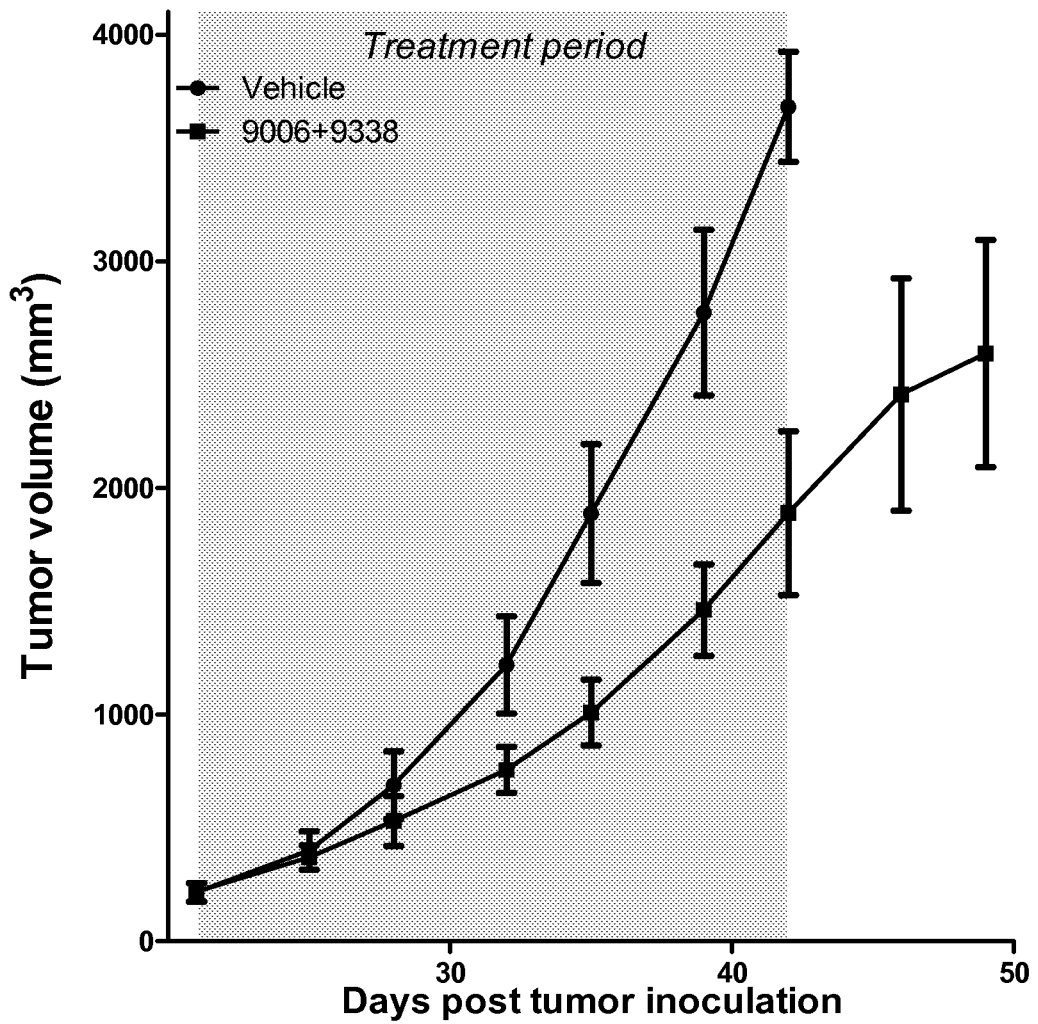
FIG. 19 shows the effect of the chimeric antibody mixture 9006+9338 or vehicle treatment on tumor growth of xenografts of the human HCC patient derived xenograft model LI1037 in mice. The grey area denotes the treatment period.

On day 21 post-inoculation, at an average tumor size of 220 mm$^3$, the mice were randomized into two groups of four animals and treatment was initiated. As shown in FIG. 19, tumor growth inhibition was observed in animals treated with the 9006+9338 antibody mixture compared to vehicle control treated animals.

Example 19: In Vivo Comparison of Chimeric and Humanized Antibody Mixtures in a Human EBC-1 Tumor Xenograft Model In this example the in vivo efficacies of the chimeric 9006+9338 and the humanized Hu9006+Hu9338 antibody mixtures are compared in xenografts of the human MET amplified non-small cell lung cancer cell line EBC-1.

Methods

5×10$^6$ EBC-1 cells were inoculated subcutaneously into the flank of 8-9 week old female athymic nude mice. Tumors were measured three times weekly by caliper in two dimensions and tumor volume in mm$^3$ was calculated according to the formula: (width)$^2$×length×0.5. On day 20 post cell inoculation at an average tumor size of ~130 mm$^3$, the mice were randomized into three groups of 10 animals and treatment was initiated. The mice were treated three times weekly with a total of ten intraperitoneal injections of vehicle buffer, a 1:1 mixture of chimeric 9006+9338 or humanized 9006+9338 (Hu9006+Hu9338) followed by an observation period. All antibody treatments were dosed at 50 mg/kg total antibody concentration. Thus, animals treated with 9006+9338 and Hu9006+Hu9338 were dosed with a mixture containing 25 mg/kg of each antibody.

Results

Figure 20:
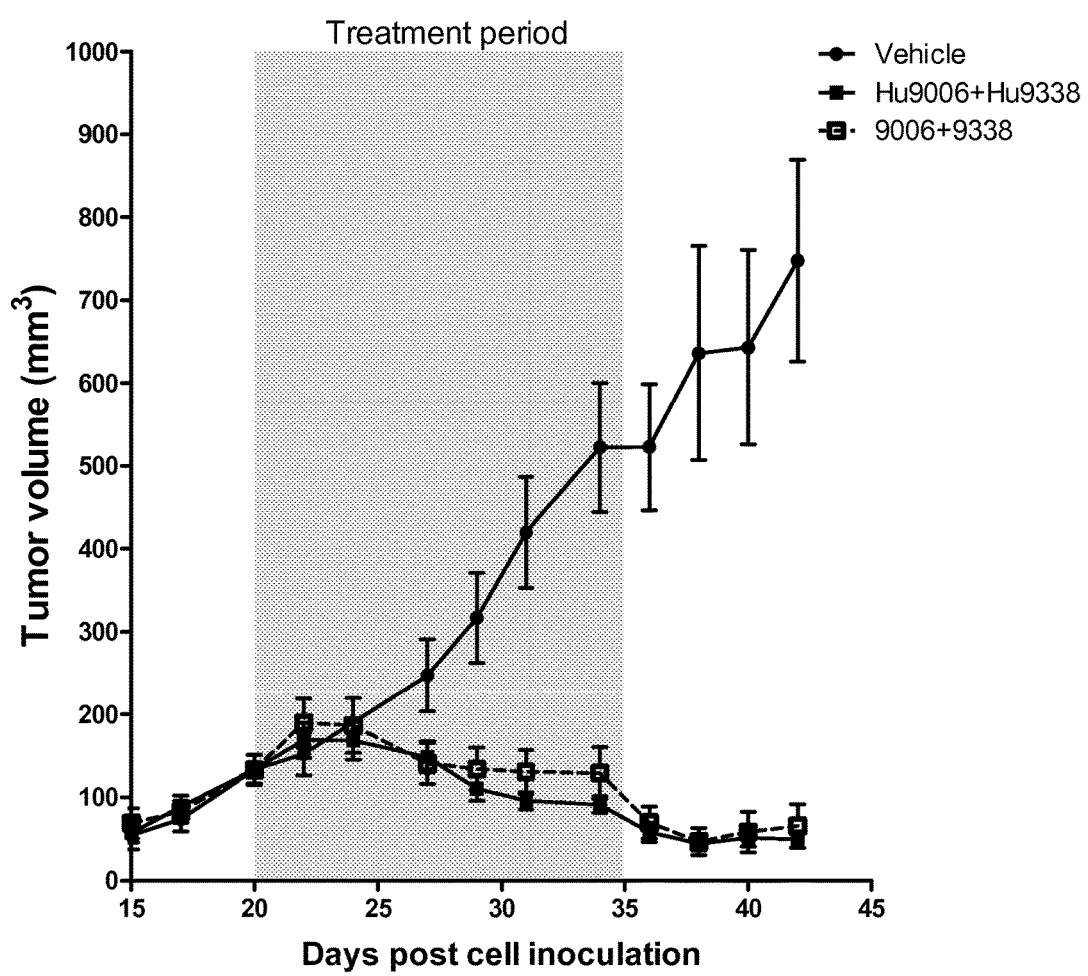
FIG. 20 shows the effect of 9006+9338, Hu9006+Hu9338 or vehicle treatment on tumor growth of xenografts of the human nonsmall cell lung cancer cell line EBC-1. The grey area denotes the treatment period.

As shown in FIG. 20, tumor regression was observed in animals treated with both 9006+9338 and Hu9006+Hu9338 as compared to vehicle control treated animals. The tumor inhibitory effect of Hu9006+Hu9338 and 9006+9338 appeared highly similar.

Example 20: In Vivo Comparison of Chimeric and Humanized Antibody Mixtures in a Human OE33 Tumor Xenograft Model In this example, the in vivo efficacies of the chimeric 9006+9338 and the humanized Hu9006+Hu9338 antibody mixtures are compared in xenografts of the human MET amplified esophagogastric cancer cell line OE33.

Methods

OE33 tumors were serially transplanted from previously established tumors.

Tumors had been passaged eight times at the time of study. Tumor fragments measuring ~1 mm$^3$ were transplanted subcutaneously into the flank of 8-9 week old female athymic nude mice. Tumors were measured three times weekly by caliper in two dimensions and tumor volume in mm$^3$ was calculated according to the formula: (width)$^2$×length×0.5. On day 30 post-tumor inoculation an average tumor size of 200 mm$^3$, the mice were randomized into three groups of seven animals and treatment was initiated. The mice were treated three times weekly with a total of ten treatments by intraperitoneal injection of vehicle buffer, a 1:1 mixture of chimeric 9006+9338 or humanized 9006+9338 (Hu9006+Hu9338) followed by an observation period. All antibody treatments were dosed at 30 mg/kg total antibody concentration. Thus, animals treated with 9006+9338 and Hu9006+Hu9338 were dosed with a mixture containing 15 mg/kg of each antibody.

Results

Figure 21:
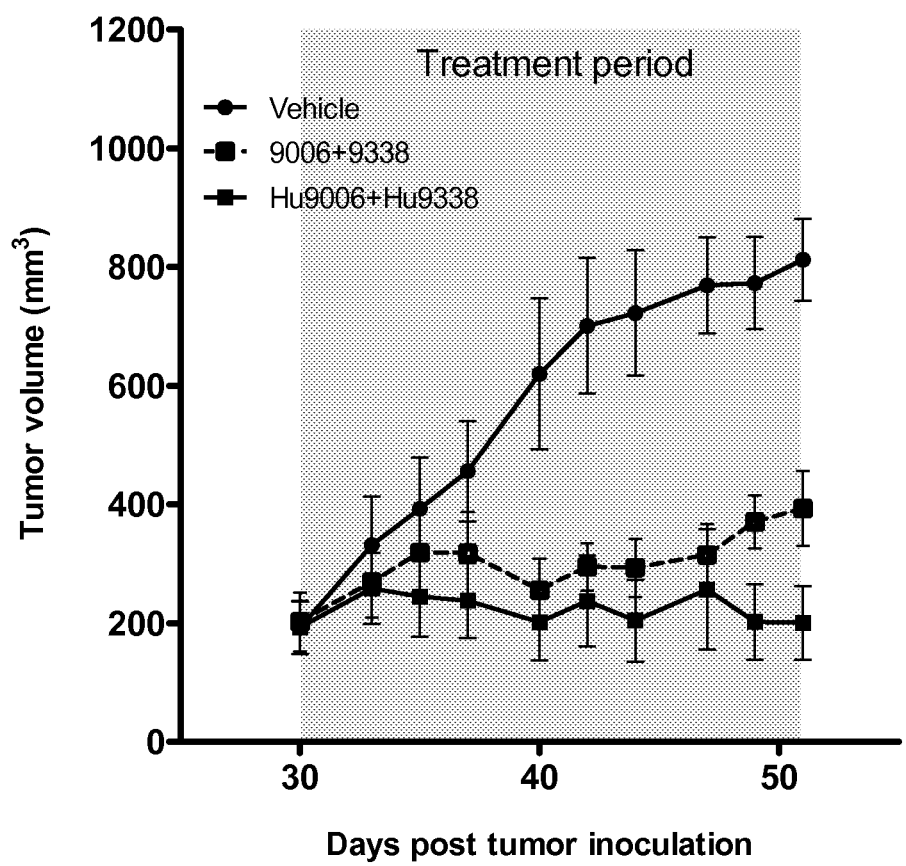
FIG. 21 shows the effect of chimeric 9006+9338, humanized 9006+9338 (Hu9006+Hu9338), or vehicle treatment on tumor growth of xenografts of the human esophagogastric cancer cell line OE33. The grey area denotes the treatment period.

As shown in FIG. 21, tumor regression was observed in animals treated with both 9006+9338 and Hu9006+Hu9338 compared to vehicle control treated animals and the growth curves are highly similar.

Example 21: In Vivo Comparison of the Monoclonal Antibody C8-H241 and the Hu9006+Hu9338 Antibody Mixture in Human Tumor Xenograft Models In this example, the in vivo efficacies of the Hu9006+Hu9338 antibody mixture and the comparator monoclonal antibody C8-H241 (see Table 4) are compared in xenografts of the human MET amplified non-small cell lung cancer cell line EBC-1 and the human MET amplified gastric cancer cell line Hs746T, which also harbors a MET exon 14 deletion.

Methods

5×10$^6$ EBC-1 cells or 3.7×10$^6$ Hs746T cells were inoculated subcutaneously into the flank of female athymic mice. Tumors were measured three times weekly by caliper in two dimensions and tumor volume in mm3 was calculated according to the formula: (width)$^2$×length×0.5. At an average tumor size of 140 mm$^3$ for EBC-1 and 120 mm$^3$ for Hs746T the mice were randomized and treatment was initiated.

Treatment Schedule for EBC-1:

The mice were treated three times weekly with a total of ten intraperitoneal injections of vehicle buffer, monoclonal antibody C8-H241, or a 1:1 mixture of monoclonal antibodies Hu9006+Hu9338 followed by an observation period. After 21 days of observation, remaining mice in the C8-H241 group were re-treated with Hu9006+Hu9338 three times weekly until study termination on day 139 after tumor cell inoculation.

Treatment Schedule for Hs746T:

The mice were treated three times weekly with a total of ten intraperitoneal injections of vehicle buffer, monoclonal antibody C8-H241, monoclonal antibody Hu9006, monoclonal antibody Hu9338 or a 1:1 mixture of monoclonal antibodies Hu9006+Hu9338. After a one week observation period all remaining mice in the Hu9006, Hu9338 and C8-H241 groups were treated with a single dose of Hu9006+Hu9338 and observed for 9 days.

All antibody treatments were dosed at 50 mg/kg total antibody concentration. Thus, C8-H241, Hu9006 and Hu9338 treated animals were dosed with 50 mg/kg antibody whereas animals treated with Hu9006+Hu9338 were dosed with a mixture containing 25 mg/kg of each antibody.

Results

Figure 22:
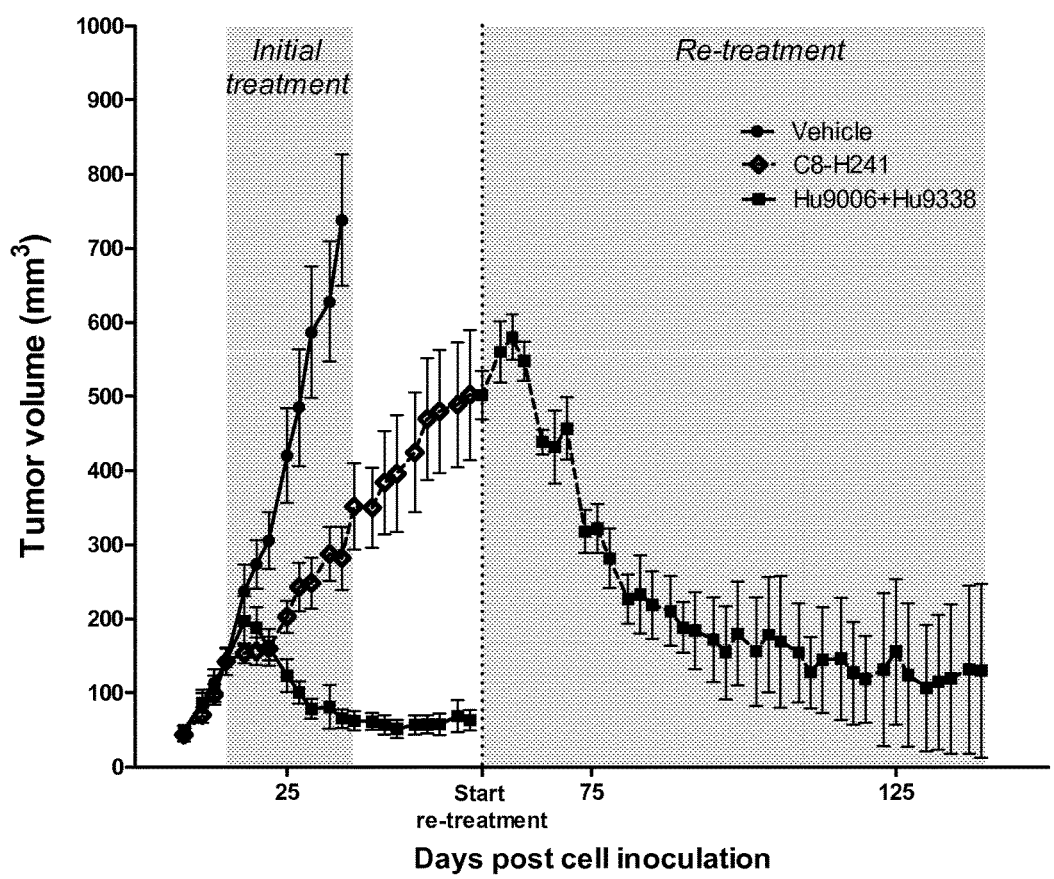
FIG. 22 shows the effect of C8-H241, Hu9006+Hu9338 or vehicle treatment on tumor growth of xenografts of the human non-small cell lung cancer cell line EBC-1 (n=10 mice per group). Grey areas denote the treatment periods. Dotted line denotes initiation of re-treatment of remaining mice (n=4) in the C8-H241 treated group with Hu9006+ Hu9338.

EBC-1:

On day 15 post-inoculation at an average tumor size of 140 mm$^3$ the mice were randomized into three groups of ten animals and treatment was initiated. As shown in FIG. 22, a limited response was observed in mice treated with C8-H241 compared to vehicle control treated animals. In contrast, treatment with Hu9006+Hu9338 induced tumor regression. 21 days after the last dose, at an average tumor volume of 500 mm$^3$, the remaining mice in the C8-H241 treated group were re-treated with Hu9006+Hu9338. FIG. 22 also shows that the mice responded with tumor regression upon the secondary treatment.

Figure 23:
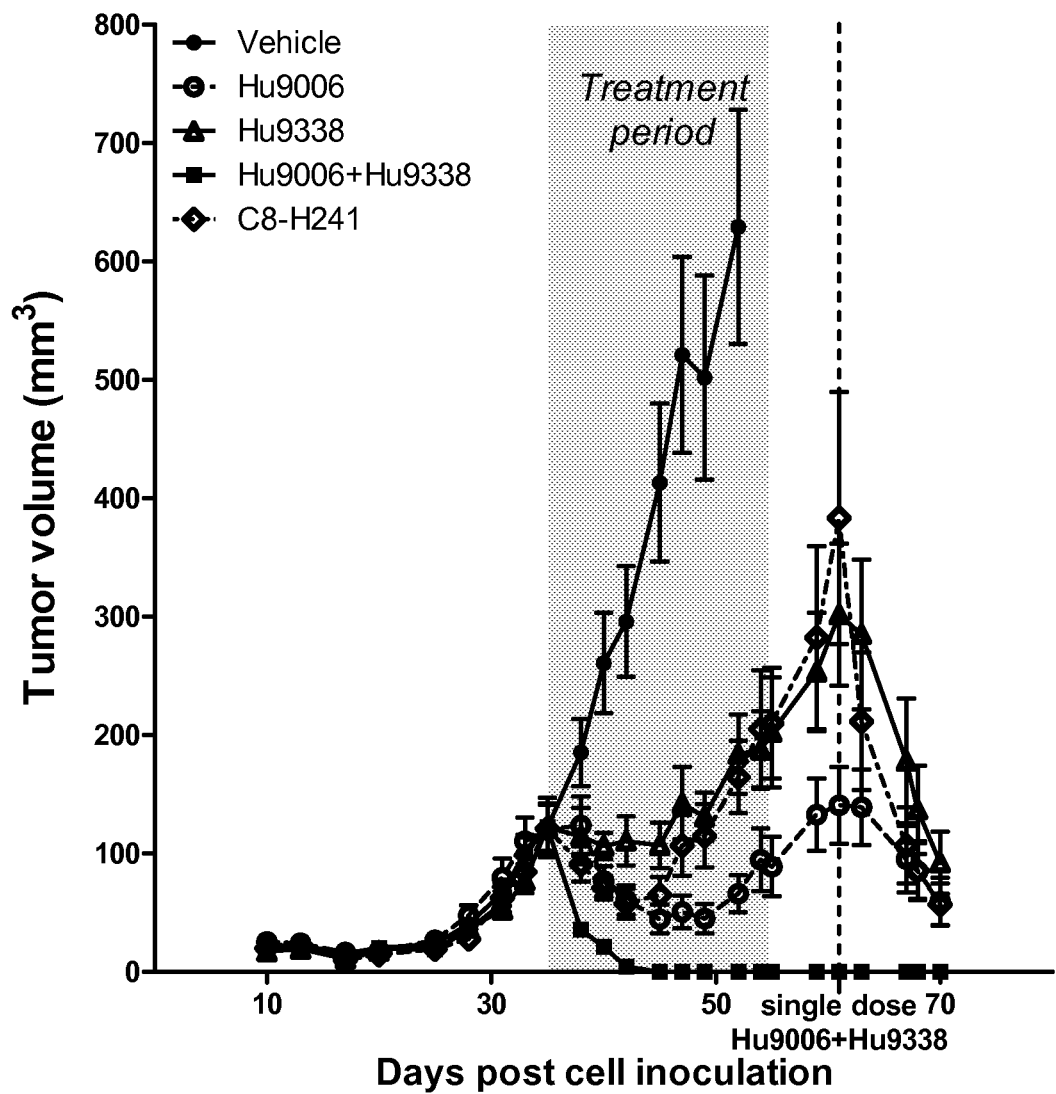
FIG. 23 shows the effect of C8-H241, Hu9006, Hu9338, Hu9006+Hu9338 or vehicle treatment on tumor growth of xenografts of the human gastric cancer cell line Hs746T (n=8 mice per group). Grey area denotes the initial treatment period. Dotted line denotes single dose re-treatment with Hu9006+Hu9338 of remaining mice in the C8-H241, Hu9006 and Hu9338 groups.

Hs746T:

On day 35 post-inoculation at an average tumor size of 120 mm$^3$ the mice were randomized into five groups of eight animals and treatment was initiated. As shown in FIG. 23, a limited initial inhibitory response was observed in mice treated with C8-H241, Hu9006 or Hu9338 compared to vehicle control treated animals, but approximately halfway through the treatment period, the tumors started to re-grow. In contrast, treatment with Hu9006+Hu9338 induced tumor regression and complete tumor eradication in all eight mice treated. Nine days after the last dose, the remaining mice in the C8-H241, Hu9006 and Hu9338 treated groups were re-treated with a single dose of Hu9006+Hu9338. FIG. 23 also shows that the mice responded with tumor regression upon the secondary treatment.

Example 22: In Vivo Comparison of the Monoclonal Antibody C8-H241 and the Hu9006+Hu9338 Antibody Mixture in Four Human Patient Derived Xenograft Models In this example, the in vivo efficacy of the Hu9006+Hu9338 antibody mixture and the comparator monoclonal antibody C8-H241 (see Table 4) were compared in four human MET amplified non-small cell lung cancer (NSCLC) patient derived xenograft models.

Methods

Each mouse was inoculated subcutaneously at the flank with primary NSCLC tissue fragments from model LXFA0526, LU0858, LU1901 or LU2503 (2-3 mm in diameter) for tumor development. Tumors were measured two times weekly by caliper in two dimensions and tumor volume in mm$^3$ was calculated according to the formula: (width)$^2$×length×0.5.

When average tumor size reached 100-200 mm$^3$, mice were randomly assigned into three groups (n=5 to 8 mice per group) and treatment was initiated. Mice were treated three times weekly for a total of ten intraperitoneal injections with either C8-H241 monoclonal antibody, Hu9006+Hu9338 antibody mixture (single monoclonal antibodies mixed at equal ratio) or vehicle buffer control followed by an observation period of up to three weeks.

All antibody treatments were dosed at 50 mg/kg total antibody concentration. Thus, C8-H241 treated animals were dosed with 50 mg/kg antibody whereas animals treated with Hu9006+Hu9338 were dosed with a mixture containing 25 mg/kg of each antibody.

Results

Figure 24:
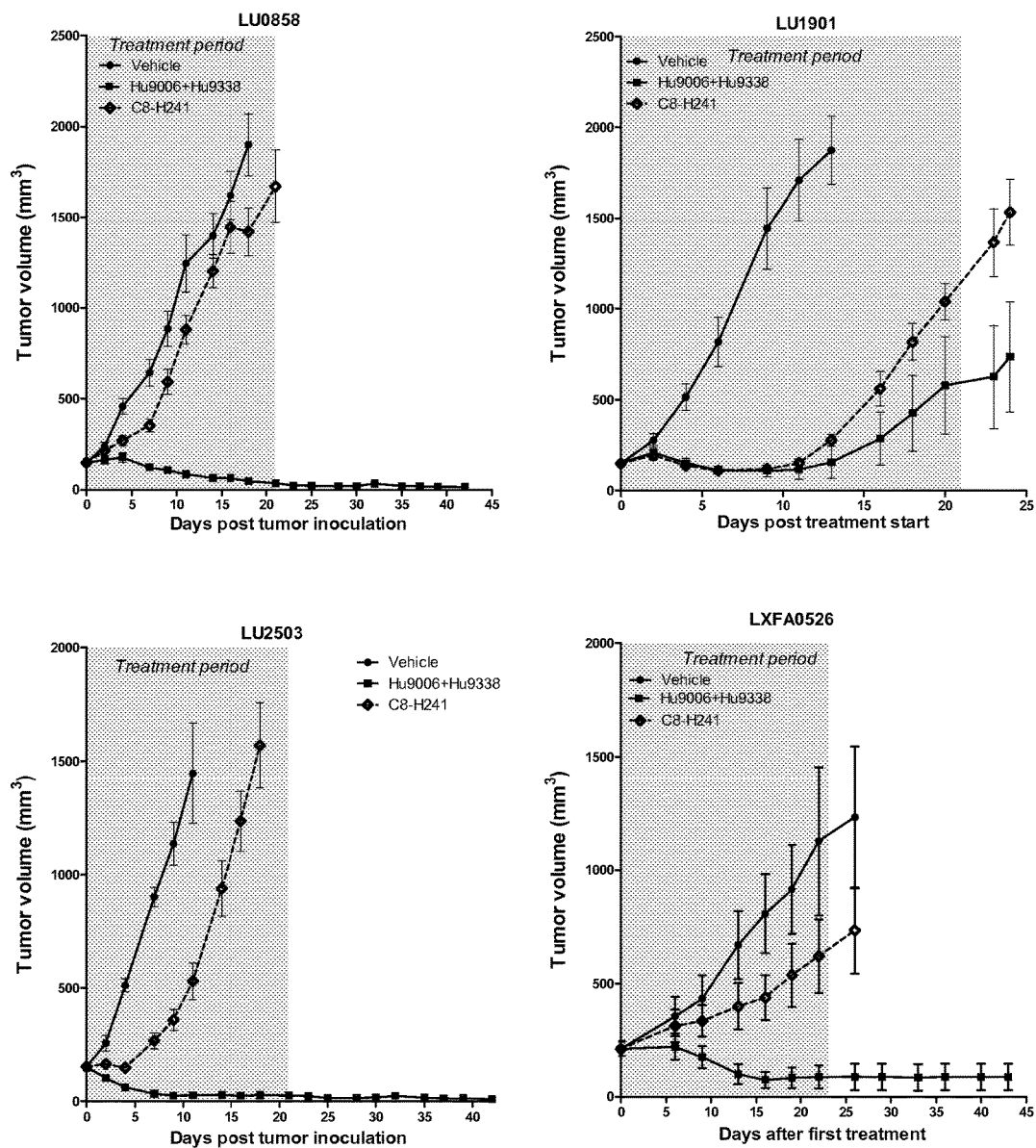
FIG. 24 shows the effect of C8-H241, Hu9006+Hu9338 or vehicle treatment on tumor growth in four patient derived xenograft models (n=5 mice per group for LU0858, L1901 and LU2503; n=8 mice per group for LXFA0526). Grey area denotes the treatment period.

As shown in FIG. 24, varying responses were observed in the four models upon C8-H241 treatment. In contrast, treatment with Hu9006+Hu9338 induced tumor regression in all 4 models with superior efficacy and/or delayed time to progression compared to C8-H241. C8-H241 was previously reported to be highly efficacious in a different MET amplified primary MET amplified xenograft NSCLC model (LXFA-1647) (Liu et al. Clin Cancer Res. 20:6059-6070 (2014)).

Example 23: In Vivo Comparison of Balanced and Skewed Ratio Compositions of the Hu9006+Hu9338 Antibody Mixture in a Human Tumor Xenograft Model In this example, the in vivo efficacy of mixtures consisting of different ratios of the two antibodies Hu9006 and Hu9338 was compared in xenografts of the human MET amplified non-small cell lung cancer cell line EBC-1.

Methods $5 \times 10^6$ EBC-1 cells were inoculated subcutaneously into the flank of 8-9 week old female athymic nude mice. Tumors were measured three times weekly by caliper in two dimensions and tumor volume in $mm^3$ was calculated according to the formula: $(width)^2 \times length \times 0.5$. On day 13 post-inoculation at an average tumor size of 150 $mm^3$ the mice were randomized into three groups of ten animals and treatment was initiated. The mice were treated three times weekly with a total of ten intraperitoneal injections of vehicle buffer, 1:1, 2:1 or 1:2 skewed antibody ratio mixtures of monoclonal antibodies Hu9006+Hu9338 followed by an observation period. Antibody treatments were dosed at either 50 mg/kg or, for the skewed antibody ratio mixtures, 10 mg/kg total antibody concentration as follows: 1:1 ratio dosed animals were dosed with a mixture containing 25 mg/kg of each antibody. 1:2 ratio dosed animals were either dosed with a mixture containing 3 mg/kg Hu9006 and 7 mg/kg Hu9338 for a total dosing of 10 mg/kg or with a mixture containing 17 mg/kg Hu9006 and 33 mg/kg Hu9338 for a total dosing of 50 mg/kg. Analogously, 2:1 ratio dosed animals were either dosed with a mixture containing 7 mg/kg Hu9006 and 3 mg/kg Hu9338 for a total dosing of 10 mg/kg or with a mixture containing 33 mg/kg Hu9006 and 17 mg/kg Hu9338 for a total dosing of 50 mg/kg.

Results

Figure 25:
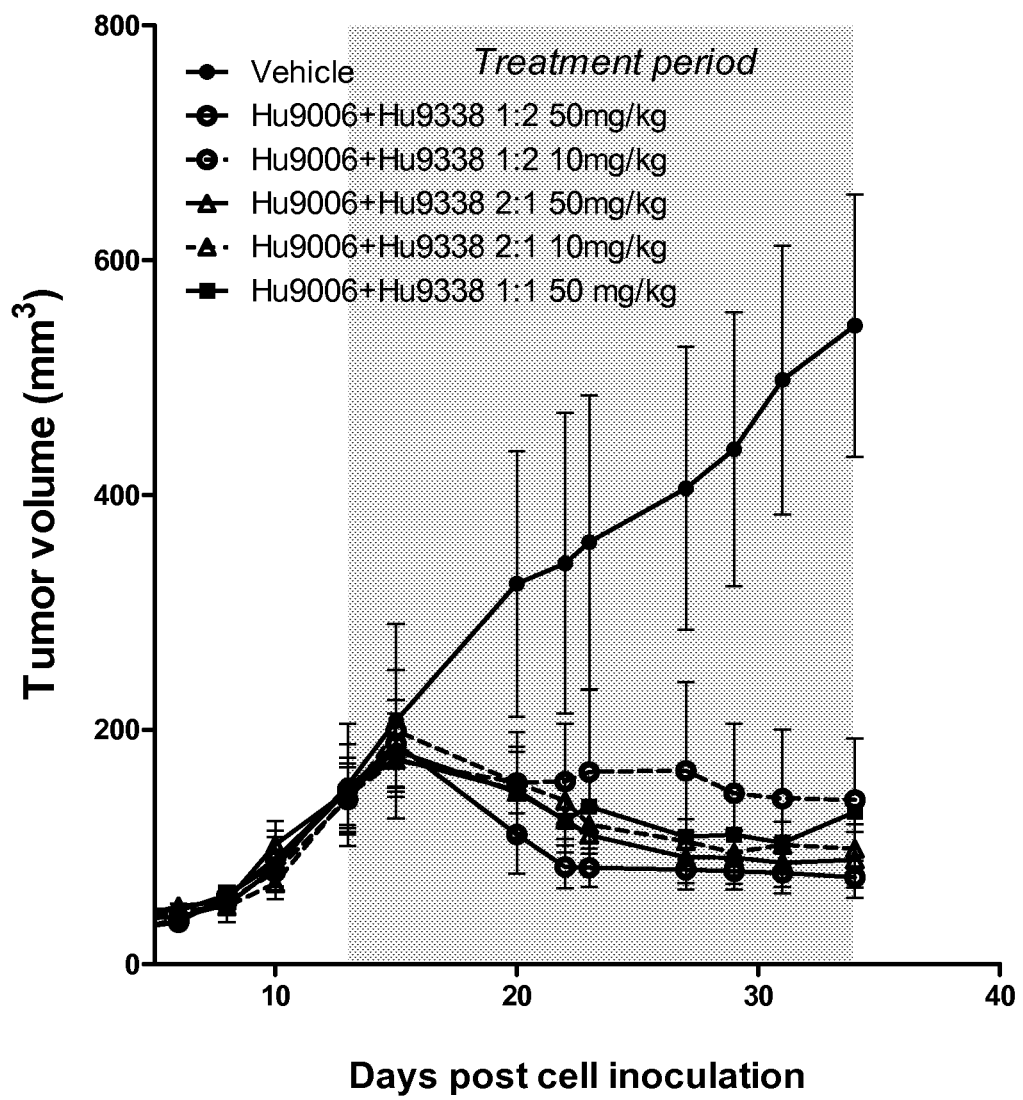
FIG. 25 shows the effect of balanced or skewed ratios of Hu9006+Hu9338 or vehicle treatment on tumor growth of xenografts of the human non-small cell lung cancer cell line EBC-1 (n=8 mice per group). Grey area denotes the treatment period.
Figure 30:
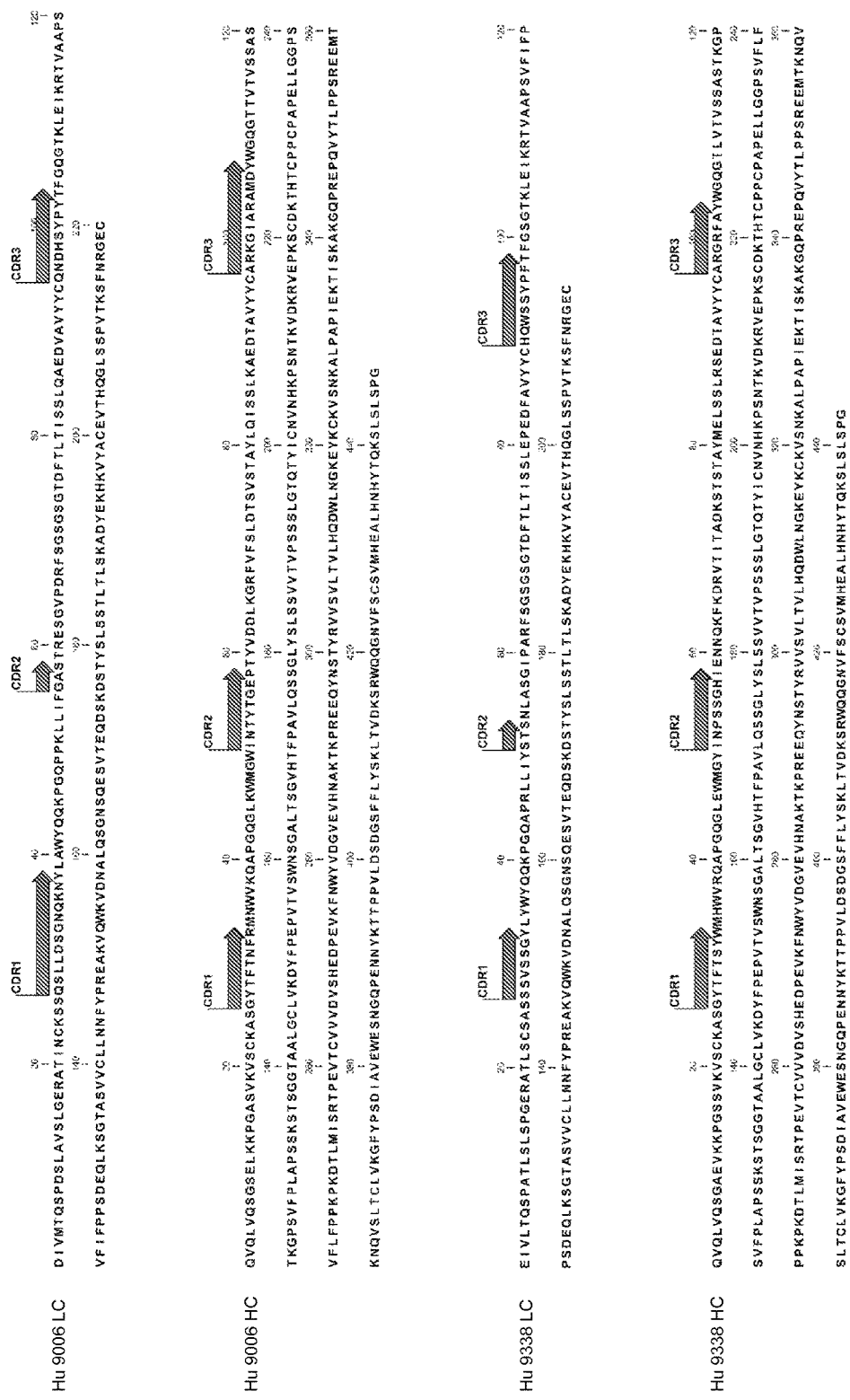
FIG. 30 shows the full-length light and heavy chain amino acid sequences of humanized antibody 9006 (SEQ ID NOs: 33 and 34, respectively) and humanized antibody 9338 (SEQ ID NOs: 35 and 36, respectively). The CDRs are marked by arrows.
Figure 31:
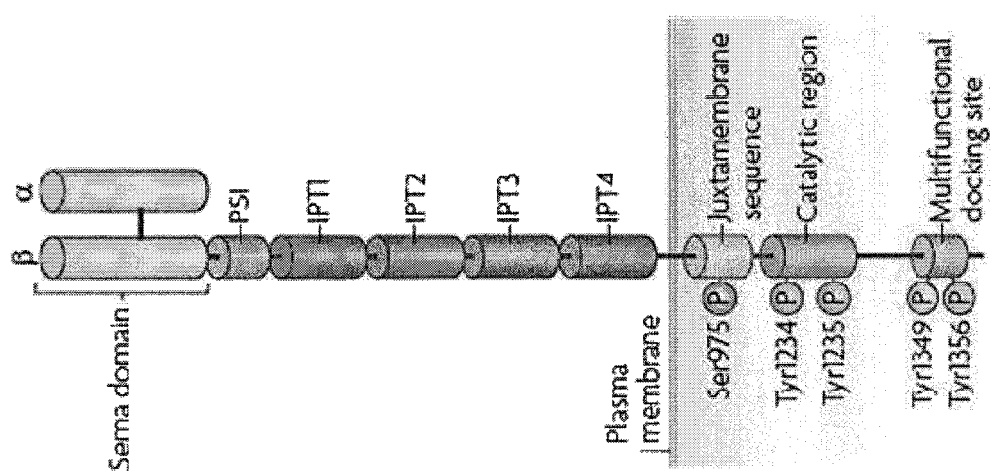
FIG. 31 shows the structure of MET.

As shown in FIG. 25, treatment with Hu9006+Hu9338 at both balanced and skewed ratios and at both doses induced tumor regression. The level of tumor regression appeared similar for all tested antibody treatments indicating that Hu9006+Hu9338 yields a robust and consistent tumor growth inhibition at both balanced and skewed single antibody compositions.

TABLE 11

SEQ ID NO Chart

| SEQ ID NO | Sequence |
|---|---|
| 1 | human MET isoform 1 amino acid sequence |
| 2 | human MET isoform 2 amino acid sequence |
| 3 | chicken MET amino acid sequence |
| 4 | murine MET amino acid sequence |
| 5 | chimeric 9006 heavy chain variable domain nucleic acid sequence |
| 6 | chimeric 9006 heavy chain variable domain amino acid sequence |
| 7 | chimeric 9006 light chain variable domain nucleic acid sequence |
| 8 | chimeric 9006 light chain variable domain amino acid sequence |
| 9 | chimeric 9338 heavy chain variable domain nucleic acid sequence |
| 10 | chimeric 9338 heavy chain variable domain amino acid sequence |
| 11 | chimeric 9338 light chain variable domain nucleic acid sequence |
| 12 | chimeric 9338 light chain variable domain amino acid sequence |
| 13 | humanized 9006 heavy chain variable domain nucleic acid sequence |
| 14 | humanized 9006 heavy chain variable domain amino acid sequence |
| 15 | humanized 9006 light chain variable domain nucleic acid sequence |
| 16 | humanized 9006 light chain variable domain amino acid sequence |
| 17 | humanized 9338 heavy chain variable domain nucleic acid sequence |
| 18 | humanized 9338 heavy chain variable domain amino acid sequence |
| 19 | humanized 9338 light chain variable domain nucleic acid sequence |
| 20 | humanized 9338 light chain variable domain amino acid sequence |
| 21 | 9006 heavy chain CDR1 amino acid sequence |
| 22 | 9006 heavy chain CDR2 amino acid sequence |
| 23 | 9006 heavy chain CDR3 amino acid sequence |
| 24 | 9006 light chain CDR1 amino acid sequence |
| 25 | 9006 light chain CDR2 amino acid sequence |
| 26 | 9006 light chain CDR3 amino acid sequence |
| 27 | 9338 heavy chain CDR1 amino acid sequence |
| 28 | 9338 heavy chain CDR2 amino acid sequence |
| 29 | 9338 heavy chain CDR3 amino acid sequence |
| 30 | 9338 light chain CDR1 amino acid sequence |
| 31 | 9338 light chain CDR2 amino acid sequence |
| 32 | 9338 light chain CDR3 amino acid sequence |
| 33 | humanized 9006 light chain amino acid sequence |
| 34 | humanized 9006 heavy chain amino acid sequence |
| 35 | humanized 9338 light chain amino acid sequence |
| 36 | humanized 9338 heavy chain amino acid sequence |

```
List of Sequences

SEQ ID NO: 1 (human MET isoform 1 amino acid sequence):
MKAPAVLAPGILVLLFTLVQRSNGECKEALAKSEMNVNMKYQLPNFTAETPIQNVIL
HEHHIFLGATNYIYVLNEEDLQKVAEYKTGPVLEHPDCFPCQDCSSKANLSGGVWKD
NINMALVVDTYYDDQLISCGSVNRGTCQRHVFPHNHTADIQSEVHCIFSPQIEEPSQ
CPDCVVSALGAKVLSSVKDRFINFFVGNTINSSYFPDHPLHSISVRRLKETKDGFMF
LTDQSYIDVLPEFRDSYPIKYVHAFESNNFIYFLTVQRETLDAQTFHTRIIRFCSIN
```

List of Sequences

SGLHSYMEMPLECILTEKRKKRSTKKEVFNILQAAYVSKPGAQLARQIGASLNDDIL
FGVFAQSKPDSAEPMDRSAMCAFPIKYVNDFFNKIVNKNNVRCLQHFYGPNHEHCFN
RTLLRNSSGCEARRDEYRTEFTTALQRVDLFMGQFSEVLLTSISTFIKGDLTIANLG
TSEGRFMQVVVSRSGPSTPHVNFLLDSHPVSPEVIVEHTLNQNGYTLVITGKKITKI
PLNGLGCRHFQSCSQCLSAPPFVQCGWCHDKCVRSEECLSGTWTQQICLPAIYKVFP
NSAPLEGGTRLTICGWDFGFRRNNKFDLKKTRVLLGNESCTLTLSESTMNTLKCTVG
PAMNKHFNMSIIISNGHGTTQYSTFSYVDPVITSISPKYGPMAGGTLLTLTGNYLNS
GNSRHISIGGKTCTLKSVSNSILECYTPAQTISTEFAVKLKIDLANRETSIFSYRED
PIVYEIHPTKSFISGGSTITGVKNLNSVSVPRMVINVHEAGRNFTVACQHRSNSEI
ICCTTPSLQQLNLQLPLKTKAFFMLDGILSKYFDLIYVHNPVFKPFEKPVMISMGNE
NVLEIKGNDIDPEAVKGEVLKVGNKSCENIHLHSEAVLCTVPNDLLKLNSELNIEWK
QAISSTVLGKVIVQPDQNFTGLIAGVVSISTALLLLLGFFLWLKKRKQIKDLGSELV
RYDARVHTPHLDRLVSARSVSPTTEMVSNESVDYRATFPEDQFPNSSQNGSCRQVQY
PLTDMSPILTSGDSDISSPLLQNTVHIDLSALNPELVQAVQHVVIGPSSLIVHFNEV
IGRGHFGCVYHGTLLDNDGKKIHCAVKSLNRITDIGEVSQFLTEGIIMKDFSHPNVL
SLLGICLRSEGSPLVVLPYMKHGDLRNFIRNETHNPTVKDLIGFGLQVAKGMKYLAS
KKFVHRDLAARNCMLDEKFTVKVADFGLARDMYDKEYYSVHNKTGAKLPVKWMALES
LQTQKFTTKSDVWSFGVLLWELMTRGAPPYPDVNTFDITVYLLQGRRLLQPEYCPDP
LYEVMLKCWHPKAEMRPSFSELVSRISAIFSTFIGEHYVHVNATYVNVKCVAPYPSL
LSSEDNADDEVDTRPASFWETS

SEQ ID NO: 2 (human MET isoform 2 amino acid sequence):
MKAPAVLAPGILVLLFTLVQRSNGECKEALAKSEMNVNMKYQLPNFTAETPIQNVIL
HEHHIFLGATNYIYVLNEEDLQKVAEYKTGPVLEHPDCFPCQDCSSKANLSGGVWKD
NINMALVVDTYYDDQLISCGSVNRGTCQRHVFPHNHTADIQSEVHCIFSPQIEEPSQ
CPDCVVSALGAKVLSSVKDRFINFFVGNTINSSYFPDHPLHSISVRRLKETKDGFMF
LTDQSYIDVLPEFRDSYPIKYVHAFESNNFIYFLTVQRETLDAQTFHTRIIRFCSIN
SGLHSYMEMPLECILTEKRKKRSTKKEVFNILQAAYVSKPGAQLARQIGASLNDDIL
FGVFAQSKPDSAEPMDRSAMCAFPIKYVNDFFNKIVNKNNVRCLQHFYGPNHEHCFN
RTLLRNSSGCEARRDEYRTEFTTALQRVDLFMGQFSEVLLTSISTFIKGDLTIANLG
TSEGRFMQVVVSRSGPSTPHVNFLLDSHPVSPEVIVEHTLNQNGYTLVITGKKITKI
PLNGLGCRHFQSCSQCLSAPPFVQCGWCHDKCVRSEECLSGTWTQQICLPAIYKVFP
NSAPLEGGTRLTICGWDFGFRRNNKFDLKKTRVLLGNESCTLTLSESTMNTLKCTVG
PAMNKHFNMSIIISNGHGTTQYSTFSYVDPVITSISPKYGPMAGGTLLTLTGNYLNS
GNSRHISIGGKTCTLKSVSNSILECYTPAQTISTEFAVKLKIDLANRETSIFSYRED
PIVYEIHPTKSFISTWWKEPLNIVSFLFCFASGGSTITGVKNLNSVSVPRMVINVH
EAGRNFTVACQHRSNSEIICCTTPSLQQLNLQLPLKTKAFFMLDGILSKYFDLIYVH
NPVFKPFEKPVMISMGNENVLEIKGNDIDPEAVKGEVLKVGNKSCENIHLHSEAVLC
TVPNDLLKLNSELNIEWKQAISSTVLGKVIVQPDQNFTGLIAGVVSISTALLLLLGF
FLWLKKRKQIKDLGSELVRYDARVHTPHLDRLVSARSVSPTTEMVSNESVDYRATFP
EDQFPNSSQNGSCRQVQYPLTDMSPILTSGDSDISSPLLQNTVHIDLSALNPELVQA
VQHVVIGPSSLIVHFNEVIGRGHFGCVYHGTLLDNDGKKIHCAVKSLNRITDIGEVS
QFLTEGIIMKDFSHPNVLSLLGICLRSEGSPLVVLPYMKHGDLRNFIRNETHNPTVK
DLIGFGLQVAKGMKYLASKKFVHRDLAARNCMLDEKFTVKVADFGLARDMYDKEYYS
VHNKTGAKLPVKWMALESLQTQKFTTKSDVWSFGVLLWELMTRGAPPYPDVNTFDIT
VYLLQGRRLLQPEYCPDPLYEVMLKCWHPKAEMRPSFSELVSRISAIFSTFIGEHYV
HVNATYVNVKCVAPYPSLLSSEDNADDEVDTRPASFWETS SEQ ID NO: 3 (chicken MET amino acid sequence):
MKPVTAYPSGIILFLFALLQRSHGQCKEAAKKSEMNLNVKYDLPNFITETPIQNVVL
YKHHVYIGAVNKIYVLNETLQNISVYKTGPILESPGCAPCEDCKDKANLSNSVWKDN
VNMALLLETYYDDQLISCGSVSGGVCHRHIIPPDNPADIESEVHCMYSPQVDGEADN
CPDCVVSTLGTKVLVTEKDRFVNFFVGNTMTSAFQPPHVLHSISVRRLKETQDGFEF
LTDQSYIDILPQFRDSYPIKYVHAFEHDHFVYFLTVQRESLDSQTFHTRIIRFCTLD
SEMRSYMEMPLECIFTEKRRKRSIRKEVFNILQAAYVSKPGAALAHEMGLGLIDDIL
YGVFAQTNQIPQEPTNRSAVCAVSVRTINEFFNKIVDKQNMKCLQHFYGKDSKYCLN
RAFSRNASYCRAQDDEYRLEVTTPLQRVDLFMGQFNNILLTSISVFTKGNLTIANLG
TSEGRFMQIVVSRSEPTAPHVSFQLDSHAVSPQVVVEQSAAADGYTLVVIGKKITKV
PLNGPGCHHFQSCSQCLLAPAFMRCGWCGQQCLRAPECNGGTWTQETCLPRVYEILP
SSAPLEGGTKLTLCGWDFGFSKNNRFELRNTVVHIGGQICALEAKSSNKNKLECTAP
AAKNASFNISSSVSVGHGKTLFNTFSYVNPIITSISPTYGPKSGGTLLTIAGKYLNS
GKSRRIFVGEKPCSLKSTSESSVECYTPAQRIPQEYRVRVGIDGAIRDAKGYFTYRE
DPVVLKIHPAKSFLSGGSTITAQGINLNSVCFPRMVITVPKLGMNFSVACSHRSSSE
IICCTTPSLKAFNLQPPFVTKVFFIFDGVSSLYFDFDYVNNPVFKHFEKPVLISRSN
PNVLEIKGNHIDSEAVKGEVLKVGNKSCENLLLQSETILCTVPSDLLKSNSELNIEW
KQEVLSTVIGKVLIRQDQNFTGLIAGVVSTSVLIYIFLVFFLWRRKKKQIKDLGSDL
VRYDGRVHTPHLDRLVSARSVSPTTEMVSSESVDYRSTFLEDQFPSMSQNGSCRPAQ
YPHSDLSPILSSGDSDLASPLLQTNVHIDISALNPDLVKEVQHVVIGADSLMVHFSE
VIGRGHFGCVSHGTLLDNDGRKIHCAVKSLNRITDLEEVAQFLKEGIIMKDFTHPNV
LSLLGICLPNEGSPLVVLPYMKHGDLRNFIRNETHNPTVKDLIGFGLQVAKGMKYLA
SKKFVHRDLAARNCMLDEKFTVKVADFGLARDVYDKEYYSVHNKTGAKLPVKWMALE
SLQTQKFTTKSDVWSFGVLLWELMTRGAPPYPDVNSFDITVYLLQGRRLLQPEYCPD
PLYEVMLKCWHPKPEMRPAFSELVSKISTIFSTFIGEHYVHVNATYVNVKCVAPYPS
LLSSQDNTDMDVDT

List of Sequences

```
SEQ ID NO: 4 (murine MET amino acid sequence):
MKAPTVLAPGILVLLLSLVQRSHGECKEALVKSEMNVNMKYQLPNFTAETPIQNVVL
HGHHIYLGATNYIYVLNDKDLQKVSEFKTGPVLEHPDCLPCRDCSSKANSSGGVWKD
NINMALLVDTYYDDQLISCGSVNRGTCQRHVLPPDNSADIQSEVHCMFSPEEESGQC
PDCVVSALGAKVLLSEKDRFINFFVGNTINSSYPPGYSLHSISVRRLKETQDGFKFL
TDQSYIDVLPEFQDSYPIKYIHAFESNHFIYFLTVQKETLDAQTFHTRIIRFCSVDS
GLHSYMEMPLECILTEKRRKRSTREEVFNILQAAYVSKPGANLAKQIGASPSDDILF
GVFAQSKPDSAEPVNRSAVCAFPIKYVNDFFNKIVNKNNVRCLQHFYGPNHEHCFNR
TLLRNSSGCEARSDEYRTEFTTALQRVDLFMGRLNQVLLTSISTFIKGDLTIANLGT
SEGRFMQVVLSRTAHLTPHVNFLLDSHPVSPEVIVEHPSNQNGYTLVVTGKKITKIP
LNGLGCGHFQSCSQCLSAPYFIQCGWCHNQCVRFDECPSGTWTQEICLPAVYKVFPT
SAPLEGGTVLTICGWDFGFRKNNKFDLRKTKVLLGNESCTLTLSESTTNTLKCTVGP
AMSEHFNVSVIISNSRETTQYSAFSYVDPVITSISPRYGPQAGGTLLTLTGKYLNSG
NSRHISIGGKTCTLKSVSDSILECYTPAQTTSDEFPVKLKIDLANRETSSFSYREDP
VVYEIHPTKSFISGGSTITGIGKTLNSVSLPKLVIDVHEVGVNYTVACQHRSNSEII
CCTTPSLKQLGLQLPLKTKAFFLLDGILSKHFDLTYVHNPVFEPFEKPVMISIGNEN
VVEIKGNNIDPEAVKGEVLKVGNQSCESLHWHSGAVLCTVPSDLLKLNSELNIEWKQ
AVSSTVLGKVIVQPDQNFAGLIIGAVSISVVVLLLSGLFLWMRKRKHKDLGSELVRY
DARVHTPHLDRLVSARSVSPTTEMVSNESVDYRATFPEDQFPNSSQNGACRQVQYPL
TDLSPILTSGDSDISSPLLQNTVHIDLSALNPELVQAVQHVVIGPSSLIVHFNEVIG
RGHFGCVYHGTLLDNDGKKIHCAVKSLNRITDIEEVSQFLTEGIIMKDFSHPNVLSL
LGICLRSEGSPLVVLPYMKHGDLRNFIRNETHNPTVKDLIGFGLQVAKGMKYLASKK
FVHRDLAARNCMLDEKFTVKVADFGLARDMYDKEYYSVHNKTGAKLPVKWMALESLQ
TQKFTTKSDVWSFGVLLWELMTRGAPPYPDVNTFDIIIYLLQGRRLLQPEYCPDALY
EVMLKCWHPKAEMRPSFSELVSRISSIFSTFIGEHYVHVNATYVNVKCVAPYPSLLP
SQDNIDGEGNT SEQ ID NO: 5 (chimeric 9006 heavy chain variable domain nucleic acid sequence):
CAGATCCATTTGGGGCAGTCTGGACCTGAGCTGAAGAAGCCTGGAGAGACAGTCAAG
ATCTCCTGCAAGGCTTCTGGGTATACCTTCACAAACTTTAGAATGAACTGGGTGAAG
CAGGCTCCAGGAAAGGGTTTAAAGTGGATGGGCTGGATAAACACCTACACTGGAGAG
CCAACATATGTTGATGACTTGAAGGGACGGTTTGCCTTCTCTTTGGAAACCTCTGCC
AGCACTGCCTATTTGCAGATCAACAACCTCAAAAATGAGGACATGGCTACATATTTC
TGTGCAAGGAAAGGGATTGCGAGGGCTATGGACTACTGGGGTCAAGGAACCTCAGTC
ACCGTCTCGAGT SEQ ID NO: 6 (chimeric 9006 heavy chain variable domain amino acid sequence):
QIHLGQSGPELKKPGETVKISCKASGYTFTNFRMNWVKQAPGKGLKWMGWINTYTGE
PTYVDDLKGRFAFSLETSASTAYLQINNLKNEDMATYFCARKGIARAMDYWGQGTSV
TVSS SEQ ID NO: 7 (chimeric 9006 light chain variable domain nucleic acid sequence):
AACATTGTGATGACACAGTCTCCATCCTCCCTGAGTGTGTCAGCAGGAGAGATGGTC
ACTATGAGTTGTAAGTCCAGTCAGAGTCTGTTAGACAGTGGAAATCAAAAGAACTAC
TTGGCCTGGTACCAGCAGAAACCAGGGCAGCCTCCTCAACTTTTGATCTTCGGGGCA
TCCACTAGGGAATCTGGGGTCCCTGATCGCTTCACAGGCAGTGGATCTGGAACCGAT
TTCACTCTTACCGTCAGCAGTGTGCAGGCTGAAGACCTGGCAGTTTATTACTGTCAG
AATGATCATAGTTATCCGTACACGTTCGGAGGGGGGACCAAGCTGGAAATAAAA SEQ ID NO: 8 (chimeric 9006 light chain variable domain amino acid sequence):
NIVMTQSPSSLSVSAGEMVTMSCKSSQSLLDSGNQKNYLAWYQQKPGQPPQLLIFGA
STRESGVPDRFTGSGSGTDFTLTVSSVQAEDLAVYYCQNDHSYPYTFGGGTKLEIK SEQ ID NO: 9 (chimeric 9338 heavy chain variable domain nucleic acid sequence):
CAGGTCCAACTGCAACAGCCTGGGGCTGAACTGGCAAAACCTGGGGCCTCAGTGAGG
ATGTCCTGCAAGGCTTCTGGCTACACCTTTACTAGTTACTGGATGCACTGGGTAAAA
CAGAGGCCTGGACAGGGTCTGGAATGGATTGGATACATTAATCCTAGCAGTGGTCAT
ATTGAGAACAATCAGAAGTTCAAGGACAAGGCCACATTGACTGCAGACAAATCCTCC
AGCACAGCCTACATGCAACTGAGCAGCCTGACATTTGAGGACTCTGCAGTCTATTAC
TGTGCAAGAGGACGGTTTGCTTACTGGGGCCAAGGGACTCTGGTCACTGTCTCGAGT SEQ ID NO: 10 (chimeric 9338 heavy chain variable domain amino acid sequence):
QVQLQQPGAELAKPGASVRMSCKASGYTFTSYWMHWVKQRPGQGLEWIGYINPSSGH
IENNQKFKDKATLTADKSSSTAYMQLSSLTFEDSAVYYCARGRFAYWGQGTLVTVSS SEQ ID NO: 11 (chimeric 9338 light chain variable domain nucleic acid sequence):
GATATTGTGATGACCCAGTCTCCAGCAATCATGTCTGCATCTCCTGGGGAGAAGGTC
ACCTTGACCTGCAGTGCCAGCTCAAGTGTAAGTTCCGGCTACTTGTACTGGTACCAG
CAGAAGCCAGGATCCTCCCCCAAACTCTGGATTTATAGCACATCCAACCTGGCTTCT
GGAGTCCCTGCTCGCTTCAGTGGCAGTGGGTCTGGGACCTCTTACTCTCTCACAGTC
AACAGCATGGAGGCTGAAGATGCTGCCTCTTATTTCTGCCATCAGTGGAGTAGTTAC
CCATTCACGTTCGGCTCGGGGACCAAGCTGGAGCTGAAA SEQ ID NO: 12 (chimeric 9338 light chain variable domain amino acid sequence):
DIVMTQSPAIMSASPGEKVTLTCSASSSVSSGYLYWYQQKPGSSPKLWIYSTSNLAS
GVPARFSGSGSGTSYSLTVNSMEAEDAASYFCHQWSSYPFTFGSGTKLELK
```

List of Sequences

SEQ ID NO: 13 (humanized 9006 heavy chain variable domain nucleic acid sequence):
CAGGTGCAGCTGGTGCAGTCTGGATCCGAGCTGAAGAAACCTGGCGCCTCCGTGAAG
GTGTCCTGCAAGGCTTCCGGCTACACCTTTACCAACTTCCGGATGAACTGGGTCAAG
CAGGCCCCAGGCCAGGGCCTGAAATGGATGGGCTGGATCAACACCTACACCGGCGAG
CCCACCTACGTGGACGACCTGAAGGGCAGATTCGTGTTCTCCCTGGACACCTCCGTG
TCCACCGCCTACCTGCAGATCTCCAGCCTGAAGGCCGAGGATACCGCCGTGTACTAC
TGCGCCCGGAAGGGAATCGCCAGAGCCATGGATTATTGGGGCCAGGGCACCACCGTG
ACAGTCTCGAGT SEQ ID NO: 14 (humanized 9006 heavy chain variable domain amino acid sequence):
QVQLVQSGSELKKPGASVKVSCKASGYTFTNFRMNWVKQAPGQGLKWMGWINTYTGE
PTYVDDLKGRFVFSLDTSVSTAYLQISSLKAEDTAVYYCARKGIARAMDYWGQGTTV
TVSS SEQ ID NO: 15 (humanized 9006 light chain variable domain nucleic acid sequence):
GACATCGTGATGACCCAGTCCCCCGACTCTCTGGCCGTGTCTCTGGGCGAGAGAGCC
ACCATCAACTGCAAGTCCTCCCAGTCCCTGCTGGACTCCGGCAACCAGAAGAACTAC
CTGGCCTGGTATCAGCAGAAGCCCGGCCAGCCTCCCAAGCTGCTGATCTTTGGCGCC
TCCACCCGGGAATCTGGCGTGCCCGATAGATTCTCCGGCTCTGGCACCGAC
TTTACCCTGACCATCAGCTCCCTGCAGGCCGAGGATGTGGCCGTGTACTACTGCCAG
AACGACCACTCCTACCCCTACACCTTCGGCCAGGGCACCAAGCTGGAAATCAAG SEQ ID NO: 16 (humanized 9006 light chain variable domain amino acid sequence):
DIVMTQSPDSLAVSLGERATINCKSSQSLLDSGNQKNYLAWYQQKPGQPPKLLIFGA
STRESGVPDRFSGSGSGTDFTLTISSLQAEDVAVYYCQNDHSYPYTFGQGTKLEIK SEQ ID NO: 17 (humanized 9338 heavy chain variable domain nucleic acid sequence):
CAGGTGCAGCTGGTGCAGTCTGGCGCTGAAGTGAAGAAACCCGGCTCCTCCGTGAAG
GTGTCCTGCAAGGCCTCCGGCTACACCTTTACCAGCTACTGGATGCACTGGGTGCGA
CAGGCCCCTGGACAGGGCCTGGAATGGATGGGCTACATCAACCCCTCCAGCGGCCAC
ATCGAGAACAACCAGAAATTCAAGGACCGCGTGACCATCACCGCCGACAAGTCCACC
TCCACCGCCTACATGGAACTGTCCTCCCTGCGGAGCGAGGACACCGCCGTGTACTAC
TGTGCCAGAGGCAGATTCGCCTACTGGGGCCAGGGCACCCTCGTGACAGTCTCGAGT SEQ ID NO: 18 (humanized 9338 heavy chain variable domain amino acid sequence):
QVQLVQSGAEVKKPGSSVKVSCKASGYTFTSYWMHWVRQAPGQGLEWMGYINPSSGH
IENNQKFKDRVTITADKSTSTAYMELSSLRSEDTAVYYCARGRFAYWGQGTLVTVSS SEQ ID NO: 19 (humanized 9338 light chain variable domain nucleic acid sequence):
GAGATCGTGCTGACCCAGTCTCCTGCCACCCTGTCTCTGAGCCCTGGCGAGAGAGCT
ACCCTGTCCTGCTCCGCCTCCTCCTCTGTGTCCTCCGGCTACCTGTACTGGTATCAG
CAGAAGCCCGGCCAGGCCCCTCGGCTGCTGATCTACTCTACCTCCAACCTGGCCTCC
GGCATCCCTGCCAGATTCTCCGGCTCTGGCTCTGGCACCGACTTTACCCTGACCATC
TCCAGCCTGGAACCCGAGGACTTCGCCGTGTACTACTGCCACCAGTGGTCCAGCTAC
CCCTTCACCTTTGGCTCCGGCACCAAGCTGGAAATCAAG SEQ ID NO: 20 (humanized 9338 light chain variable domain amino acid sequence):
EIVLTQSPATLSLSPGERATLSCSASSSVSSGYLYWYQQKPGQAPRLLIYSTSNLAS
GIPARFSGSGSGTDFTLTISSLEPEDFAVYYCHQWSSYPFTFGSGTKLEIK SEQ ID NO: 21 (9006 heavy chain CDR1 amino acid sequence):
GYTFTNFR SEQ ID NO: 22 (9006 heavy chain CDR2 amino acid sequence):
INTYTGEP SEQ ID NO: 23 (9006 heavy chain CDR3 amino acid sequence):
ARKGIARAMDY SEQ ID NO: 24 (9006 light chain CDR1 amino acid sequence):
QSLLDSGNQKNY SEQ ID NO: 25 (9006 light chain CDR2 amino acid sequence):
GAS SEQ ID NO: 26 (9006 light chain CDR3 amino acid sequence):
QNDHSYPYT SEQ ID NO: 27 (9338 heavy chain CDR1 amino acid sequence):
GYTFTSYW SEQ ID NO: 28 (9338 heavy chain CDR2 amino acid sequence):
INPSSGHI SEQ ID NO: 29 (9338 heavy chain CDR3 amino acid sequence):
ARGRFAY -continued

List of Sequences

SEQ ID NO: 30 (9338 light chain CDR1 amino acid sequence):
SSVSSGY

SEQ ID NO: 31(9338 light chain CDR2 amino acid sequence):
STS

SEQ ID NO: 32 (9338 light chain CDR3 amino acid sequence):
HQWSSYPFT

SEQ ID NO: 33 (humanized 9006 light chain amino acid sequence):
DIVMTQSPDSLAVSLGERATINCKSSQSLLDSGNQKNYLAWYQQKPGQPPKLLIFGA
STRESGVPDRFSGSGSGTDFTLTISSLQAEDVAVYYCQNDHSYPYTFGQGTKLEIKR
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC SEQ ID NO: 34 (humanized 9006 heavy chain amino acid sequence):
QVQLVQSGSELKKPGASVKVSCKASGYTFTNFRMNWVKQAPGQGLKWMGWINTYTGE
PTYVDDLKGRFVFSLDTSVSTAYLQISSLKAEDTAVYYCARKGIARAMDYWGQGTTV
TVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKRVEPKSCDKTHTCP
PCPAPELLGGPSVFLFPPKPKDTLMISRTPEVICVVVDVSHEDPEVKFNWYVDGVEV
HNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPG SEQ ID NO: 35 (humanized 9338 light chain amino acid sequence):
EIVLTQSPATLSLSPGERATLSCSASSSVSSGYLYWYQQKPGQAPRLLIYSTSNLAS
GIPARFSGSGSGTDFTLTISSLEPEDFAVYYCHQWSSYPFTFGSGTKLEIKRTVAAP
SVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC SEQ ID NO: 36 (humanized 9338 heavy chain amino acid sequence):
QVQLVQSGAEVKKPGSSVKVSCKASGYTFTSYWMHWVRQAPGQGLEWMGYINPSSGH
IENNQKFKDRVTITADKSTSTAYMELSSLRSEDTAVYYCARGRFAYWGQGTLVTVSS
ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDG
SFFLYSKLTVDKSRWQQGNVFSCSVMHEALHNHYTQKSLSLSPG

The invention claimed is:

1. An antibody composition comprising a first anti-MET antibody or an antigen-binding portion thereof and a second anti-MET antibody or an antigen-binding portion thereof, wherein:
   a) said first anti-MET antibody or antigen-binding portion thereof has heavy chain (H)-CDR1-3 and light chain (L)-CDR1-3 comprising the amino acid sequences of SEQ ID NOs: 21, 22, 23, 24, 25, and 26, respectively; and
   b) said second anti-MET antibody or antigen-binding portion thereof has H-CDR1-3 and L-CDR1-3 comprising the amino acid sequences of SEQ ID NOs: 27, 28, 29, 30, 31, and 32, respectively.

2. The antibody composition of claim 1, wherein said first anti-MET antibody has a heavy chain variable domain (VH) and a light chain variable domain (VL) that comprise the amino acid sequences of SEQ ID NOs: 6 and 8, respectively, and said second anti-MET antibody has a VH and a VL that comprise the amino acid sequences of SEQ ID NOs: 10 and 12, respectively.

3. An antibody composition comprising a first anti-MET antibody and a second anti-MET antibody, wherein:
   said first anti-MET antibody has a heavy chain (HC) and a light chain (LC) that comprise the amino acid sequences of SEQ ID NOs: 34 and 33, respectively, and
   said second anti-MET antibody has an HC and an LC that comprise the amino acid sequences of SEQ ID NO: 36 and 35, respectively.

4. The antibody composition of claim 1, wherein said composition has at least one property selected from the group consisting of:
   a) induces degradation of MET;
   b) inhibits growth in vitro of at least one cell line selected from SNU5, EBC1, MKN45, KatoII, OE33, and Okajima;
   c) inhibits MET phosphorylation;
   d) inhibits MET downstream signaling;
   e) inhibits primary endothelial cell proliferation in the presence or absence of HGF; and
   f) inhibits tumor growth in vivo.

5. The antibody composition of claim 1, further comprising a pharmaceutically acceptable excipient.

6. An anti-MET antibody or an antigen-binding portion thereof, wherein said antibody or antigen-binding portion thereof has heavy chain (H)-CDR1-3 and light chain (L)-CDR1-3 that comprise the amino acid sequences of SEQ ID NOs: 21, 22, 23, 24, 25, and 26, respectively.

7. The anti-MET antibody of claim 6, wherein said antibody comprises a heavy chain (HC) comprising the amino acid sequence of SEQ ID NO: 34 and a light chain (LC) comprising the amino acid sequence of SEQ ID NO: 33.

8. The anti-MET antibody or antigen-binding portion of claim 6, wherein said antibody has at least one property selected from the group consisting of:
   a) does not bind to mouse or chicken MET;
   b) binds to an epitope of human MET comprising residues that are present on the SEMA domain;
   c) induces degradation of MET;
   d) binds to human MET with a $K_D$ of $1 \times 10^{-9}$ M or less;
   e) inhibits growth in vitro of at least one cell line selected from SNU5, EBC1, MKN45, KatoII, OE33, and Okajima;
   f) inhibits MET phosphorylation;
   g) inhibits MET downstream signaling;
   h) inhibits primary endothelial cell proliferation in the presence or absence of HGF; and
   i) inhibits tumor growth in vivo.

9. A pharmaceutical composition comprising the anti-MET antibody or antigen-binding portion of claim 6 and a pharmaceutically acceptable excipient.

10. A bispecific binding molecule having an antigen-binding domain of a first anti-MET antibody and an antigen-binding domain of a second anti-M ET antibody, wherein:
    a) said antigen-binding domain of the first anti-MET antibody has heavy chain (H)-CDR1-3 and light chain (L)-CDR1-3 comprising the amino acid sequences of SEQ ID NOs: 21, 22, 23, 24, 25, and 26, respectively; and
    b) said antigen-binding domain of the second anti-MET antibody has H-CDR1-3 and L-CDR1-3 comprising the amino acid sequences of SEQ ID NOs: 27, 28, 29, 30, 31, and 32, respectively.

11. The anti-MET antibody or antigen-binding portion of claim 6, wherein said antibody has a heavy chain variable domain (VH) comprising the amino acid sequence of SEQ ID NO: 6 and a light chain variable domain (VL) comprising the amino acid sequence of SEQ ID NO: 8.

12. The anti-MET antibody or antigen-binding portion of claim 6, wherein said antibody has a heavy chain variable domain (VH) comprising the amino acid sequence of SEQ ID NO: 14 and a light chain variable domain (VL) comprising the amino acid sequence of SEQ ID NO: 16.

13. An anti-MET antibody or an antigen-binding portion thereof, wherein said antibody or antigen-binding portion thereof has heavy chain (H)-CDR1-3 and light chain (L)-CDR1-3 that comprise the amino acid sequences of SEQ ID NOs: 27, 28, 29, 30, 31, and 32, respectively.

14. The anti-MET antibody or antigen-binding portion of claim 13, wherein said antibody has a heavy chain variable domain (VH) comprising the amino acid sequence of SEQ ID NO: 10 and a light chain variable domain (VL) comprising the amino acid sequence of SEQ ID NO: 12.

15. The anti-MET antibody or antigen-binding portion of claim 13, wherein said antibody has a heavy chain variable domain (VH) comprising the amino acid sequence of SEQ ID NO: 18 and a light chain variable domain (VL) comprising the amino acid sequence of SEQ ID NO: 20.

16. The anti-MET antibody of claim 13, wherein said antibody comprises a heavy chain (HC) comprising the amino acid sequence of SEQ ID NO: 36 and a light chain (LC) comprising the amino acid sequence of SEQ ID NO: 35.

17. The anti-MET antibody or antigen-binding portion of claim 13, wherein said antibody has at least one property selected from the group consisting of:
  a) does not bind to mouse or chicken MET;
  b) binds to an epitope of human MET comprising residues that are present on the SEMA domain;
  c) induces degradation of MET;
  d) binds to human MET with a $K_D$ of $1\times10^{-9}$M or less;
  e) inhibits growth in vitro of at least one cell line selected from SNU5, EBC1, MKN45, KatoII, OE33, and Okajima;
  f) inhibits MET phosphorylation;
  g) inhibits MET downstream signaling;
  h) inhibits primary endothelial cell proliferation in the presence or absence of HGF; and
  i) inhibits tumor growth in vivo.

18. A pharmaceutical composition comprising the anti-MET antibody or antigen-binding portion of claim 13 and a pharmaceutically acceptable excipient.

19. The antibody composition of claim 1, wherein said first anti-MET antibody has a heavy chain variable domain (VH) and a light chain variable domain (VL) that comprise the amino acid sequences of SEQ ID NOs: 14 and 16, respectively, and said second anti-MET antibody has a VH and a VL that comprise the amino acid sequences of SEQ ID NOs: 18 and 20, respectively.

20. A method for treating a patient with a MET-expressing cancer, comprising administering to said patient the antibody composition of claim 1.

21. A method for treating a patient with a MET-expressing cancer, comprising administering to said patient the anti-MET antibody or antigen-binding portion of claim 6.

22. A method for treating a patient with a MET-expressing cancer, comprising administering to said patient the bispecific binding molecule of claim 10.

23. A method for treating a patient with a MET-expressing cancer, comprising administering to said patient the anti-MET antibody or antigen-binding portion of claim 13.

* * * * *

SEQUENCE LISTING

```
<160> NUMBER OF SEQ ID NOS: 39

<210> SEQ ID NO 1
<211> LENGTH: 1390
<212> TYPE: PRT
<213> ORGANISM: Homo sapiens

<400> SEQUENCE: 1
```

| Met | Lys | Ala | Pro | Ala | Val | Leu | Ala | Pro | Gly | Ile | Leu | Val | Leu | Leu | Phe |
|---|---|---|---|---|---|---|---|---|---|---|---|---|---|---|---|
| 1 | | | | 5 | | | | | 10 | | | | | 15 | |

| Thr | Leu | Val | Gln | Arg | Ser | Asn | Gly | Glu | Cys | Lys | Glu | Ala | Leu | Ala | Lys |
|---|---|---|---|---|---|---|---|---|---|---|---|---|---|---|---|
| | | | 20 | | | | | 25 | | | | | 30 | | |

| Ser | Glu | Met | Asn | Val | Asn | Met | Lys | Tyr | Gln | Leu | Pro | Asn | Phe | Thr | Ala |
|---|---|---|---|---|---|---|---|---|---|---|---|---|---|---|---|
| | | | 35 | | | | 40 | | | | | 45 | | | |

| Glu | Thr | Pro | Ile | Gln | Asn | Val | Ile | Leu | His | Glu | His | His | Ile | Phe | Leu |
|---|---|---|---|---|---|---|---|---|---|---|---|---|---|---|---|
| | 50 | | | | | 55 | | | | | 60 | | | | |

| Gly | Ala | Thr | Asn | Tyr | Ile | Tyr | Val | Leu | Asn | Glu | Glu | Asp | Leu | Gln | Lys |
|---|---|---|---|---|---|---|---|---|---|---|---|---|---|---|---|
| 65 | | | | | 70 | | | | | 75 | | | | | 80 |

| Val | Ala | Glu | Tyr | Lys | Thr | Gly | Pro | Val | Leu | Glu | His | Pro | Asp | Cys | Phe |
|---|---|---|---|---|---|---|---|---|---|---|---|---|---|---|---|
| | | | | 85 | | | | | 90 | | | | | 95 | |

| Pro | Cys | Gln | Asp | Cys | Ser | Ser | Lys | Ala | Asn | Leu | Ser | Gly | Gly | Val | Trp |
|---|---|---|---|---|---|---|---|---|---|---|---|---|---|---|---|
| | | | 100 | | | | | 105 | | | | | 110 | | |

```
Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
        130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525
```

```
Cys Leu Ser Ala Pro Pro Phe Val Gln Cys Gly Trp Cys His Asp Lys
    530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
                580                 585                 590
Asn Asn Lys Phe Asp Leu Lys Lys Thr Arg Val Leu Leu Gly Asn Glu
            595                 600                 605
Ser Cys Thr Leu Thr Leu Ser Glu Ser Thr Met Asn Thr Leu Lys Cys
    610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
                660                 665                 670
Thr Leu Leu Thr Leu Thr Gly Asn Tyr Leu Asn Ser Gly Asn Ser Arg
            675                 680                 685
His Ile Ser Ile Gly Gly Lys Thr Cys Thr Leu Lys Ser Val Ser Asn
    690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
            740                 745                 750
Phe Ile Ser Gly Gly Ser Thr Ile Thr Gly Val Gly Lys Asn Leu Asn
    755                 760                 765
Ser Val Ser Val Pro Arg Met Val Ile Asn Val His Glu Ala Gly Arg
770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
            820                 825                 830
Leu Ile Tyr Val His Asn Pro Val Phe Lys Pro Phe Glu Lys Pro Val
    835                 840                 845
Met Ile Ser Met Gly Asn Glu Asn Val Leu Glu Ile Lys Gly Asn Asp
850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
            900                 905                 910
Gln Ala Ile Ser Ser Thr Val Leu Gly Lys Val Ile Val Gln Pro Asp
    915                 920                 925
Gln Asn Phe Thr Gly Leu Ile Ala Gly Val Val Ser Ile Ser Thr Ala
930                 935                 940
Leu Leu Leu Leu Leu Gly Phe Phe Leu Trp Leu Lys Lys Arg Lys Gln
```

-continued

```
945                 950                 955                 960
Ile Lys Asp Leu Gly Ser Glu Leu Val Arg Tyr Asp Ala Arg Val His
                    965                 970                 975
Thr Pro His Leu Asp Arg Leu Val Ser Ala Arg Ser Val Ser Pro Thr
                    980                 985                 990
Thr Glu Met Val Ser Asn Glu Ser Val Asp Tyr Arg Ala Thr Phe Pro
                    995                1000                1005
Glu Asp Gln Phe Pro Asn Ser Ser Gln Asn Gly Ser Cys Arg Gln
    1010                1015                1020
Val Gln Tyr Pro Leu Thr Asp Met Ser Pro Ile Leu Thr Ser Gly
    1025                1030                1035
Asp Ser Asp Ile Ser Ser Pro Leu Leu Gln Asn Thr Val His Ile
    1040                1045                1050
Asp Leu Ser Ala Leu Asn Pro Glu Leu Val Gln Ala Val Gln His
    1055                1060                1065
Val Val Ile Gly Pro Ser Ser Leu Ile Val His Phe Asn Glu Val
    1070                1075                1080
Ile Gly Arg Gly His Phe Gly Cys Val Tyr His Gly Thr Leu Leu
    1085                1090                1095
Asp Asn Asp Gly Lys Lys Ile His Cys Ala Val Lys Ser Leu Asn
    1100                1105                1110
Arg Ile Thr Asp Ile Gly Glu Val Ser Gln Phe Leu Thr Glu Gly
    1115                1120                1125
Ile Ile Met Lys Asp Phe Ser His Pro Asn Val Leu Ser Leu Leu
    1130                1135                1140
Gly Ile Cys Leu Arg Ser Glu Gly Ser Pro Leu Val Val Leu Pro
    1145                1150                1155
Tyr Met Lys His Gly Asp Leu Arg Asn Phe Ile Arg Asn Glu Thr
    1160                1165                1170
His Asn Pro Thr Val Lys Asp Leu Ile Gly Phe Gly Leu Gln Val
    1175                1180                1185
Ala Lys Gly Met Lys Tyr Leu Ala Ser Lys Lys Phe Val His Arg
    1190                1195                1200
Asp Leu Ala Ala Arg Asn Cys Met Leu Asp Glu Lys Phe Thr Val
    1205                1210                1215
Lys Val Ala Asp Phe Gly Leu Ala Arg Asp Met Tyr Asp Lys Glu
    1220                1225                1230
Tyr Tyr Ser Val His Asn Lys Thr Gly Ala Lys Leu Pro Val Lys
    1235                1240                1245
Trp Met Ala Leu Glu Ser Leu Gln Thr Gln Lys Phe Thr Thr Lys
    1250                1255                1260
Ser Asp Val Trp Ser Phe Gly Val Leu Leu Trp Glu Leu Met Thr
    1265                1270                1275
Arg Gly Ala Pro Pro Tyr Pro Asp Val Asn Thr Phe Asp Ile Thr
    1280                1285                1290
Val Tyr Leu Leu Gln Gly Arg Arg Leu Leu Gln Pro Glu Tyr Cys
    1295                1300                1305
Pro Asp Pro Leu Tyr Glu Val Met Leu Lys Cys Trp His Pro Lys
    1310                1315                1320
Ala Glu Met Arg Pro Ser Phe Ser Glu Leu Val Ser Arg Ile Ser
    1325                1330                1335
Ala Ile Phe Ser Thr Phe Ile Gly Glu His Tyr Val His Val Asn
    1340                1345                1350
```

-continued

```
Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
1370                1375                1380

Ala Ser Phe Trp Glu Thr Ser
    1385                1390

<210> SEQ ID NO 2
<211> LENGTH: 1408
<212> TYPE: PRT
<213> ORGANISM: Homo sapiens

<400> SEQUENCE: 2

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
```

-continued

```
                325                 330                 335
Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
        370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750
```

```
Phe Ile Ser Thr Trp Trp Lys Glu Pro Leu Asn Ile Val Ser Phe Leu
        755                 760                 765

Phe Cys Phe Ala Ser Gly Gly Ser Thr Ile Thr Gly Val Gly Lys Asn
        770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
                805                 810                 815

Ile Cys Cys Thr Thr Pro Ser Leu Gln Gln Leu Asn Leu Gln Leu Pro
                820                 825                 830

Leu Lys Thr Lys Ala Phe Phe Met Leu Asp Gly Ile Leu Ser Lys Tyr
                835                 840                 845

Phe Asp Leu Ile Tyr Val His Asn Pro Val Phe Lys Pro Phe Glu Lys
        850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
                900                 905                 910

Thr Val Pro Asn Asp Leu Leu Lys Leu Asn Ser Glu Leu Asn Ile Glu
                915                 920                 925

Trp Lys Gln Ala Ile Ser Ser Thr Val Leu Gly Lys Val Ile Val Gln
        930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
                965                 970                 975

Lys Gln Ile Lys Asp Leu Gly Ser Glu Leu Val Arg Tyr Asp Ala Arg
                980                 985                 990

Val His Thr Pro His Leu Asp Arg Leu Val Ser Ala Arg Ser Val Ser
        995                 1000                1005

Pro Thr Thr Glu Met Val Ser Asn Glu Ser Val Asp Tyr Arg Ala
    1010                1015                1020

Thr Phe Pro Glu Asp Gln Phe Pro Asn Ser Ser Gln Asn Gly Ser
    1025                1030                1035

Cys Arg Gln Val Gln Tyr Pro Leu Thr Asp Met Ser Pro Ile Leu
    1040                1045                1050

Thr Ser Gly Asp Ser Asp Ile Ser Ser Pro Leu Leu Gln Asn Thr
    1055                1060                1065

Val His Ile Asp Leu Ser Ala Leu Asn Pro Glu Leu Val Gln Ala
    1070                1075                1080

Val Gln His Val Val Ile Gly Pro Ser Ser Leu Ile Val His Phe
    1085                1090                1095

Asn Glu Val Ile Gly Arg Gly His Phe Gly Cys Val Tyr His Gly
    1100                1105                1110

Thr Leu Leu Asp Asn Asp Gly Lys Lys Ile His Cys Ala Val Lys
    1115                1120                1125

Ser Leu Asn Arg Ile Thr Asp Ile Gly Glu Val Ser Gln Phe Leu
    1130                1135                1140

Thr Glu Gly Ile Ile Met Lys Asp Phe Ser His Pro Asn Val Leu
    1145                1150                1155
```

-continued

```
Ser Leu Leu Gly Ile Cys Leu Arg Ser Glu Gly Ser Pro Leu Val
    1160            1165                1170

Val Leu Pro Tyr Met Lys His Gly Asp Leu Arg Asn Phe Ile Arg
    1175            1180                1185

Asn Glu Thr His Asn Pro Val Lys Asp Leu Ile Gly Phe Gly
    1190            1195                1200

Leu Gln Val Ala Lys Gly Met Lys Tyr Leu Ala Ser Lys Lys Phe
    1205            1210                1215

Val His Arg Asp Leu Ala Ala Arg Asn Cys Met Leu Asp Glu Lys
    1220            1225                1230

Phe Thr Val Lys Val Ala Asp Phe Gly Leu Ala Arg Asp Met Tyr
    1235            1240                1245

Asp Lys Glu Tyr Tyr Ser Val His Asn Lys Thr Gly Ala Lys Leu
    1250            1255                1260

Pro Val Lys Trp Met Ala Leu Glu Ser Leu Gln Thr Gln Lys Phe
    1265            1270                1275

Thr Thr Lys Ser Asp Val Trp Ser Phe Gly Val Leu Leu Trp Glu
    1280            1285                1290

Leu Met Thr Arg Gly Ala Pro Pro Tyr Pro Asp Val Asn Thr Phe
    1295            1300                1305

Asp Ile Thr Val Tyr Leu Leu Gln Gly Arg Arg Leu Leu Gln Pro
    1310            1315                1320

Glu Tyr Cys Pro Asp Pro Leu Tyr Glu Val Met Leu Lys Cys Trp
    1325            1330                1335

His Pro Lys Ala Glu Met Arg Pro Ser Phe Ser Glu Leu Val Ser
    1340            1345                1350

Arg Ile Ser Ala Ile Phe Ser Thr Phe Ile Gly Glu His Tyr Val
    1355            1360                1365

His Val Asn Ala Thr Tyr Val Asn Val Lys Cys Val Ala Pro Tyr
    1370            1375                1380

Pro Ser Leu Leu Ser Ser Glu Asp Asn Ala Asp Glu Val Asp
    1385            1390                1395

Thr Arg Pro Ala Ser Phe Trp Glu Thr Ser
    1400            1405
```

<210> SEQ ID NO 3
<211> LENGTH: 1382
<212> TYPE: PRT
<213> ORGANISM: Gallus gallus

<400> SEQUENCE: 3

```
Met Lys Pro Val Thr Ala Tyr Pro Ser Gly Ile Ile Leu Phe Leu Phe
1               5                   10                  15

Ala Leu Leu Gln Arg Ser His Gly Gln Cys Lys Glu Ala Ala Lys Lys
                20                  25                  30

Ser Glu Met Asn Leu Asn Val Lys Tyr Asp Leu Pro Asn Phe Ile Thr
            35                  40                  45

Glu Thr Pro Ile Gln Asn Val Val Leu Tyr Lys His His Val Tyr Ile
        50                  55                  60

Gly Ala Val Asn Lys Ile Tyr Val Leu Asn Glu Thr Leu Gln Asn Ile
65                  70                  75                  80

Ser Val Tyr Lys Thr Gly Pro Ile Leu Glu Ser Pro Gly Cys Ala Pro
                85                  90                  95

Cys Glu Asp Cys Lys Asp Lys Ala Asn Leu Ser Asn Ser Val Trp Lys
            100                 105                 110
```

```
Asp Asn Val Asn Met Ala Leu Leu Glu Thr Tyr Tyr Asp Asp Gln
        115                 120                 125

Leu Ile Ser Cys Gly Ser Val Ser Gly Gly Val Cys His Arg His Ile
    130                 135                 140

Ile Pro Pro Asp Asn Pro Ala Asp Ile Glu Ser Glu Val His Cys Met
145                 150                 155                 160

Tyr Ser Pro Gln Val Asp Gly Glu Ala Asp Asn Cys Pro Asp Cys Val
                165                 170                 175

Val Ser Thr Leu Gly Thr Lys Val Leu Val Thr Glu Lys Asp Arg Phe
                180                 185                 190

Val Asn Phe Phe Val Gly Asn Thr Met Thr Ser Ala Phe Gln Pro Pro
            195                 200                 205

His Val Leu His Ser Ile Ser Val Arg Arg Leu Lys Glu Thr Gln Asp
        210                 215                 220

Gly Phe Glu Phe Leu Thr Asp Gln Ser Tyr Ile Asp Ile Leu Pro Gln
225                 230                 235                 240

Phe Arg Asp Ser Tyr Pro Ile Lys Tyr Val His Ala Phe Glu His Asp
                245                 250                 255

His Phe Val Tyr Phe Leu Thr Val Gln Arg Glu Ser Leu Asp Ser Gln
                260                 265                 270

Thr Phe His Thr Arg Ile Ile Arg Phe Cys Thr Leu Asp Ser Glu Met
            275                 280                 285

Arg Ser Tyr Met Glu Met Pro Leu Glu Cys Ile Phe Thr Glu Lys Arg
        290                 295                 300

Arg Lys Arg Ser Ile Arg Lys Glu Val Phe Asn Ile Leu Gln Ala Ala
305                 310                 315                 320

Tyr Val Ser Lys Pro Gly Ala Ala Leu Ala His Glu Met Gly Leu Gly
                325                 330                 335

Leu Ile Asp Asp Ile Leu Tyr Gly Val Phe Ala Gln Thr Asn Gln Ile
                340                 345                 350

Pro Gln Glu Pro Thr Asn Arg Ser Ala Val Cys Ala Val Ser Val Arg
        355                 360                 365

Thr Ile Asn Glu Phe Phe Asn Lys Ile Val Asp Lys Gln Asn Met Lys
    370                 375                 380

Cys Leu Gln His Phe Tyr Gly Lys Asp Ser Lys Tyr Cys Leu Asn Arg
385                 390                 395                 400

Ala Phe Ser Arg Asn Ala Ser Tyr Cys Arg Ala Gln Asp Asp Glu Tyr
                405                 410                 415

Arg Leu Glu Val Thr Thr Pro Leu Gln Arg Val Asp Leu Phe Met Gly
                420                 425                 430

Gln Phe Asn Asn Ile Leu Leu Thr Ser Ile Ser Val Phe Thr Lys Gly
            435                 440                 445

Asn Leu Thr Ile Ala Asn Leu Gly Thr Ser Glu Gly Arg Phe Met Gln
    450                 455                 460

Ile Val Val Ser Arg Ser Glu Pro Thr Ala Pro His Val Ser Phe Gln
465                 470                 475                 480

Leu Asp Ser His Ala Val Ser Pro Gln Val Val Glu Gln Ser Ala
                485                 490                 495

Ala Ala Asp Gly Tyr Thr Leu Val Val Thr Gly Lys Lys Ile Thr Lys
                500                 505                 510

Val Pro Leu Asn Gly Pro Gly Cys His His Phe Gln Ser Cys Ser Gln
                515                 520                 525
```

```
Cys Leu Leu Ala Pro Ala Phe Met Arg Cys Gly Trp Cys Gly Gln Gln
    530                 535                 540

Cys Leu Arg Ala Pro Glu Cys Asn Gly Gly Thr Trp Thr Gln Glu Thr
545                 550                 555                 560

Cys Leu Pro Arg Val Tyr Glu Ile Leu Pro Ser Ser Ala Pro Leu Glu
                565                 570                 575

Gly Gly Thr Lys Leu Thr Leu Cys Gly Trp Asp Phe Gly Phe Ser Lys
            580                 585                 590

Asn Asn Arg Phe Glu Leu Arg Asn Thr Val Val His Ile Gly Gly Gln
        595                 600                 605

Ile Cys Ala Leu Glu Ala Lys Ser Ser Asn Lys Asn Lys Leu Glu Cys
610                 615                 620

Thr Ala Pro Ala Ala Lys Asn Ala Ser Phe Asn Ile Ser Ser Ser Val
625                 630                 635                 640

Ser Val Gly His Gly Lys Thr Leu Phe Asn Thr Phe Ser Tyr Val Asn
                645                 650                 655

Pro Ile Ile Thr Ser Ile Ser Pro Thr Tyr Gly Pro Lys Ser Gly Gly
            660                 665                 670

Thr Leu Leu Thr Ile Ala Gly Lys Tyr Leu Asn Ser Gly Lys Ser Arg
        675                 680                 685

Arg Ile Phe Val Gly Glu Lys Pro Cys Ser Leu Lys Ser Thr Ser Glu
690                 695                 700

Ser Ser Val Glu Cys Tyr Thr Pro Ala Gln Arg Ile Pro Gln Glu Tyr
705                 710                 715                 720

Arg Val Arg Val Gly Ile Asp Gly Ala Ile Arg Asp Ala Lys Gly Tyr
                725                 730                 735

Phe Thr Tyr Arg Glu Asp Pro Val Val Leu Lys Ile His Pro Ala Lys
            740                 745                 750

Ser Phe Leu Ser Gly Gly Ser Thr Ile Thr Ala Gln Gly Ile Asn Leu
        755                 760                 765

Asn Ser Val Cys Phe Pro Arg Met Val Ile Thr Val Pro Lys Leu Gly
770                 775                 780

Met Asn Phe Ser Val Ala Cys Ser His Arg Ser Ser Ser Glu Ile Ile
785                 790                 795                 800

Cys Cys Thr Thr Pro Ser Leu Lys Ala Phe Asn Leu Gln Pro Pro Phe
                805                 810                 815

Val Thr Lys Val Phe Phe Ile Phe Asp Gly Val Ser Ser Leu Tyr Phe
            820                 825                 830

Asp Phe Asp Tyr Val Asn Asn Pro Val Phe Lys His Phe Glu Lys Pro
        835                 840                 845

Val Leu Ile Ser Arg Ser Asn Pro Asn Val Leu Glu Ile Lys Gly Asn
850                 855                 860

His Ile Asp Ser Glu Ala Val Lys Gly Glu Val Leu Lys Val Gly Asn
865                 870                 875                 880

Lys Ser Cys Glu Asn Leu Leu Leu Gln Ser Glu Thr Ile Leu Cys Thr
                885                 890                 895

Val Pro Ser Asp Leu Leu Lys Ser Asn Ser Glu Leu Asn Ile Glu Trp
            900                 905                 910

Lys Gln Glu Val Leu Ser Thr Val Ile Gly Lys Val Leu Ile Arg Gln
        915                 920                 925

Asp Gln Asn Phe Thr Gly Leu Ile Ala Gly Val Val Ser Thr Ser Val
930                 935                 940

Leu Ile Tyr Ile Phe Leu Val Phe Phe Leu Trp Arg Arg Lys Lys Lys
```

-continued

```
                945                 950                 955                 960
        Gln Ile Lys Asp Leu Gly Ser Asp Leu Val Arg Tyr Asp Gly Arg Val
                        965                 970                 975
        His Thr Pro His Leu Asp Arg Leu Val Ser Ala Arg Ser Val Ser Pro
                        980                 985                 990
        Thr Thr Glu Met Val Ser Ser Glu Ser Val Asp Tyr Arg Ser Thr Phe
                        995                 1000                1005
        Leu Glu Asp Gln Phe Pro Ser Met Ser Gln Asn Gly Ser Cys Arg
                1010                1015                1020
        Pro Ala Gln Tyr Pro His Ser Asp Leu Ser Pro Ile Leu Ser Ser
                1025                1030                1035
        Gly Asp Ser Asp Leu Ala Ser Pro Leu Leu Gln Thr Asn Val His
                1040                1045                1050
        Ile Asp Ile Ser Ala Leu Asn Pro Asp Leu Val Lys Glu Val Gln
                1055                1060                1065
        His Val Val Ile Gly Ala Asp Ser Leu Met Val His Phe Ser Glu
                1070                1075                1080
        Val Ile Gly Arg Gly His Phe Gly Cys Val Ser His Gly Thr Leu
                1085                1090                1095
        Leu Asp Asn Asp Gly Arg Lys Ile His Cys Ala Val Lys Ser Leu
                1100                1105                1110
        Asn Arg Ile Thr Asp Leu Glu Glu Val Ala Gln Phe Leu Lys Glu
                1115                1120                1125
        Gly Ile Ile Met Lys Asp Phe Thr His Pro Asn Val Leu Ser Leu
                1130                1135                1140
        Leu Gly Ile Cys Leu Pro Asn Glu Gly Ser Pro Leu Val Val Leu
                1145                1150                1155
        Pro Tyr Met Lys His Gly Asp Leu Arg Asn Phe Ile Arg Asn Glu
                1160                1165                1170
        Thr His Asn Pro Thr Val Lys Asp Leu Ile Gly Phe Gly Leu Gln
                1175                1180                1185
        Val Ala Lys Gly Met Lys Tyr Leu Ala Ser Lys Lys Phe Val His
                1190                1195                1200
        Arg Asp Leu Ala Ala Arg Asn Cys Met Leu Asp Glu Lys Phe Thr
                1205                1210                1215
        Val Lys Val Ala Asp Phe Gly Leu Ala Arg Asp Val Tyr Asp Lys
                1220                1225                1230
        Glu Tyr Tyr Ser Val His Asn Lys Thr Gly Ala Lys Leu Pro Val
                1235                1240                1245
        Lys Trp Met Ala Leu Glu Ser Leu Gln Thr Gln Lys Phe Thr Thr
                1250                1255                1260
        Lys Ser Asp Val Trp Ser Phe Gly Val Leu Leu Trp Glu Leu Met
                1265                1270                1275
        Thr Arg Gly Ala Pro Pro Tyr Pro Asp Val Asn Ser Phe Asp Ile
                1280                1285                1290
        Thr Val Tyr Leu Leu Gln Gly Arg Arg Leu Leu Gln Pro Glu Tyr
                1295                1300                1305
        Cys Pro Asp Pro Leu Tyr Glu Val Met Leu Lys Cys Trp His Pro
                1310                1315                1320
        Lys Pro Glu Met Arg Pro Ala Phe Ser Glu Leu Val Ser Lys Ile
                1325                1330                1335
        Ser Thr Ile Phe Ser Thr Phe Ile Gly Glu His Tyr Val His Val
                1340                1345                1350
```

Asn Ala Thr Tyr Val Asn Val Lys Cys Val Ala Pro Tyr Pro Ser
1355               1360               1365

Leu Leu Ser Ser Gln Asp Asn Thr Asp Met Asp Val Asp Thr
1370               1375               1380

<210> SEQ ID NO 4
<211> LENGTH: 1379
<212> TYPE: PRT
<213> ORGANISM: Mus musculus

<400> SEQUENCE: 4

Met Lys Ala Pro Thr Val Leu Ala Pro Gly Ile Leu Val Leu Leu
1               5                   10                  15

Ser Leu Val Gln Arg Ser His Gly Glu Cys Lys Glu Ala Leu Val Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Val Leu His Gly His His Ile Tyr Leu
        50                  55                  60

Gly Ala Thr Asn Tyr Ile Tyr Val Leu Asn Asp Lys Asp Leu Gln Lys
65                  70                  75                  80

Val Ser Glu Phe Lys Thr Gly Pro Val Leu Glu His Pro Asp Cys Leu
                85                  90                  95

Pro Cys Arg Asp Cys Ser Ser Lys Ala Asn Ser Ser Gly Gly Val Trp
            100                 105                 110

Lys Asp Asn Ile Asn Met Ala Leu Leu Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Leu Pro Pro Asp Asn Ser Ala Asp Ile Gln Ser Glu Val His Cys
145                 150                 155                 160

Met Phe Ser Pro Glu Glu Glu Ser Gly Gln Cys Pro Asp Cys Val Val
                165                 170                 175

Ser Ala Leu Gly Ala Lys Val Leu Leu Ser Glu Lys Asp Arg Phe Ile
            180                 185                 190

Asn Phe Phe Val Gly Asn Thr Ile Asn Ser Ser Tyr Pro Pro Gly Tyr
        195                 200                 205

Ser Leu His Ser Ile Ser Val Arg Arg Leu Lys Glu Thr Gln Asp Gly
    210                 215                 220

Phe Lys Phe Leu Thr Asp Gln Ser Tyr Ile Asp Val Leu Pro Glu Phe
225                 230                 235                 240

Gln Asp Ser Tyr Pro Ile Lys Tyr Ile His Ala Phe Glu Ser Asn His
                245                 250                 255

Phe Ile Tyr Phe Leu Thr Val Gln Lys Glu Thr Leu Asp Ala Gln Thr
            260                 265                 270

Phe His Thr Arg Ile Ile Arg Phe Cys Ser Val Asp Ser Gly Leu His
        275                 280                 285

Ser Tyr Met Glu Met Pro Leu Glu Cys Ile Leu Thr Glu Lys Arg Arg
    290                 295                 300

Lys Arg Ser Thr Arg Glu Glu Val Phe Asn Ile Leu Gln Ala Ala Tyr
305                 310                 315                 320

Val Ser Lys Pro Gly Ala Asn Leu Ala Lys Gln Ile Gly Ala Ser Pro
                325                 330                 335

Ser Asp Asp Ile Leu Phe Gly Val Phe Ala Gln Ser Lys Pro Asp Ser

```
            340                 345                 350
Ala Glu Pro Val Asn Arg Ser Ala Val Cys Ala Phe Pro Ile Lys Tyr
            355                 360                 365

Val Asn Asp Phe Phe Asn Lys Ile Val Asn Lys Asn Val Arg Cys
            370                 375             380

Leu Gln His Phe Tyr Gly Pro Asn His Glu His Cys Phe Asn Arg Thr
385                 390                 395                 400

Leu Leu Arg Asn Ser Ser Gly Cys Glu Ala Arg Ser Asp Glu Tyr Arg
                405                 410                 415

Thr Glu Phe Thr Thr Ala Leu Gln Arg Val Asp Leu Phe Met Gly Arg
            420                 425                 430

Leu Asn Gln Val Leu Leu Thr Ser Ile Ser Thr Phe Ile Lys Gly Asp
                435                 440                 445

Leu Thr Ile Ala Asn Leu Gly Thr Ser Glu Gly Arg Phe Met Gln Val
            450                 455                 460

Val Leu Ser Arg Thr Ala His Leu Thr Pro His Val Asn Phe Leu Leu
465                 470                 475                 480

Asp Ser His Pro Val Ser Pro Glu Val Ile Val Glu His Pro Ser Asn
                485                 490                 495

Gln Asn Gly Tyr Thr Leu Val Val Thr Gly Lys Lys Ile Thr Lys Ile
                500                 505                 510

Pro Leu Asn Gly Leu Gly Cys Gly His Phe Gln Ser Cys Ser Gln Cys
            515                 520                 525

Leu Ser Ala Pro Tyr Phe Ile Gln Cys Gly Trp Cys His Asn Gln Cys
            530                 535                 540

Val Arg Phe Asp Glu Cys Pro Ser Gly Thr Trp Thr Gln Glu Ile Cys
545                 550                 555                 560

Leu Pro Ala Val Tyr Lys Val Phe Pro Thr Ser Ala Pro Leu Glu Gly
                565                 570                 575

Gly Thr Val Leu Thr Ile Cys Gly Trp Asp Phe Gly Phe Arg Lys Asn
            580                 585                 590

Asn Lys Phe Asp Leu Arg Lys Thr Lys Val Leu Leu Gly Asn Glu Ser
            595                 600                 605

Cys Thr Leu Thr Leu Ser Glu Ser Thr Thr Asn Thr Leu Lys Cys Thr
            610                 615                 620

Val Gly Pro Ala Met Ser Glu His Phe Asn Val Ser Val Ile Ile Ser
625                 630                 635                 640

Asn Ser Arg Glu Thr Thr Gln Tyr Ser Ala Phe Ser Tyr Val Asp Pro
                645                 650                 655

Val Ile Thr Ser Ile Ser Pro Arg Tyr Gly Pro Gln Ala Gly Gly Thr
            660                 665                 670

Leu Leu Thr Leu Thr Gly Lys Tyr Leu Asn Ser Gly Asn Ser Arg His
                675                 680                 685

Ile Ser Ile Gly Gly Lys Thr Cys Thr Leu Lys Ser Val Ser Asp Ser
            690                 695                 700

Ile Leu Glu Cys Tyr Thr Pro Ala Gln Thr Thr Ser Asp Glu Phe Pro
705                 710                 715                 720

Val Lys Leu Lys Ile Asp Leu Ala Asn Arg Glu Thr Ser Ser Phe Ser
                725                 730                 735

Tyr Arg Glu Asp Pro Val Val Tyr Glu Ile His Pro Thr Lys Ser Phe
            740                 745                 750

Ile Ser Gly Gly Ser Thr Ile Thr Gly Ile Gly Lys Thr Leu Asn Ser
            755                 760                 765
```

-continued

```
Val Ser Leu Pro Lys Leu Val Ile Asp Val His Glu Val Gly Val Asn
    770             775                 780

Tyr Thr Val Ala Cys Gln His Arg Ser Asn Ser Glu Ile Ile Cys Cys
785             790                 795                 800

Thr Thr Pro Ser Leu Lys Gln Leu Gly Leu Gln Leu Pro Leu Lys Thr
                805                 810                 815

Lys Ala Phe Phe Leu Leu Asp Gly Ile Leu Ser Lys His Phe Asp Leu
            820                 825                 830

Thr Tyr Val His Asn Pro Val Phe Glu Pro Phe Glu Lys Pro Val Met
        835                 840                 845

Ile Ser Ile Gly Asn Glu Asn Val Val Glu Ile Lys Gly Asn Asn Ile
    850                 855                 860

Asp Pro Glu Ala Val Lys Gly Glu Val Leu Lys Val Gly Asn Gln Ser
865                 870                 875                 880

Cys Glu Ser Leu His Trp His Ser Gly Ala Val Leu Cys Thr Val Pro
                885                 890                 895

Ser Asp Leu Leu Lys Leu Asn Ser Glu Leu Asn Ile Glu Trp Lys Gln
                900                 905                 910

Ala Val Ser Ser Thr Val Leu Gly Lys Val Ile Val Gln Pro Asp Gln
            915                 920                 925

Asn Phe Ala Gly Leu Ile Ile Gly Ala Val Ser Ile Ser Val Val Val
        930                 935                 940

Leu Leu Leu Ser Gly Leu Phe Leu Trp Met Arg Lys Arg Lys His Lys
945             950                 955                 960

Asp Leu Gly Ser Glu Leu Val Arg Tyr Asp Ala Arg Val His Thr Pro
                965                 970                 975

His Leu Asp Arg Leu Val Ser Ala Arg Ser Val Ser Pro Thr Thr Glu
            980                 985                 990

Met Val Ser Asn Glu Ser Val Asp Tyr Arg Ala Thr Phe Pro Glu Asp
        995                 1000                1005

Gln Phe Pro Asn Ser Ser Gln Asn Gly Ala Cys Arg Gln Val Gln
    1010            1015                1020

Tyr Pro Leu Thr Asp Leu Ser Pro Ile Leu Thr Ser Gly Asp Ser
    1025            1030                1035

Asp Ile Ser Ser Pro Leu Leu Gln Asn Thr Val His Ile Asp Leu
    1040            1045                1050

Ser Ala Leu Asn Pro Glu Leu Val Gln Ala Val Gln His Val Val
    1055            1060                1065

Ile Gly Pro Ser Ser Leu Ile Val His Phe Asn Glu Val Ile Gly
    1070            1075                1080

Arg Gly His Phe Gly Cys Val Tyr His Gly Thr Leu Leu Asp Asn
    1085            1090                1095

Asp Gly Lys Lys Ile His Cys Ala Val Lys Ser Leu Asn Arg Ile
    1100            1105                1110

Thr Asp Ile Glu Glu Val Ser Gln Phe Leu Thr Glu Gly Ile Ile
    1115            1120                1125

Met Lys Asp Phe Ser His Pro Asn Val Leu Ser Leu Leu Gly Ile
    1130            1135                1140

Cys Leu Arg Ser Glu Gly Ser Pro Leu Val Val Leu Pro Tyr Met
    1145            1150                1155

Lys His Gly Asp Leu Arg Asn Phe Ile Arg Asn Glu Thr His Asn
    1160            1165                1170
```

| | | | | | | | | | | | |
|---|---|---|---|---|---|---|---|---|---|---|---|
| Pro | Thr | Val | Lys | Asp | Leu | Ile | Gly | Phe | Gly | Leu | Gln | Val | Ala | Lys |
| 1175 | | | | 1180 | | | | | 1185 | | |

Pro Thr Val Lys Asp Leu Ile Gly Phe Gly Leu Gln Val Ala Lys
    1175                1180                1185

Gly Met Lys Tyr Leu Ala Ser Lys Lys Phe Val His Arg Asp Leu
    1190                1195                1200

Ala Ala Arg Asn Cys Met Leu Asp Glu Lys Phe Thr Val Lys Val
    1205                1210                1215

Ala Asp Phe Gly Leu Ala Arg Asp Met Tyr Asp Lys Glu Tyr Tyr
    1220                1225                1230

Ser Val His Asn Lys Thr Gly Ala Lys Leu Pro Val Lys Trp Met
    1235                1240                1245

Ala Leu Glu Ser Leu Gln Thr Gln Lys Phe Thr Thr Lys Ser Asp
    1250                1255                1260

Val Trp Ser Phe Gly Val Leu Leu Trp Glu Leu Met Thr Arg Gly
    1265                1270                1275

Ala Pro Pro Tyr Pro Asp Val Asn Thr Phe Asp Ile Thr Ile Tyr
    1280                1285                1290

Leu Leu Gln Gly Arg Arg Leu Leu Gln Pro Glu Tyr Cys Pro Asp
    1295                1300                1305

Ala Leu Tyr Glu Val Met Leu Lys Cys Trp His Pro Lys Ala Glu
    1310                1315                1320

Met Arg Pro Ser Phe Ser Glu Leu Val Ser Arg Ile Ser Ser Ile
    1325                1330                1335

Phe Ser Thr Phe Ile Gly Glu His Tyr Val His Val Asn Ala Thr
    1340                1345                1350

Tyr Val Asn Val Lys Cys Val Ala Pro Tyr Pro Ser Leu Leu Pro
    1355                1360                1365

Ser Gln Asp Asn Ile Asp Gly Glu Gly Asn Thr
    1370                1375

<210> SEQ ID NO 5
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 5
cagatccatt tggggcagtc tggacctgag ctgaagaagc ctggagagac agtcaagatc    60
tcctgcaagg cttctgggta taccttcaca aactttagaa tgaactgggt gaagcaggct   120
ccaggaaagg gtttaaagtg gatgggctgg ataaacacct acactggaga gccaacatat   180
gttgatgact tgaagggacg gtttgccttc tctttggaaa cctctgccag cactgcctat   240
ttgcagatca acaacctcaa aaatgaggac atggctacat atttctgtgc aaggaaaggg   300
attgcgaggg ctatggacta ctggggtcaa ggaacctcag tcaccgtctc gagt        354

<210> SEQ ID NO 6
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 6

Gln Ile His Leu Gly Gln Ser Gly Pro Glu Leu Lys Lys Pro Gly Glu

```
  1               5                  10                 15
Thr Val Lys Ile Ser Cys Lys Ala Ser Gly Tyr Thr Phe Thr Asn Phe
                20                 25                 30

Arg Met Asn Trp Val Lys Gln Ala Pro Gly Lys Gly Leu Lys Trp Met
            35                 40                 45

Gly Trp Ile Asn Thr Tyr Thr Gly Glu Pro Thr Tyr Val Asp Asp Leu
        50                 55                 60

Lys Gly Arg Phe Ala Phe Ser Leu Glu Thr Ser Ala Ser Thr Ala Tyr
65                  70                 75                 80

Leu Gln Ile Asn Asn Leu Lys Asn Glu Asp Met Ala Thr Tyr Phe Cys
                85                 90                 95

Ala Arg Lys Gly Ile Ala Arg Ala Met Asp Tyr Trp Gly Gln Gly Thr
            100                105                110

Ser Val Thr Val Ser Ser
            115

<210> SEQ ID NO 7
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
aacattgtga tgacacagtc tccatcctcc ctgagtgtgt cagcaggaga gatggtcact     60
atgagttgta agtccagtca gagtctgtta gacagtggaa atcaaaagaa ctacttggcc    120
tggtaccagc agaaaccagg gcagcctcct caacttttga tcttcggggc atccactagg    180
gaatctgggg tccctgatcg cttcacaggc agtggatctg gaaccgattt cactcttacc    240
gtcagcagtg tgcaggctga agacctggca gtttattact gtcagaatga tcatagttat    300
ccgtacacgt tcggaggggg gaccaagctg gaaataaaa                            339

<210> SEQ ID NO 8
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asn Ile Val Met Thr Gln Ser Pro Ser Ser Leu Ser Val Ser Ala Gly
1               5                  10                 15

Glu Met Val Thr Met Ser Cys Lys Ser Ser Gln Ser Leu Leu Asp Ser
                20                 25                 30

Gly Asn Gln Lys Asn Tyr Leu Ala Trp Tyr Gln Gln Lys Pro Gly Gln
            35                 40                 45

Pro Pro Gln Leu Leu Ile Phe Gly Ala Ser Thr Arg Glu Ser Gly Val
        50                 55                 60

Pro Asp Arg Phe Thr Gly Ser Gly Ser Gly Thr Asp Phe Thr Leu Thr
65                  70                 75                 80

Val Ser Ser Val Gln Ala Glu Asp Leu Ala Val Tyr Tyr Cys Gln Asn
                85                 90                 95

Asp His Ser Tyr Pro Tyr Thr Phe Gly Gly Gly Thr Lys Leu Glu Ile
            100                105                110
```

Lys

<210> SEQ ID NO 9
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 9

```
caggtccaac tgcaacagcc tggggctgaa ctggcaaaac ctggggcctc agtgaggatg      60
tcctgcaagg cttctggcta cacctttact agttactgga tgcactgggt aaaacagagg     120
cctggacagg gtctggaatg gattggatac attaatccta gcagtggtca tattgagaac     180
aatcagaagt tcaaggacaa ggccacattg actgcagaca atcctccag cacagcctac      240 atgcaactga gcagcctgac atttgaggac tctgcagtct attactgtgc aagaggacgg     300
tttgcttact ggggccaagg gactctggtc actgtctcga gt                        342
```

<210> SEQ ID NO 10
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 10

Gln Val Gln Leu Gln Gln Pro Gly Ala Glu Leu Ala Lys Pro Gly Ala
1               5                   10                  15

Ser Val Arg Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly His Ile Glu Asn Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Ala Arg Gly Arg Phe Ala Tyr Trp Gly Gln Gly Thr Leu Val Thr Val
            100                 105                 110

Ser Ser

<210> SEQ ID NO 11
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 11

```
gatattgtga tgacccagtc tccagcaatc atgtctgcat ctcctgggga gaaggtcacc      60
ttgacctgca gtgccagctc aagtgtaagt tccggctact tgtactggta ccagcagaag     120
ccaggatcct cccccaaact ctggatttat agcacatcca acctggcttc tggagtccct     180
```

```
gctcgcttca gtggcagtgg gtctgggacc tcttactctc tcacagtcaa cagcatggag    240
gctgaagatg ctgcctctta tttctgccat cagtggagta gttacccatt cacgttcggc    300
tcggggacca agctggagct gaaa                                            324
```

<210> SEQ ID NO 12
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Asp Ile Val Met Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Gly
                20                  25                  30

Tyr Leu Tyr Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Val Asn Ser Met Glu
65                  70                  75                  80

Ala Glu Asp Ala Ala Ser Tyr Phe Cys His Gln Trp Ser Ser Tyr Pro
                85                  90                  95

Phe Thr Phe Gly Ser Gly Thr Lys Leu Glu Leu Lys
            100                 105
```

<210> SEQ ID NO 13
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
caggtgcagc tggtgcagtc tggatccgag ctgaagaaac ctggcgcctc cgtgaaggtg     60
tcctgcaagg cttccggcta cacctttacc aacttccgga tgaactgggt caagcaggcc    120
ccaggccagg gcctgaaatg gatgggctgg atcaacacct acaccggcga gcccacctac    180
gtggacgacc tgaagggcag attcgtgttc tccctggaca cctccgtgtc caccgcctac    240
ctgcagatct ccagcctgaa ggccgaggat accgccgtgt actactgcgc ccggaaggga    300
atcgccagag ccatggatta ttggggccag ggcaccaccg tgacagtctc gagt          354
```

<210> SEQ ID NO 14
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Gln Val Gln Leu Val Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Asn Phe
            20                  25                  30

Arg Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Val Asp Asp Leu
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Ile Ala Arg Ala Met Asp Tyr Trp Gly Gln Gly Thr
            100                 105                 110

Thr Val Thr Val Ser Ser
            115

<210> SEQ ID NO 15
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
gacatcgtga tgacccagtc ccccgactct ctggccgtgt ctctgggcga gagagccacc        60
atcaactgca gtcctccca gtccctgctg gactccggca accagaagaa ctacctggcc       120
tggtatcagc agaagcccgg ccagcctccc aagctgctga tctttggcgc ctccacccgg       180
gaatctggcg tgcccgatag attctccggc tccggctctg gcaccgactt taccctgacc       240
atcagctccc tgcaggccga ggatgtggcc gtgtactact gccagaacga ccactcctac       300
ccctacacct tcggccaggg caccaagctg gaaatcaag                              339

<210> SEQ ID NO 16
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Phe Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Ser Tyr Pro Tyr Thr Phe Gly Gln Gly Thr Lys Leu Glu Ile
            100                 105                 110

Lys
```

<210> SEQ ID NO 17
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
caggtgcagc tggtgcagtc tggcgctgaa gtgaagaaac ccggctcctc cgtgaaggtg     60
tcctgcaagg cctccggcta cacctttacc agctactgga tgcactgggt gcgacaggcc    120
cctggacagg gcctggaatg gatgggctac atcaacccct ccagcggcca catcgagaac    180
aaccagaaat tcaaggaccg cgtgaccatc accgccgaca gtccacctc caccgcctac    240 atggaactgt cctccctgcg gagcgaggac accgccgtgt actactgtgc cagaggcaga    300
ttcgcctact ggggccaggg caccctcgtg acagtctcga gt                       342

<210> SEQ ID NO 18
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Tyr Ile Asn Pro Ser Ser Gly His Ile Glu Asn Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Phe Ala Tyr Trp Gly Gln Gly Thr Leu Val Thr Val
            100                 105                 110

Ser Ser

<210> SEQ ID NO 19
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
gagatcgtgc tgacccagtc tcctgccacc ctgtctctga gccctggcga gagagctacc     60
ctgtcctgct ccgcctcctc ctctgtgtcc tccggctacc tgtactggta tcagcagaag    120
cccggccagg cccctcggct gctgatctac tctacctcca acctggcctc cggcatccct    180
gccagattct ccggctctgg ctctggcacc gactttaccc tgaccatctc cagcctggaa    240

```
cccgaggact tcgccgtgta ctactgccac cagtggtcca gctacccctt cacctttggc    300
tccggcacca agctggaaat caag                                           324
```

<210> SEQ ID NO 20
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Gly
            20                  25                  30

Tyr Leu Tyr Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Ser Tyr Pro
                85                  90                  95

Phe Thr Phe Gly Ser Gly Thr Lys Leu Glu Ile Lys
            100                 105
```

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 21

```
Gly Tyr Thr Phe Thr Asn Phe Arg
1               5
```

<210> SEQ ID NO 22
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 22

```
Ile Asn Thr Tyr Thr Gly Glu Pro
1               5
```

<210> SEQ ID NO 23
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 23

```
Ala Arg Lys Gly Ile Ala Arg Ala Met Asp Tyr
1               5                   10

<210> SEQ ID NO 24
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gln Ser Leu Leu Asp Ser Gly Asn Gln Lys Asn Tyr
1               5                   10

<210> SEQ ID NO 25
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Ala Ser
1

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gln Asn Asp His Ser Tyr Pro Tyr Thr
1               5

<210> SEQ ID NO 27
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Tyr Thr Phe Thr Ser Tyr Trp
1               5

<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ile Asn Pro Ser Ser Gly His Ile
1               5
```

```
<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ala Arg Gly Arg Phe Ala Tyr
1               5

<210> SEQ ID NO 30
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ser Ser Val Ser Ser Gly Tyr
1               5

<210> SEQ ID NO 31
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ser Thr Ser
1

<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

His Gln Trp Ser Ser Tyr Pro Phe Thr
1               5

<210> SEQ ID NO 33
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
            20                  25                  30

Gly Asn Gln Lys Asn Tyr Leu Ala Trp Tyr Gln Gln Lys Pro Gly Gln
```

```
                35                  40                  45
Pro Pro Lys Leu Leu Ile Phe Gly Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp His Ser Tyr Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220
```

<210> SEQ ID NO 34
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Phe
                 20                  25                  30

Arg Met Asn Trp Val Lys Gln Ala Pro Gly Gln Gly Leu Lys Trp Met
             35                  40                  45

Gly Trp Ile Asn Thr Tyr Thr Gly Glu Pro Thr Tyr Val Asp Asp Leu
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Lys Gly Ile Ala Arg Ala Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 35
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Gly
            20                  25                  30

Tyr Leu Tyr Trp Tyr Gln Gln Lys Pro Gly Gln Ala Pro Arg Leu Leu
            35                  40                  45

Ile Tyr Ser Thr Ser Asn Leu Ala Ser Gly Ile Pro Ala Arg Phe Ser
            50                  55                  60

Gly Ser Gly Ser Gly Thr Asp Phe Thr Leu Thr Ile Ser Ser Leu Glu
65                  70                  75                  80
```

```
Pro Glu Asp Phe Ala Val Tyr Tyr Cys His Gln Trp Ser Ser Tyr Pro
                85                  90                  95

Phe Thr Phe Gly Ser Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Ala Asn Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 36
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Tyr Ile Asn Pro Ser Ser Gly His Ile Glu Asn Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Phe Ala Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
```

```
            210                 215                 220
Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
                275                 280                 285

Arg Glu Glu Gln Tyr Asn Ser Thr Tyr Arg Val Val Ser Val Leu Thr
                290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly
                435                 440

<210> SEQ ID NO 37
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ser Thr Trp Trp Lys Glu Pro Leu Asn Ile Val Ser Phe Leu Phe Cys
1               5                   10                  15

Phe Ala Ser

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gly Gly Gly Gly Ser Gly Gly Gly Ser Gly Gly Gly Gly Ser
1               5                   10                  15

<210> SEQ ID NO 39
<211> LENGTH: 14
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Lys Pro Ile Pro Asn Pro Leu Leu Gly Leu Asp Ser Thr
1               5                   10
```

UNITED STATES PATENT AND TRADEMARK OFFICE
CERTIFICATE OF CORRECTION

| | |
|---|---|
| PATENT NO. | : 10,450,376 B2 |
| APPLICATION NO. | : 15/510545 |
| DATED | : October 22, 2019 |
| INVENTOR(S) | : Bouquin et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 112 days.

Signed and Sealed this
Eleventh Day of October, 2022

Katherine Kelly Vidal
*Director of the United States Patent and Trademark Office*